US010981864B2

(12) United States Patent
Becker et al.

(10) Patent No.: US 10,981,864 B2
(45) Date of Patent: Apr. 20, 2021

(54) CRYSTALLINE MODIFICATIONS OF N-(4,5-BISMETHANESULFONYL-2-METHYLBENZOYL)GUANIDINE HYDROCHLORIDE AND N-(4,5-BISMETHANESULFONYL-2-METHYLBENZOYL)GUANIDINE SALTS

(71) Applicant: MERCK PATENT GMBH, Darmstadt (DE)

(72) Inventors: Axel Becker, Seeheim-Jugenheim (DE); Gilmary Gallon, Le Puy en Velay (FR); Christoph Saal, Otzberg (DE); Clemens Kuehn, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 59 days.

(21) Appl. No.: 16/076,017

(22) PCT Filed: Jan. 27, 2017

(86) PCT No.: PCT/EP2017/000102
§ 371 (c)(1),
(2) Date: Aug. 7, 2018

(87) PCT Pub. No.: WO2017/137147
PCT Pub. Date: Aug. 17, 2017

(65) Prior Publication Data
US 2019/0345100 A1   Nov. 14, 2019

(30) Foreign Application Priority Data
Feb. 8, 2016 (EP) .................................. 16154672

(51) Int. Cl.
C07C 317/44 (2006.01)
(52) U.S. Cl.
CPC ........ *C07C 317/44* (2013.01); *C07B 2200/13* (2013.01)
(58) Field of Classification Search
CPC .................................................. C07C 317/44
See application file for complete search history.

(56) References Cited

U.S. PATENT DOCUMENTS 5,744,641 A   4/1998  Gericke et al.
6,673,968 B1  1/2004  Gericke et al.

FOREIGN PATENT DOCUMENTS

EP    0 758 644      2/1997
WO    WO 01/30750    5/2001
WO    WO 2009/135583 11/2009

OTHER PUBLICATIONS

Caira, M. R. "Crystalline Polymorphism of Organic Compounds" *Topics in Current Chemistry*, 1998, pp. 164-207, vol. 198.
Written Opinion in International Application No. PCT/EP2017/000102, dated Jun. 27, 2017, pp. 1-17.
Lupachyk, S. et al. "Treatment of peripheral diabetic neuropathy in Zucker diabetic fatty (ZDF) rats with cariporide" *Journal of Diabetes Mellitus*, 2014, pp. 59-66, vol. 4, No. 1.
Bkaily, G. et al. "$Na^+$—$H^+$ exchanger inhibitor prevents early death in hereditary cardiomyopathy" *Can. J. Physiol. Pharmacol.*, Apr. 24, 2015, pp. 1-12, vol. 93.
Porte-Thome, F. et al. "Development of Rimeporide, a sodium-hydrogen exchanger (NHE-1) inhibitor, for patients with Duchenne muscular dystrophy" *Abstracts /Neuromuscular Disorders*, 2015, pp. S259-S260, vol. 25.
Karki, P. et al. "B-Raf Associates with and Activates the NHE1 Isoform of the $Na^+/H^+$ Exchanger" *The Journal of Biological Chemistry*, Apr. 15, 2011, pp. 13096-13105, vol. 286, No. 15.
Harguindey, S. et al. "Cariporide and other new and powerful NHE1 inhibitors as potentially selective anticancer drugs—an integral molecular/biochemical/metabolic/clinical approach after one hundred years of cancer research" *Journal of Translational Medicine*, 2013, pp. 1-17, vol. 11, No. 282.
Reshkin, S. J. et al. "Paclitaxel Induces Apoptosis via Protein Kinase A- and p38 Mitogen-activated Protein-dependent Inhibition of the $Na^+/H^+$ Exchanger (NHE) NHE Isoform 1 in Human Breast Cancer Cells" *Clinical Cancer Research*, Jun. 2003, pp. 2366-2373, vol. 9.
Pouysségur, J. et al. "Hypoxia signalling in cancer and approaches to enforce tumour regression" *Nature*, May 25, 2006, pp. 437-443, vol. 441.
Gao, W. et al. "Inhibition of K562 leukemia angiogenesis and growth by selective $Na^+/H^+$ exchanger inhibitor cariporide through down-regulation of pro-angiogenesis factor VEGF" *Leukemia Research*, 2011, pp. 1506-1511, No. 35.
Lin, Y. et al. "NHE1 mediates MDA-MB-231 cells invasion through the regulation of MT1-MMP" *Experimental Cell Research*, 2011, pp. 2031-2040, vol. 317.
Liu, Y. et al. "Roles of $Na^+/H^+$Exchanger Type 1 and Intracellular pH in Angiotensin II-Induced Reactive Oxygen Species Generation and Podocyte Apoptosis" *J Pharmacol Sci.*, 2013, pp. 1-13, vol. 122, No. 3.
Li, P. et al. "Inhibition of $Na^+/H^+$ Exchanger 1 Attenuates Renal Dysfunction Induced by Advanced Glycation End Products in Rats" *Journal of Diabetes Research*, 2016, pp. 1-10.
Liu, Y. et al. "CHP1-Mediated NHE1 Biosynthetic Maturation is Required for Purkinje Cell Axon Homeostasis" *The Journal of Neuroscience*, Jul. 31, 2013, pp. 12656-12669, vol. 33, No. 31.
Meyrick, B. et al. "Pulmonary Hypertension. Anatomic and Physiologic Correlates" *Clinics in Chest Medicine*, May 1983, pp. 199-217, vol. 4, No. 2.

(Continued)

Primary Examiner — Shawquia Jackson
(74) Attorney, Agent, or Firm — Saliwanchik, Lloyd & Eisenschenk

(57) ABSTRACT

The present invention relates to novel crystalline modifications of N-(4,5-bismethanesulfonyl-2-methylbenzoyl)guanidine hydrochloride, novel N-(4,5-bismethanesulfonyl-2-methylbenzoyl)guanidine salts and their crystalline modifications and processes of manufacturing and pharmaceutical formulations thereof.

14 Claims, 38 Drawing Sheets

(56) References Cited

OTHER PUBLICATIONS

Grinstein, S. et al. "$Na^+/H^+$ exchange and growth factor-induced cytosolic pH changes. Role in cellular proliferation" *Biochimica et Biophysica Acta*, 1989, pp. 73-97, No. 988.

Huetsch, J. et al. "$Na^+/H^+$ exchange and hypoxic pulmonary hypertension" *Pulmonary Circulation*, Jun. 2015, pp. 228-243, vol. 5, No. 2.

Wu, D. et al. "Inhibition of Human Pulmonary Artery Smooth Muscle Cell Proliferation and Migration by Sabiporide, a New Specific NHE-1 Inhibitor" *J Cardiovasc Pharmacol*, Aug. 2006, pp. 34-40, vol. 48, No. 2.

Huetsch, J. et al. "The Na+/H+ exchanger contributes to increased smooth muscle proliferation and migration in a rat model of pulmonary arterial hypertension" *Physiological Reports*, 2016, pp. 1-14, vol. 4, No. 5.

Chen, L. et al. "Attenuation of Compensatory Right Ventricular Hypertrophy and Heart Failure following Monocrotaline-Induced Pulmonary Vascular Injury by the $Na^+$—$H^+$ Exchange Inhibitor Cariporide" The Journal of Pharmacology and Experimental Therapeutics, 2001, pp. 469-476, vol. 298, No. 2.

Rubens, C. et al. "Big Endothelin-1 and Endothelin-1 Plasma Levels Are Correlated With the Severity of Primary Pulmonary Hypertension" *Chest*, Nov. 2001, pp. 1562-1569, vol. 120, No. 5.

Undem, C. et al. "Endothelin-1 Augments $Na^+/H^+$ Exchange Activity in Murine Pulmonary Arterial Smooth Muscle Cells via Rho Kinase" *PLOS One*, Sep. 28, 2012, pp. 1-9, vol. 7, No. 9.

Bernstein et al. "Polimorfizm molekulyarnych kristallov" Moscow, Nauka, 2007, pp. 324-330, Chapter 7.3.2 Biodostupnost.

Yu, L. "Amorphous pharmaceutical solids: preparation, characterization and stabilization" *Advanced Drug Delivery Reviews*, 2001, pp. 27-42, vol. 48.

Rodriguez-Spong, B. et al. "General principles of pharmaceutical solid polymorphism: a supramolecular perspective" *Advanced Drug Delivery Reviews*, 2004, pp. 241-274, vol. 56.

Azevedo, M. "EspeRare Receives European Orphan Drug Designation for Rimeporide in Duchenne Muscular Dystrophy" *Muscular Dystrophy News Today*, May 5, 2015, pp. 1-7.

Office Action in Russian Patent Application No. 2018 131 500; dated Jul. 30, 2020, pp. 1-21.

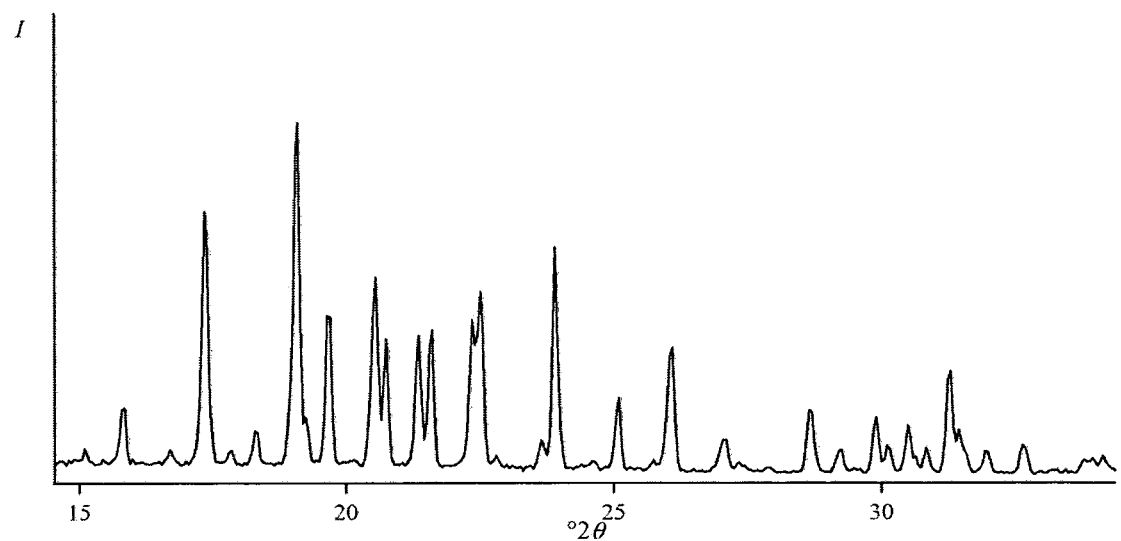
Fig. 1a Powder X-ray diffractogram of HCl salt form HCl-H1
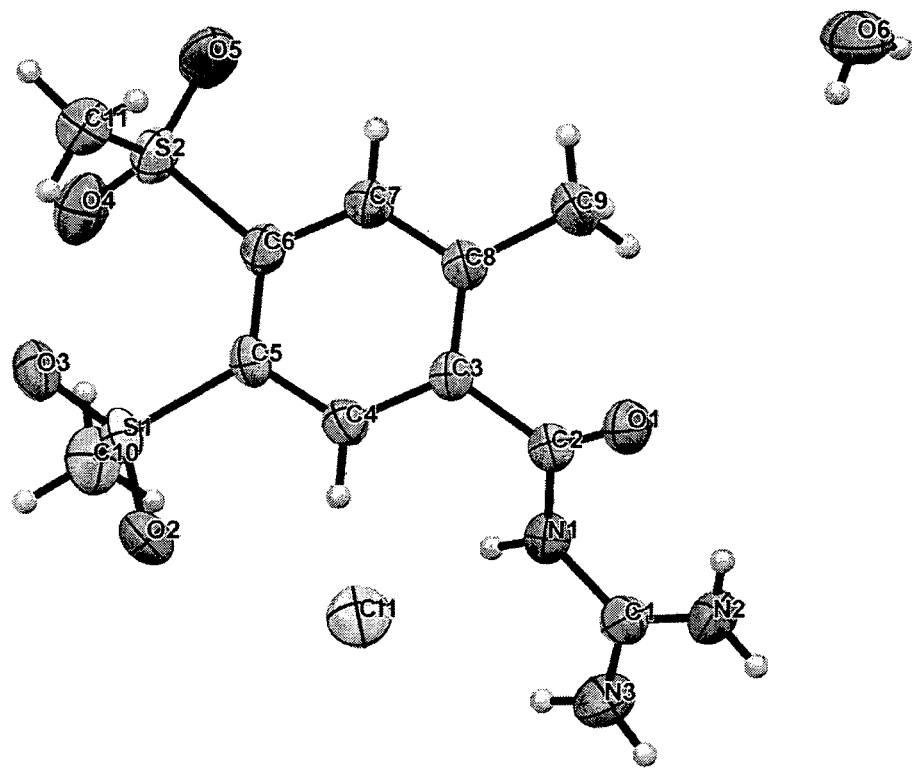
Fig. 1b Single crystal structure of HCl salt form HCl-H1 viewed approx. along a-axis

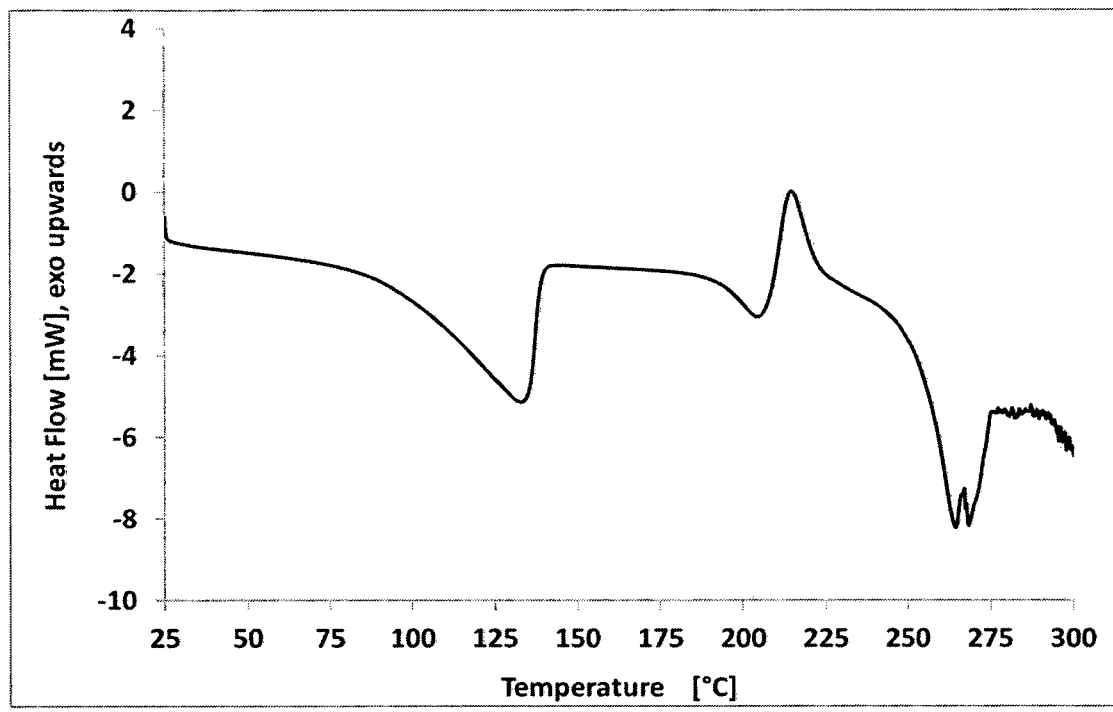
Fig. 1c DSC scan of HCl salt form HCl-H1 (5 K/min)
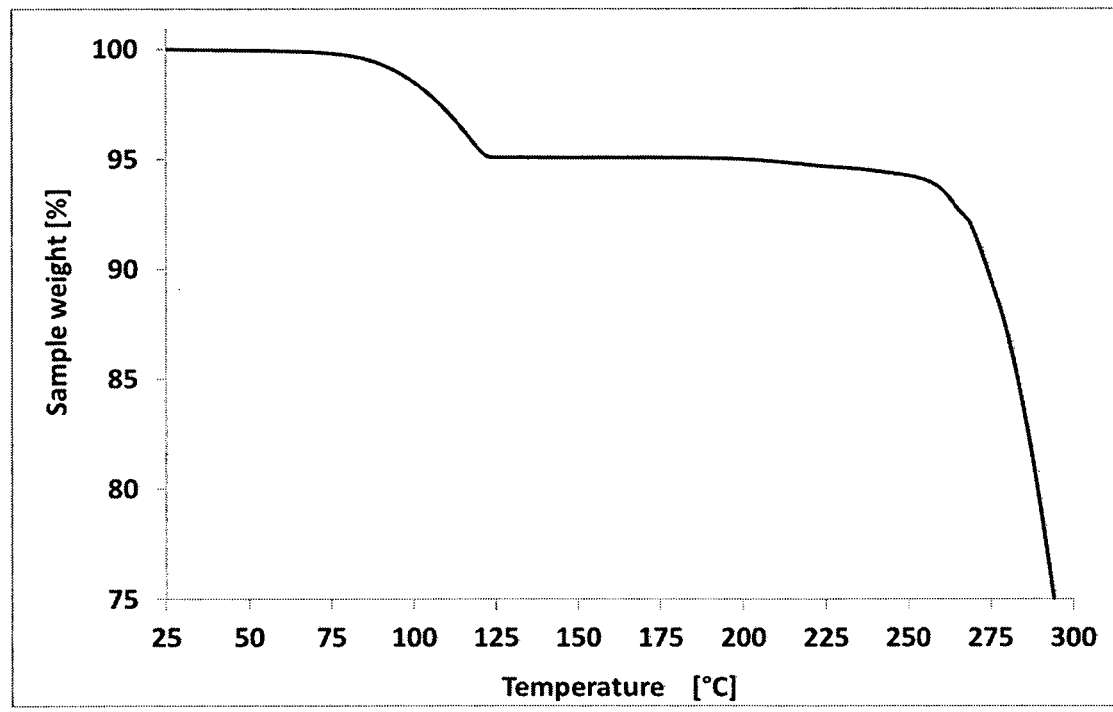
Fig. 1d TGA scan of HCl salt form HCl-H1 (5 K/min)

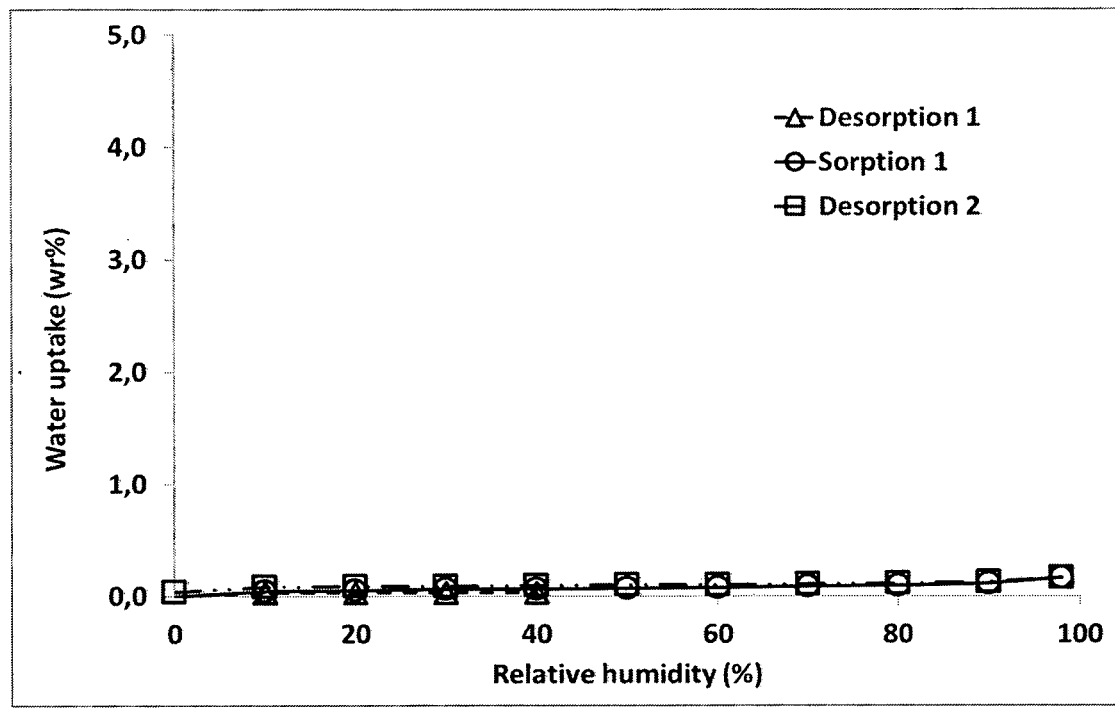
Fig. 1e Water Vapour Sorption Isotherm (25 °C) of HCl salt form HCl-H1
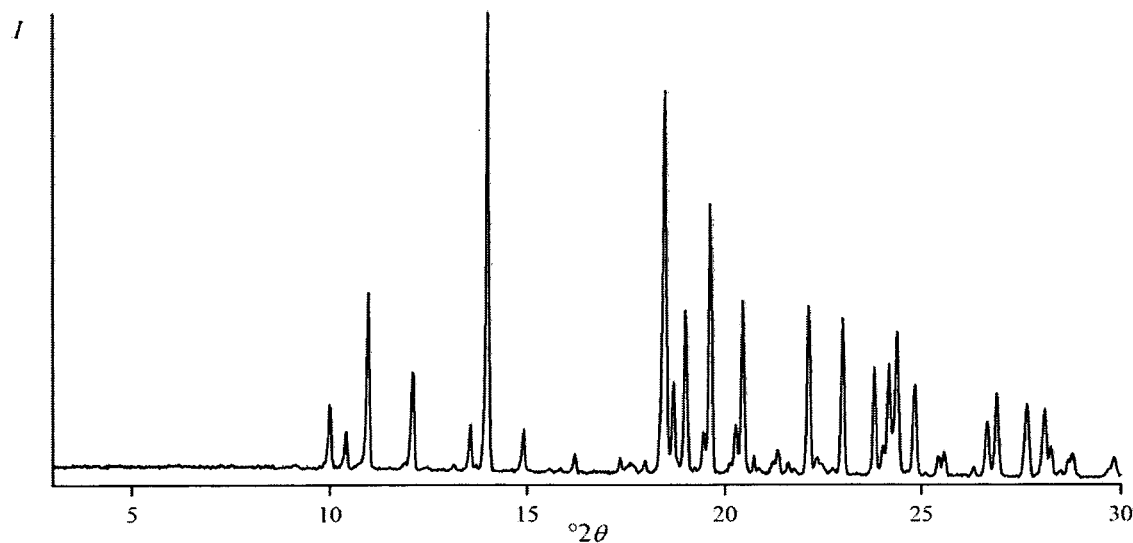
Fig. 2a Powder X-ray diffractogram of HCl salt form HCl-A1

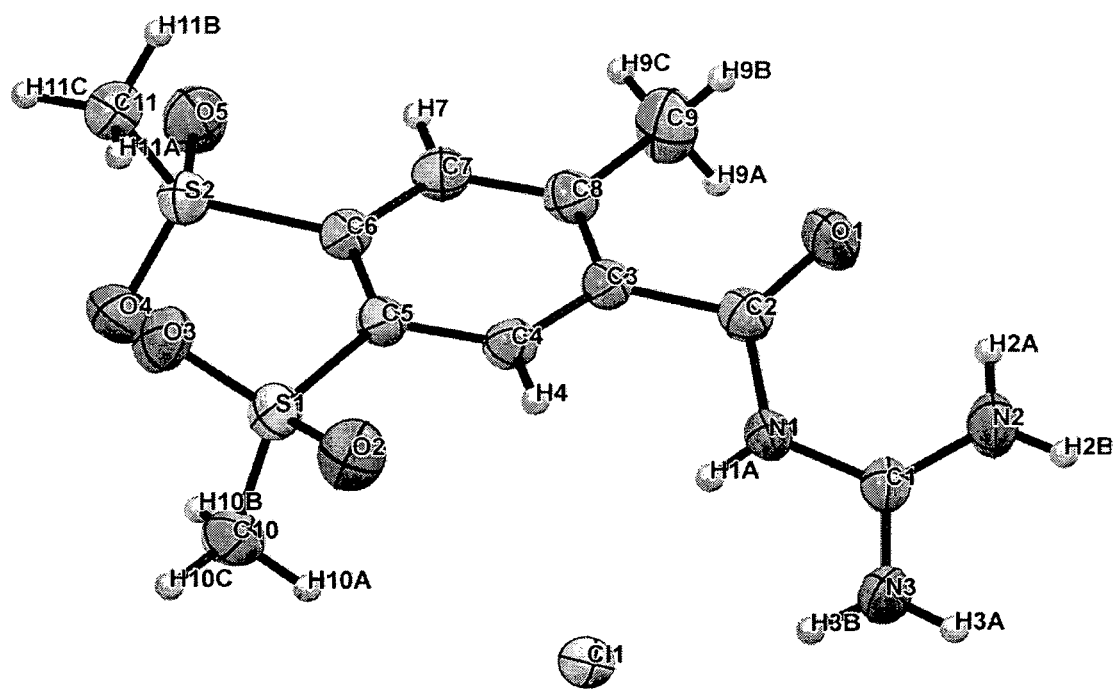
Fig. 2b Single crystal structure of HCl salt form HCl-A1 viewed approx. along a-axis
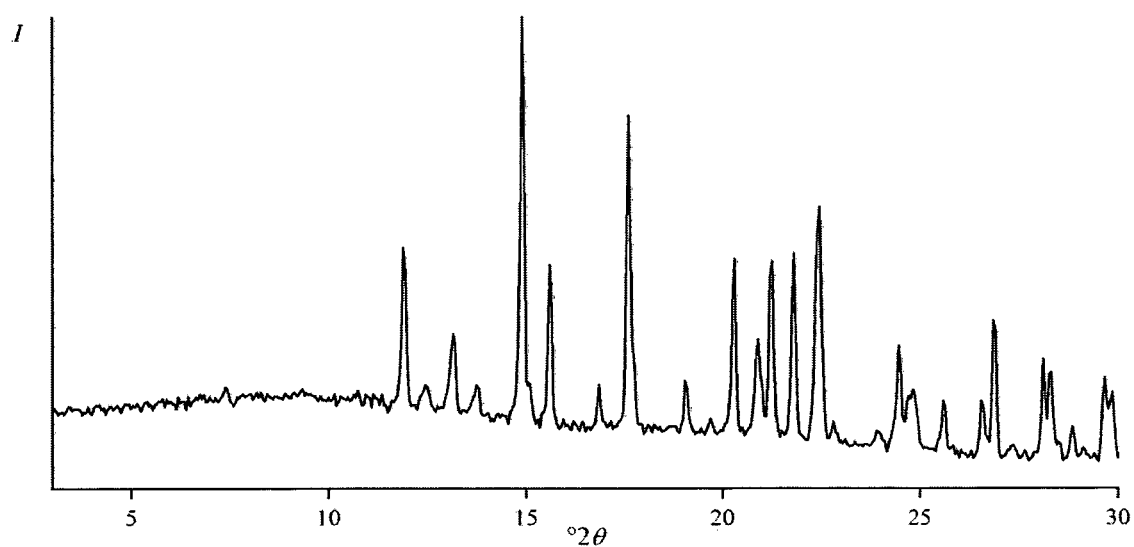
Fig. 3a Powder X-ray diffractogram of HCl salt form HCl-A2

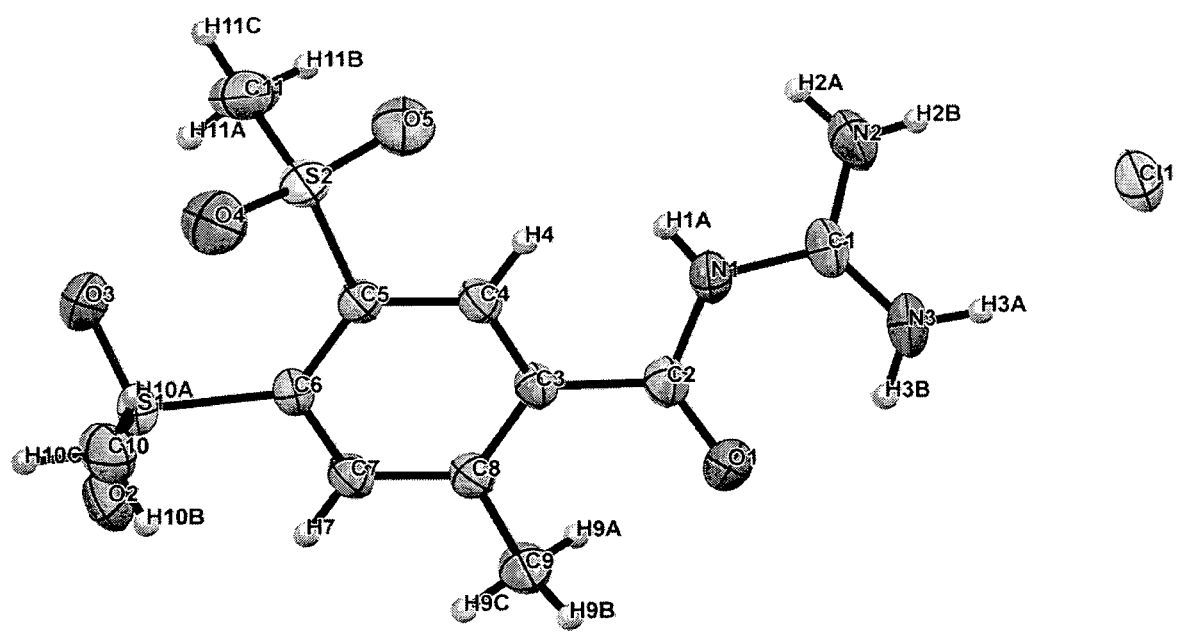
Fig. 3b Single crystal structure of HCl salt form HCl-A2 viewed approx. along [111]
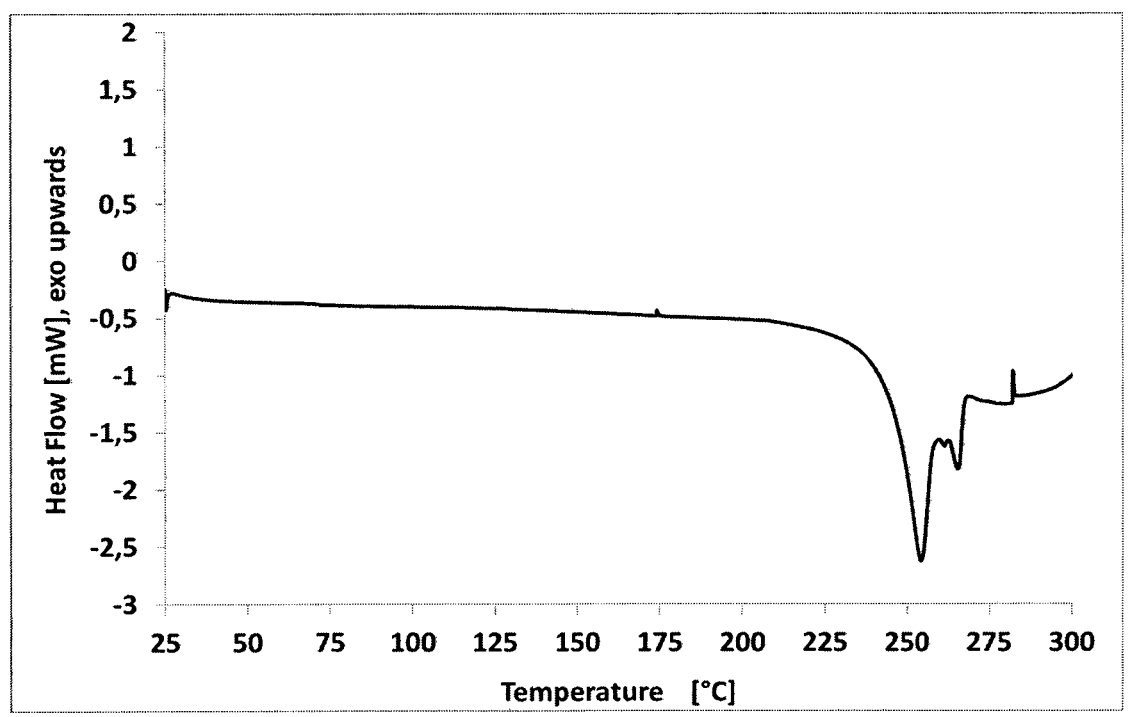
Fig. 3c DSC scan of HCl salt form HCl-A2 (5 K/min)

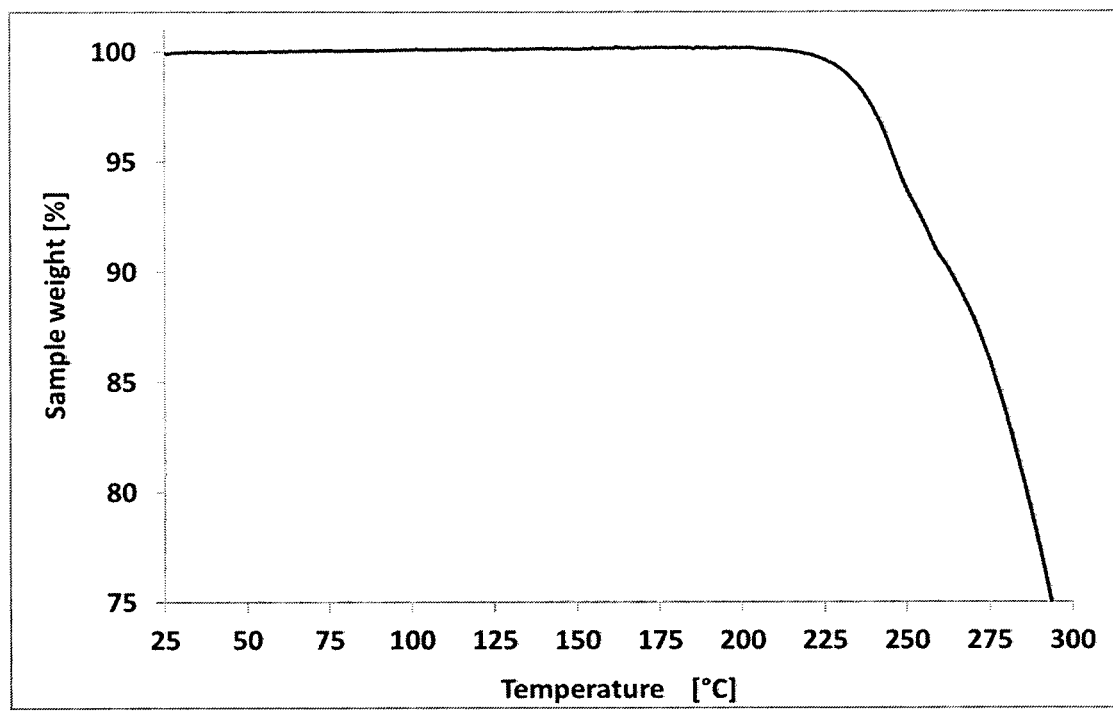
Fig. 3d TGA scan of HCl salt form HCl-A2 (5 K/min)
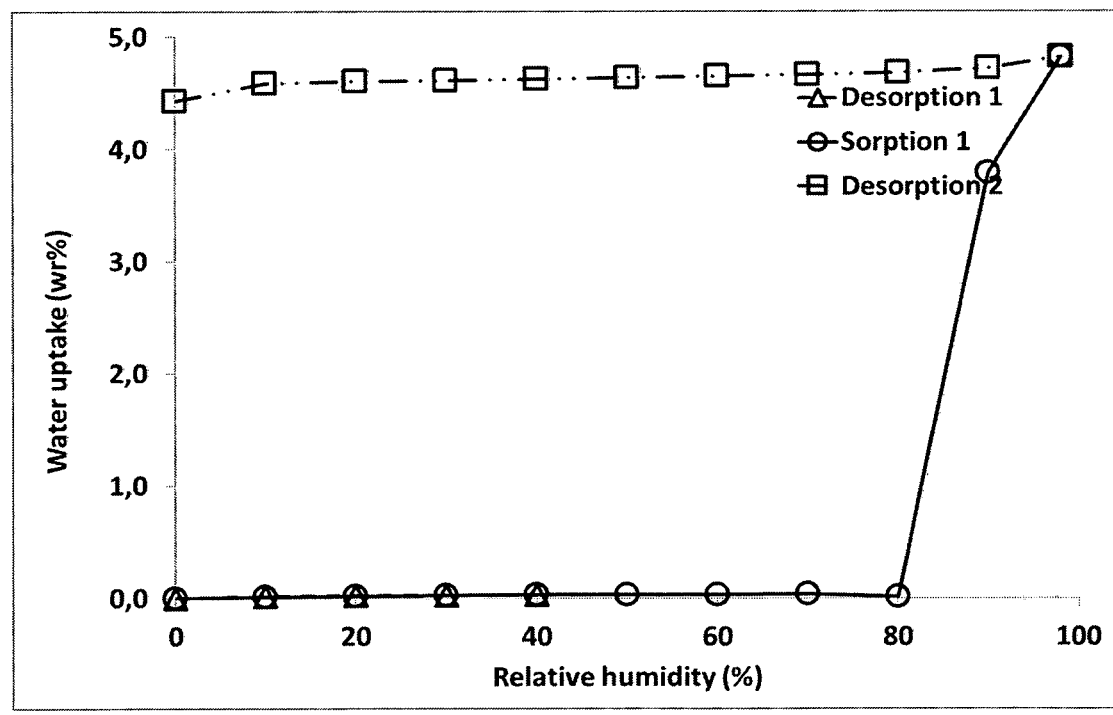
Fig. 3e Water Vapour Sorption Isotherm (25 °C) of HCl salt form HCl-A2

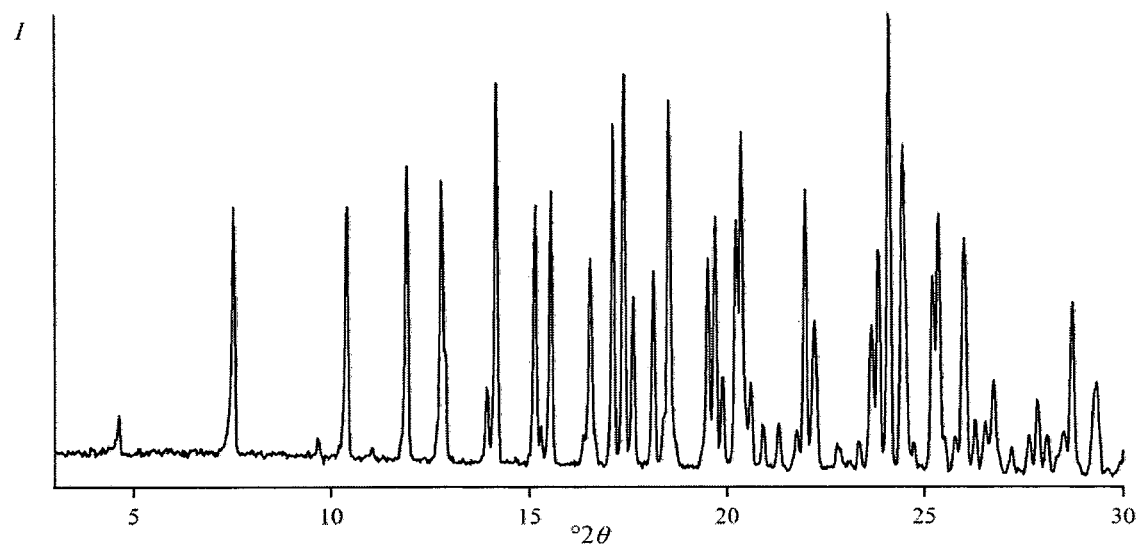
Fig. 4a Powder X-ray diffractogram of HCl salt form HCl-A3
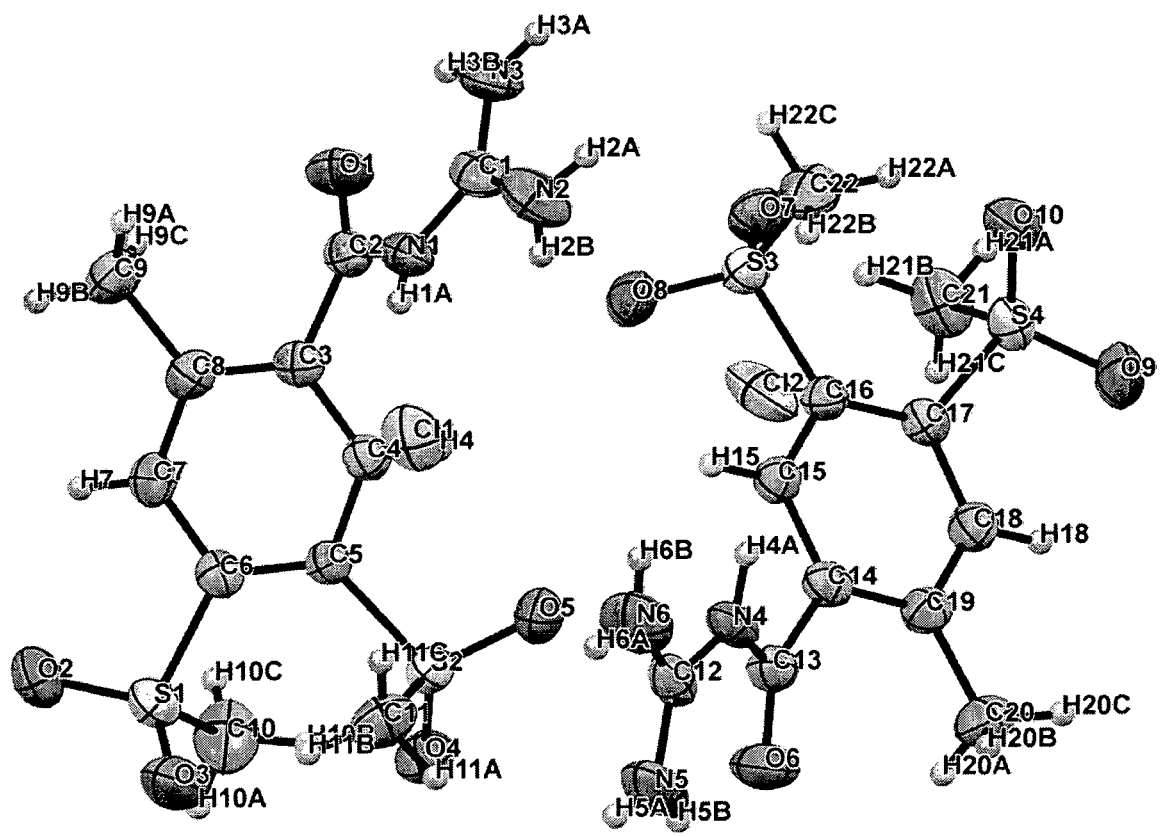
Fig. 4b Single crystal structure of HCl salt form HCl-A3 viewed approx. along b-axis

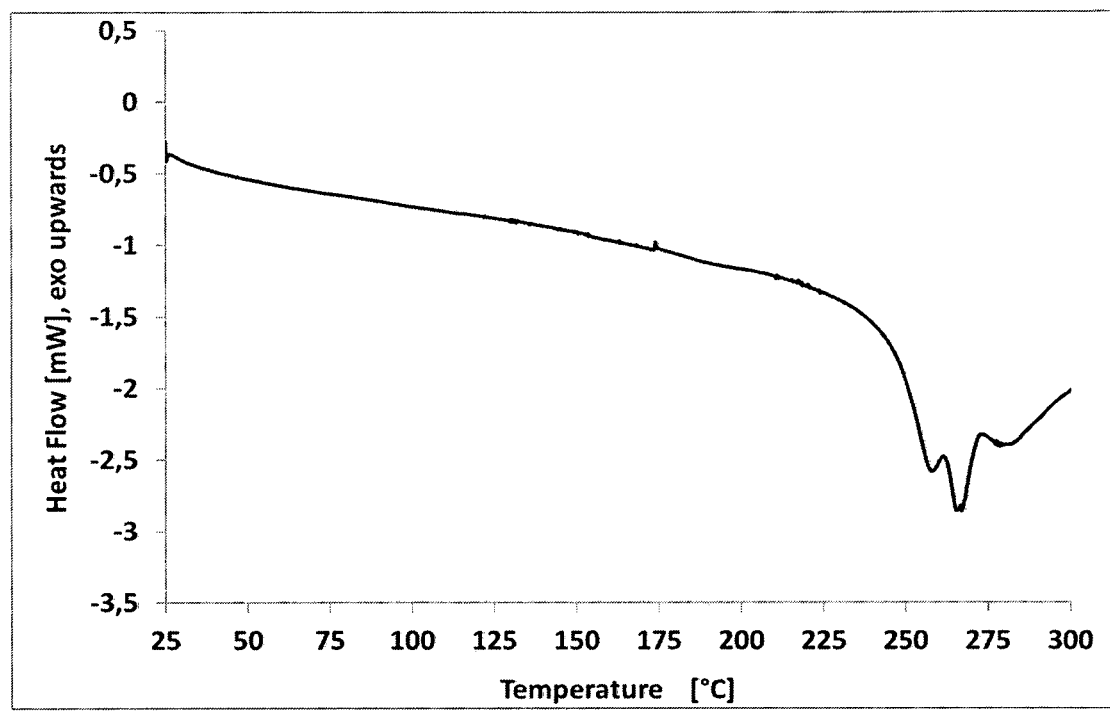
Fig. 4c DSC scan of HCl salt form HCl-A3 (5 K/min)
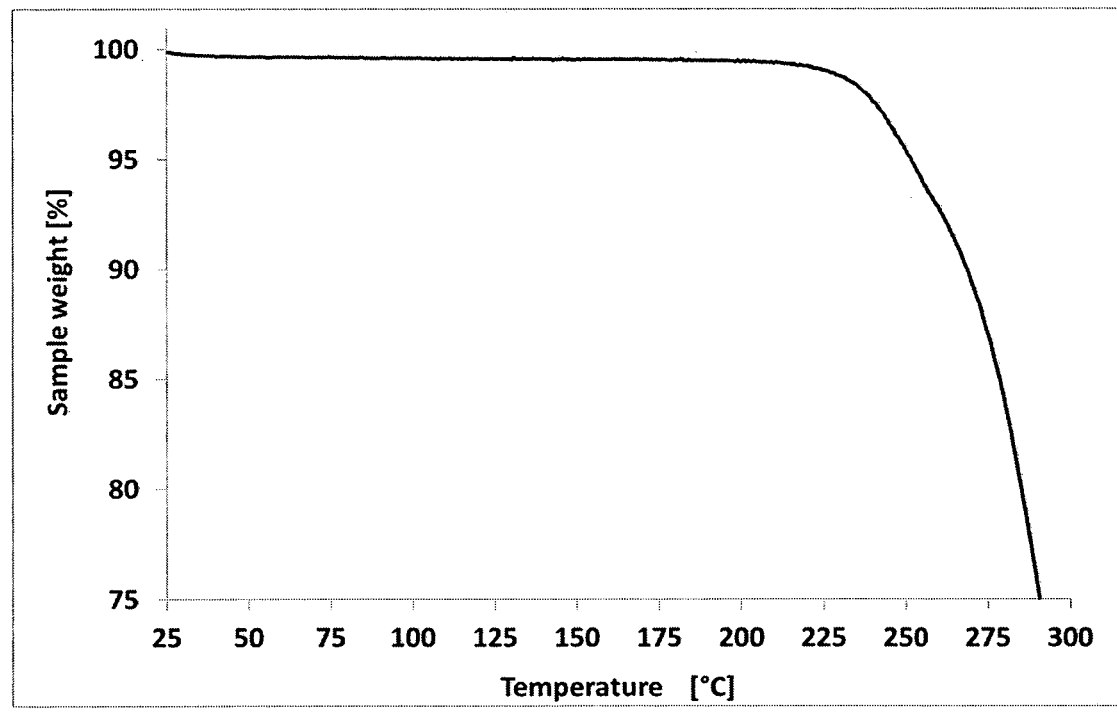
Fig. 4d TGA scan of HCl salt form HCl-A3 (5 K/min)

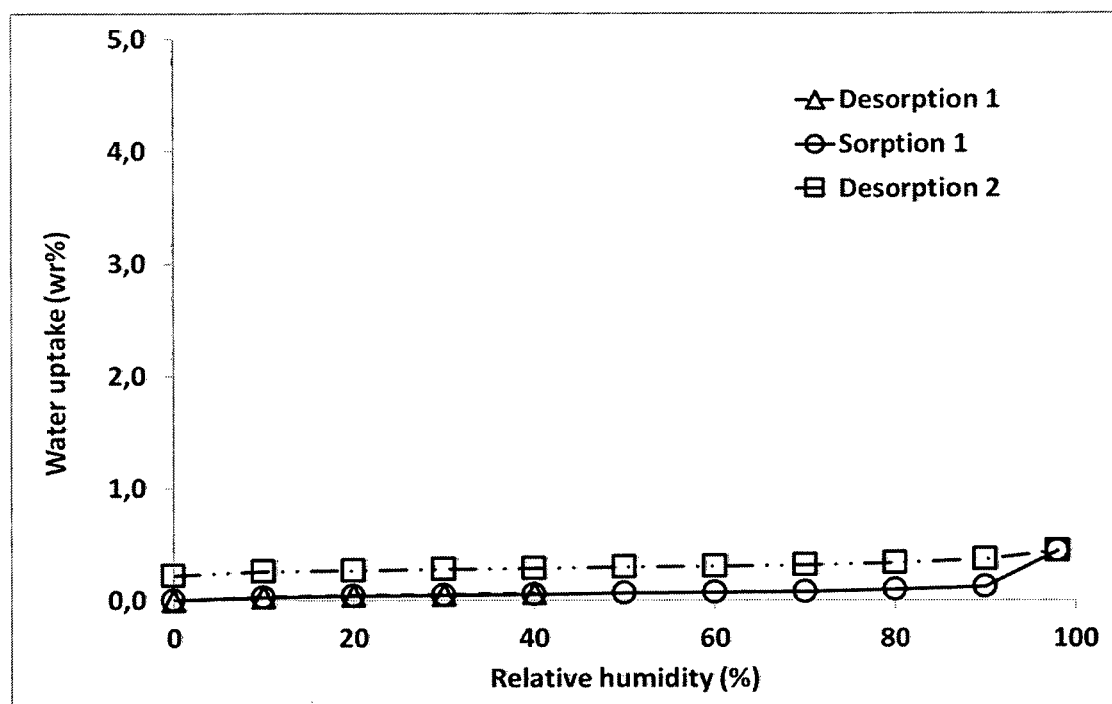
Fig. 4e Water Vapour Sorption Isotherm (25 °C) of HCl salt form HCl-A3

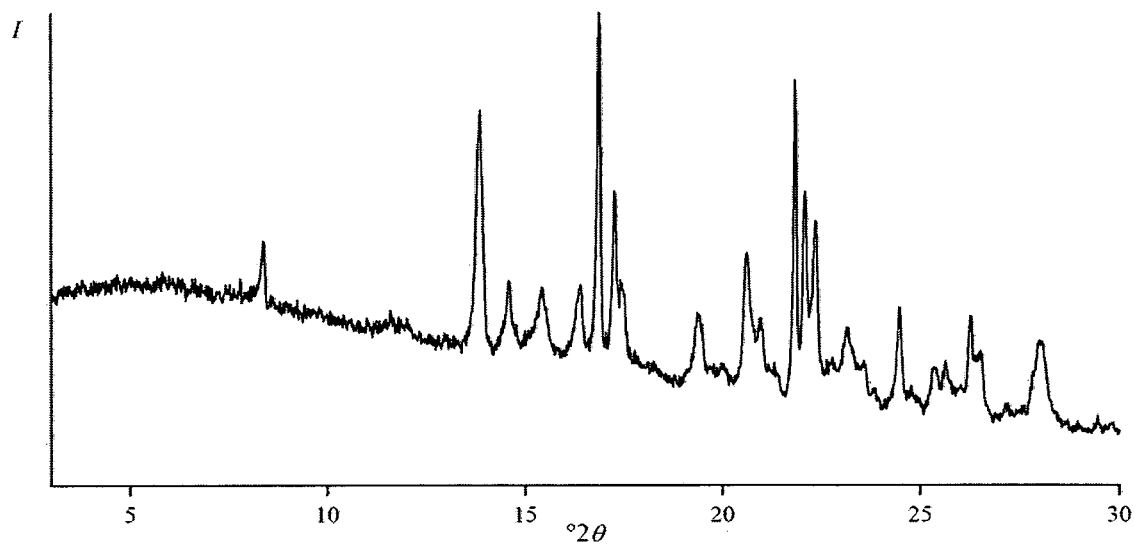
Fig. 5a Powder X-ray diffractogram of Phosphate salt form Phosphate-NF1
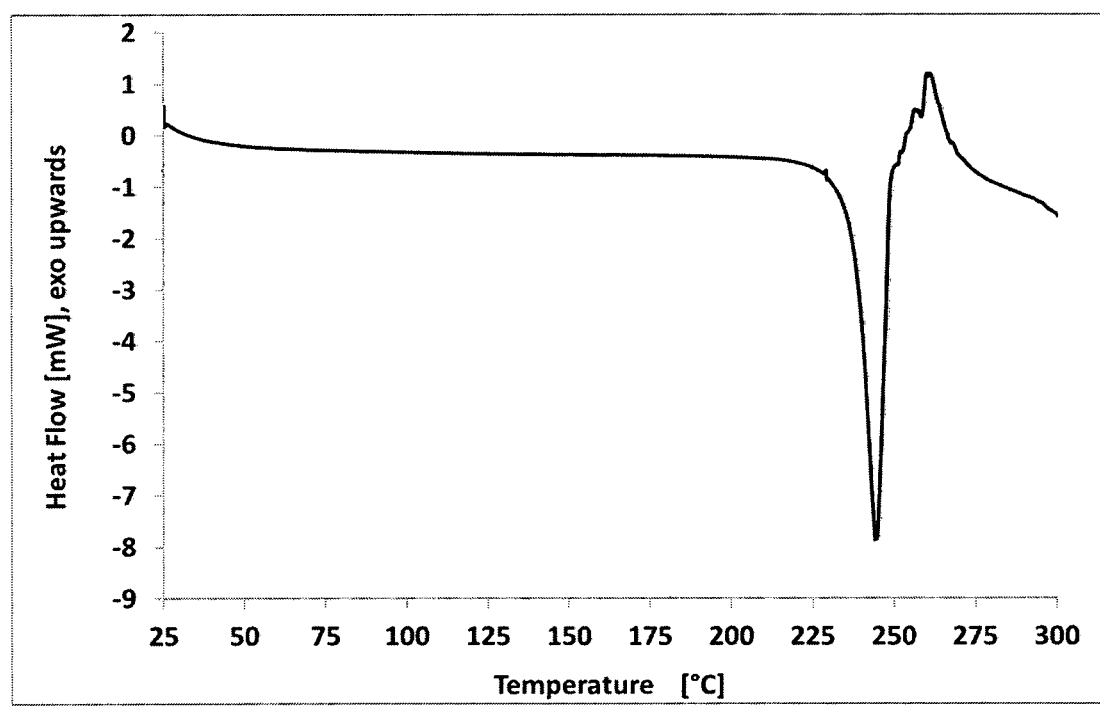
Fig. 5b DSC scan of Phosphate salt form Phosphate-NF1 (5 K/min)

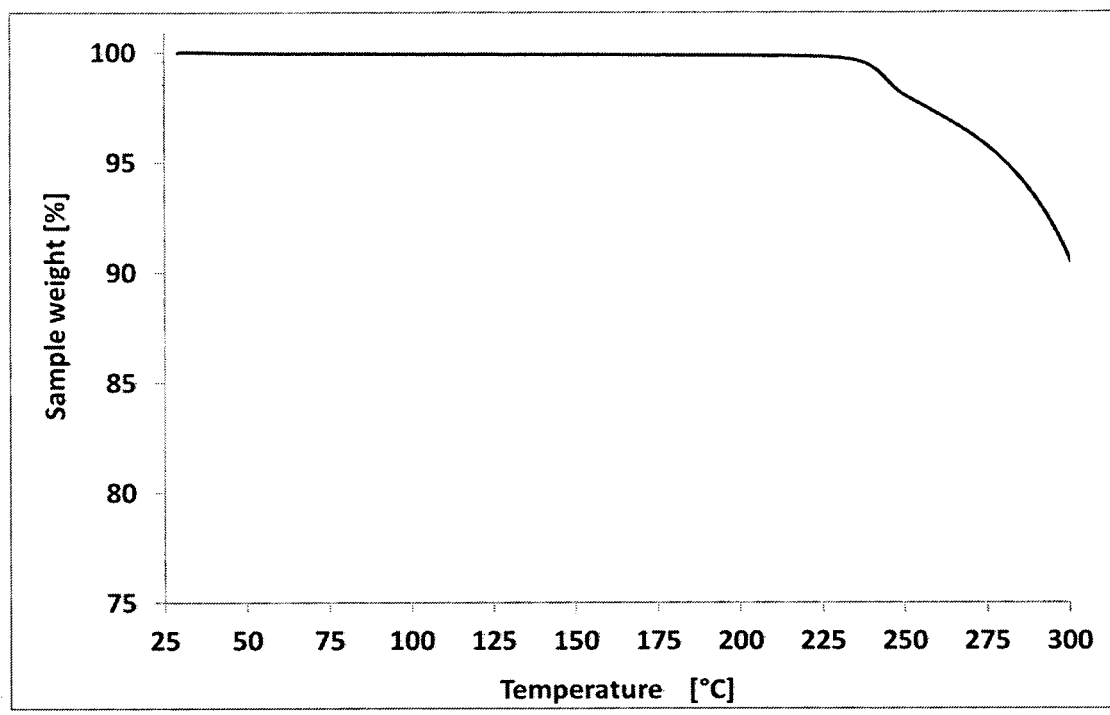
Fig. 5c TGA scan of Phosphate salt form Phosphate-NF1 (5 K/min)
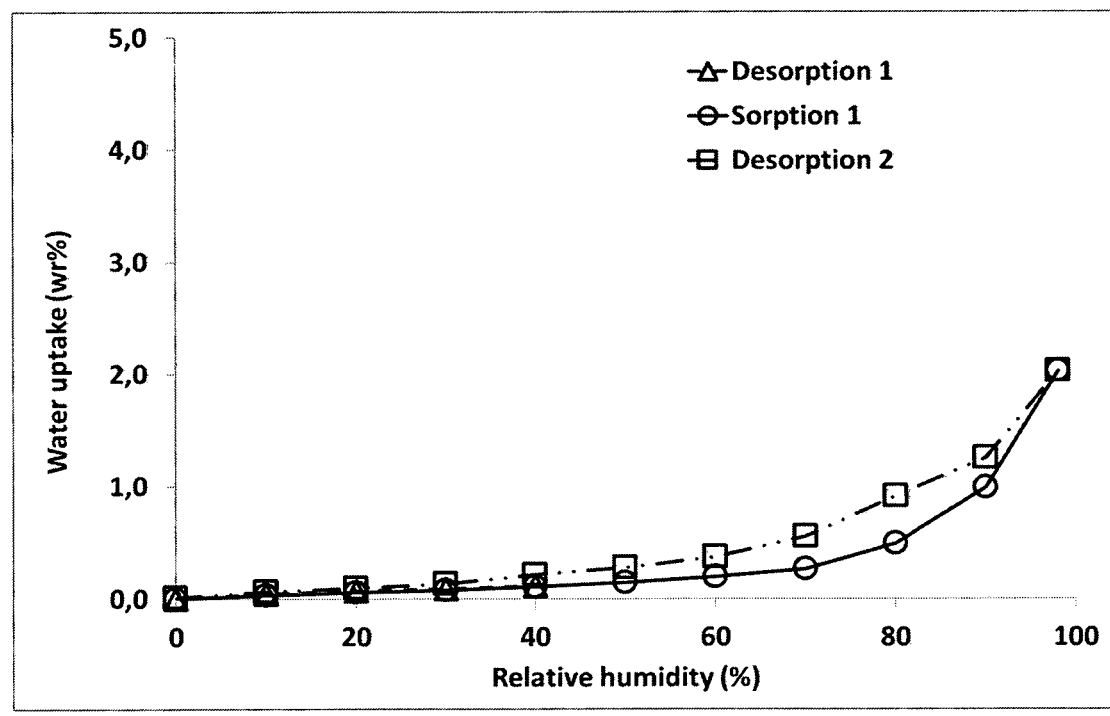
Fig. 5d Water Vapour Sorption Isotherm (25 °C) of Phosphate salt form Phosphate-NF1

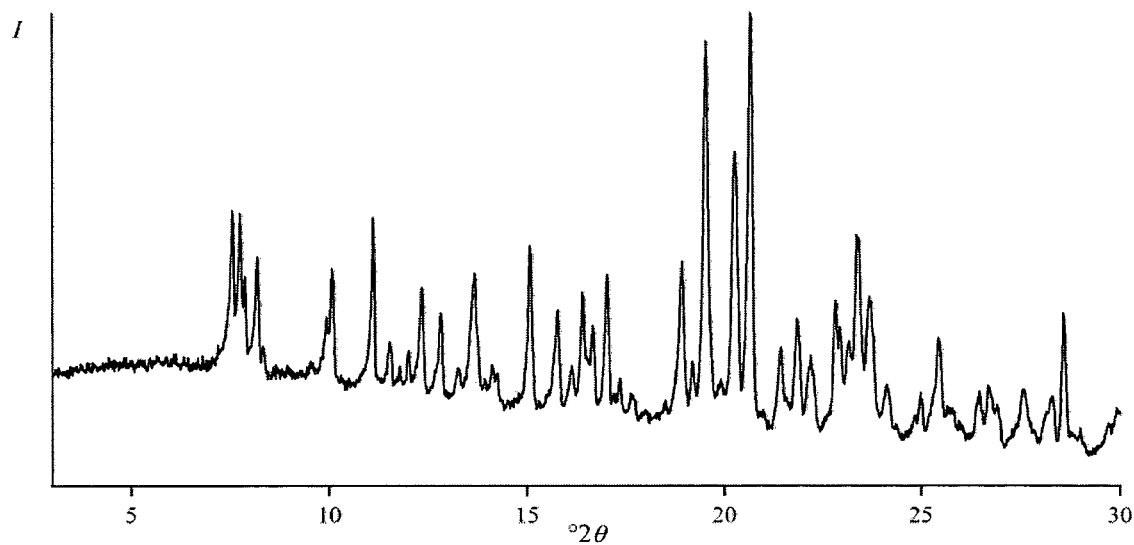
Fig. 6a Powder X-ray diffractogram of Maleate salt form Maleate-NF1
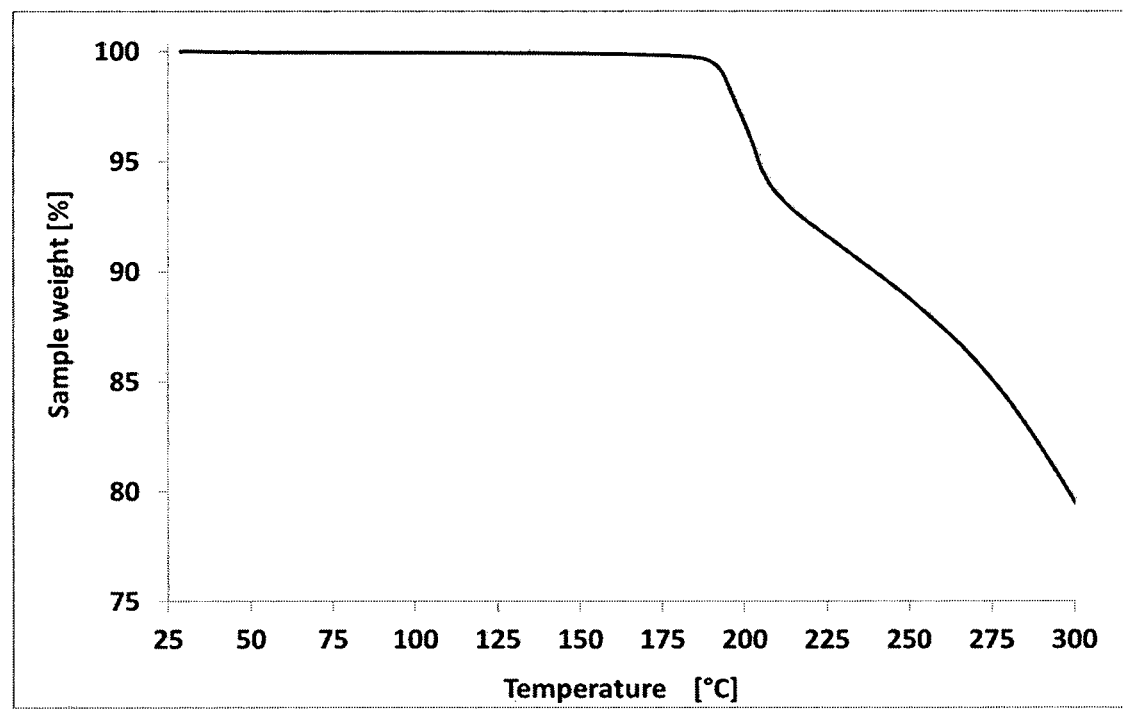
Fig. 6b TGA scan of Maleate salt form Maleate-NF1 (5 K/min)

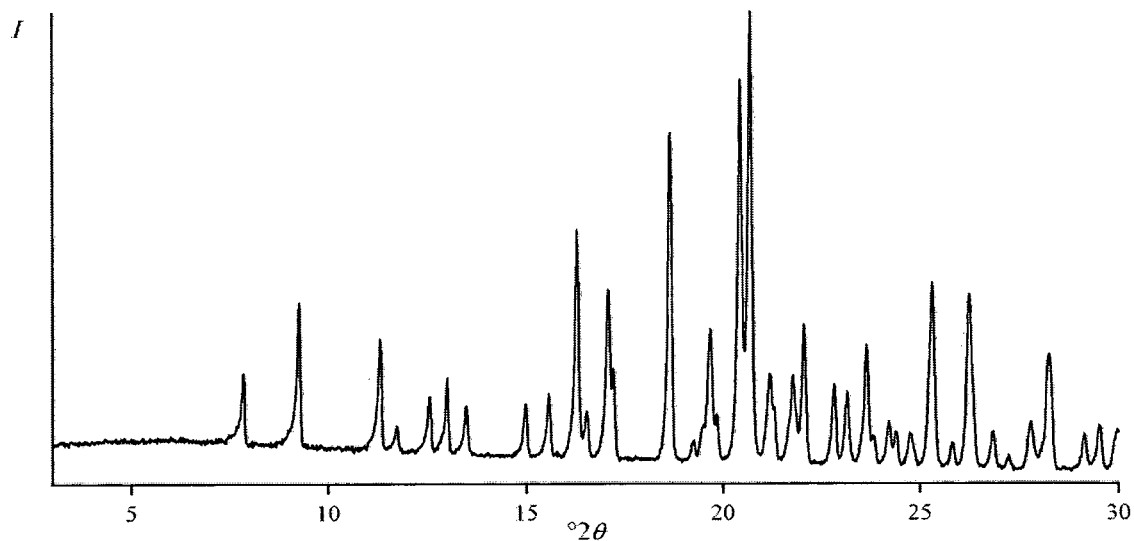
Fig. 7a Powder X-ray diffractogram of Maleate salt form Maleate-NF2
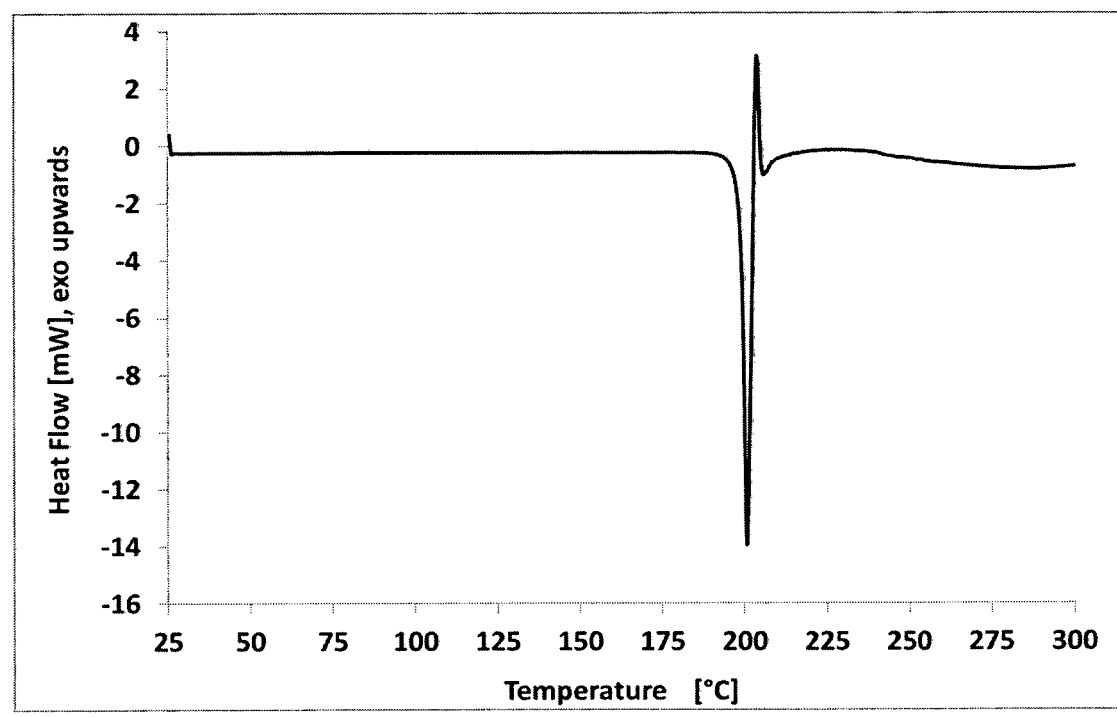
Fig. 7b DSC scan of Maleate salt form Maleate-NF2 (5 K/min)

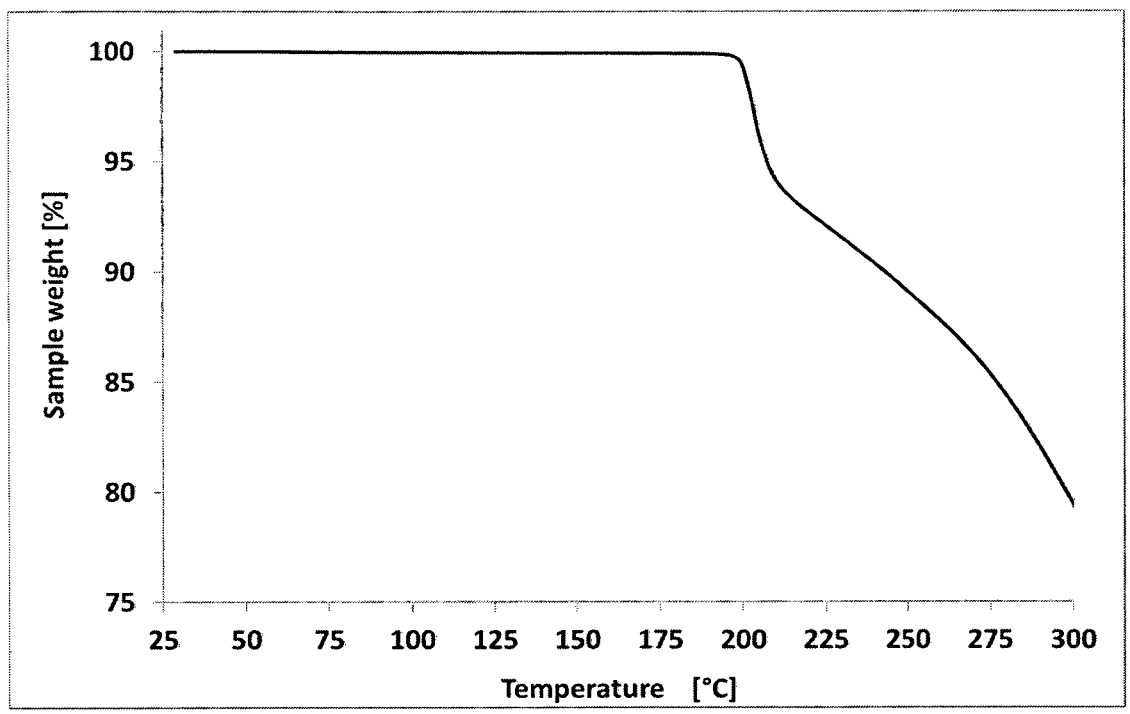
Fig. 7c TGA scan of Maleate salt form Maleate-NF2 (5 K/min)
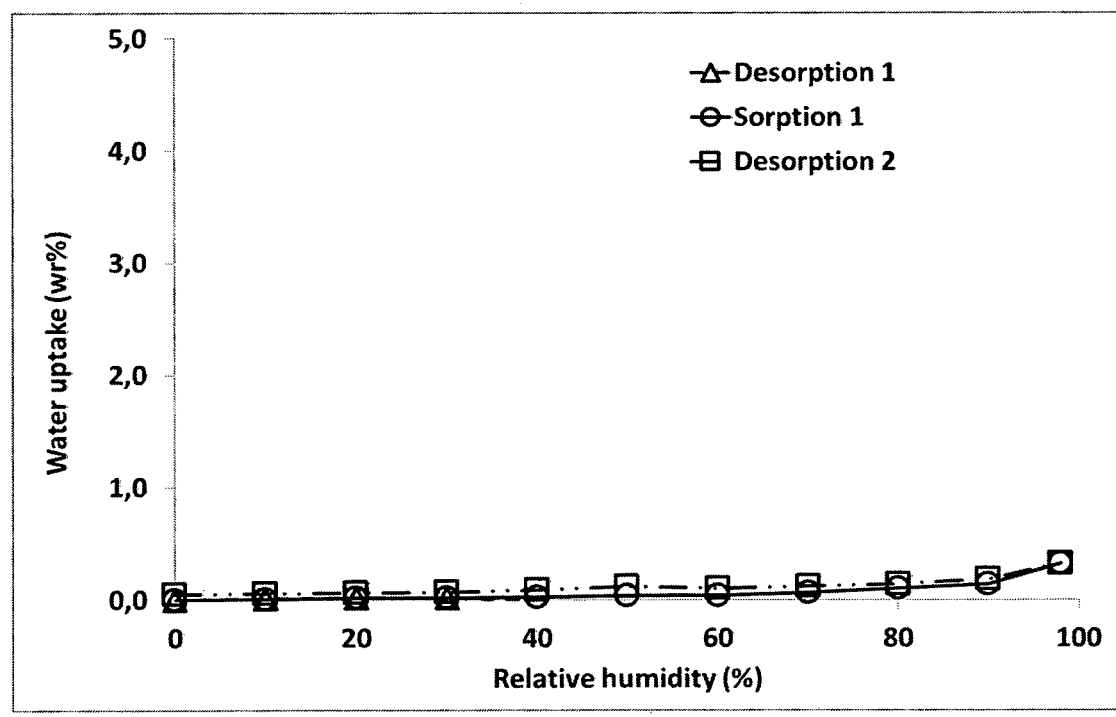
Fig. 7d Water Vapour Sorption Isotherm (25 °C) of Maleate salt form Maleate-NF2

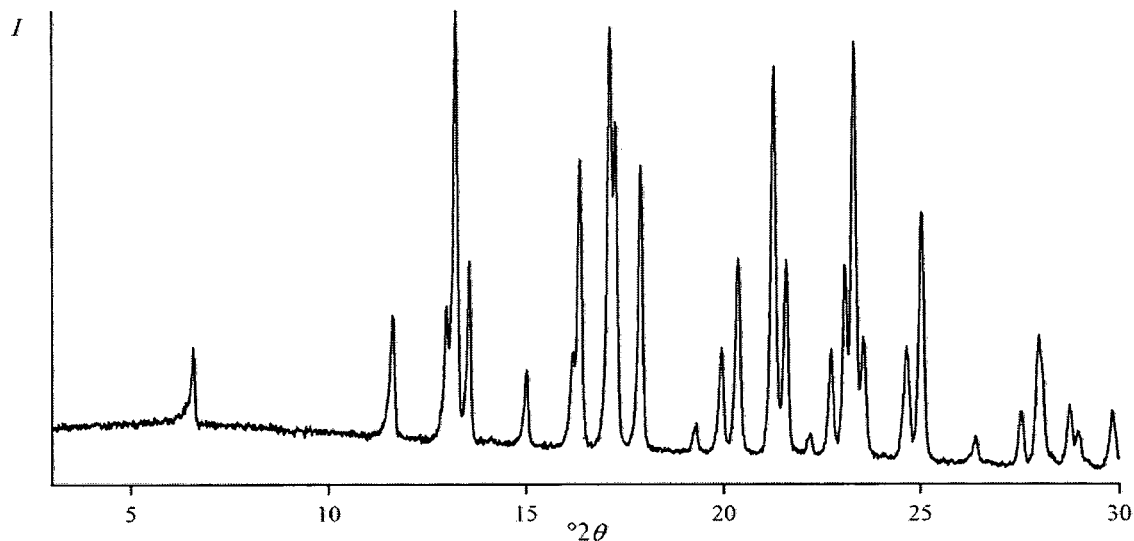
Fig. 8a Powder X-ray diffractogram of Oxalate salt form Oxalate-NF1
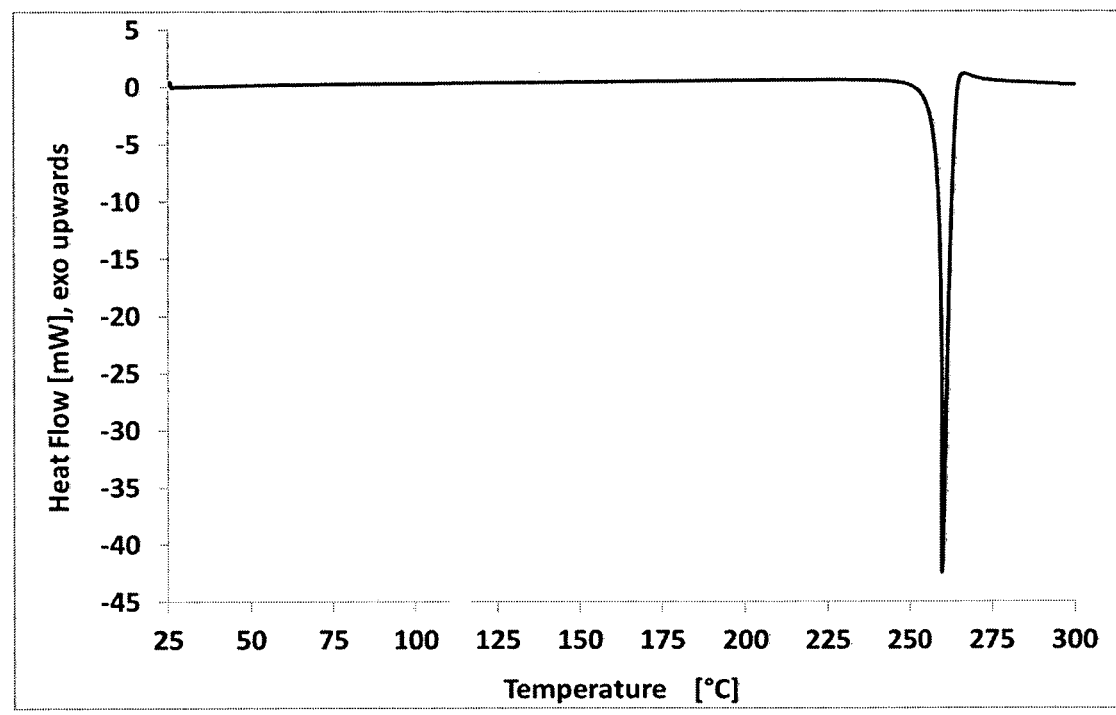
Fig. 8b DSC scan of Oxlate salt form Oxlate-NF1 (5 K/min)

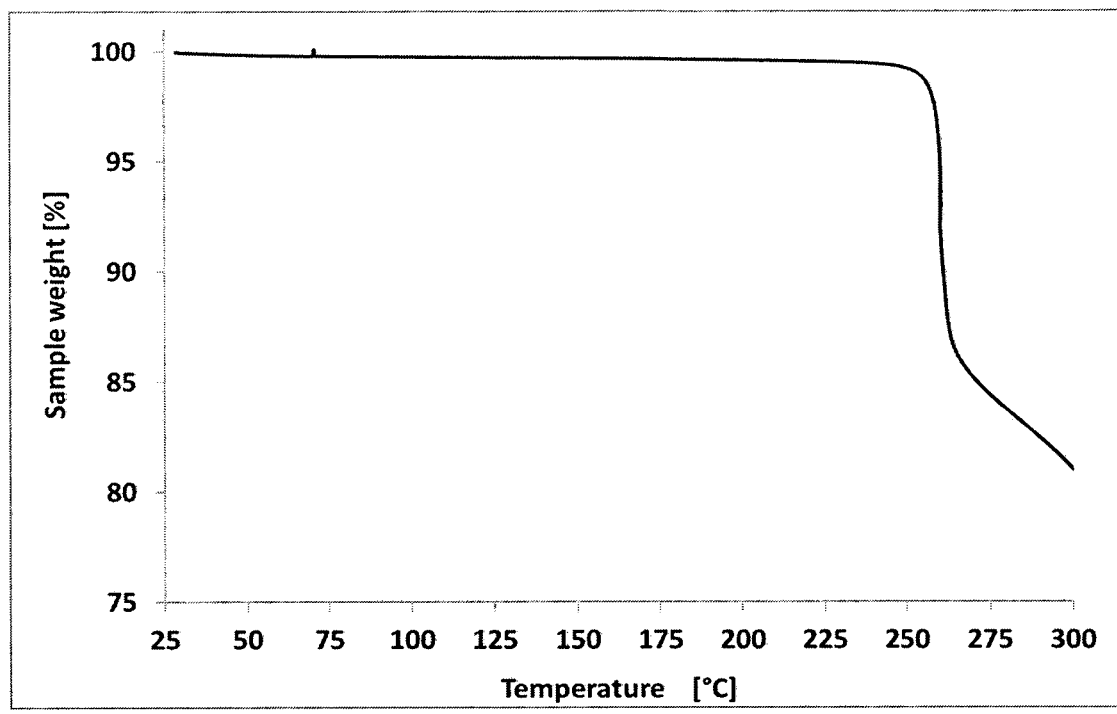
Fig. 8c TGA scan of Oxalate salt form Oxalate-NF1 (5 K/min)

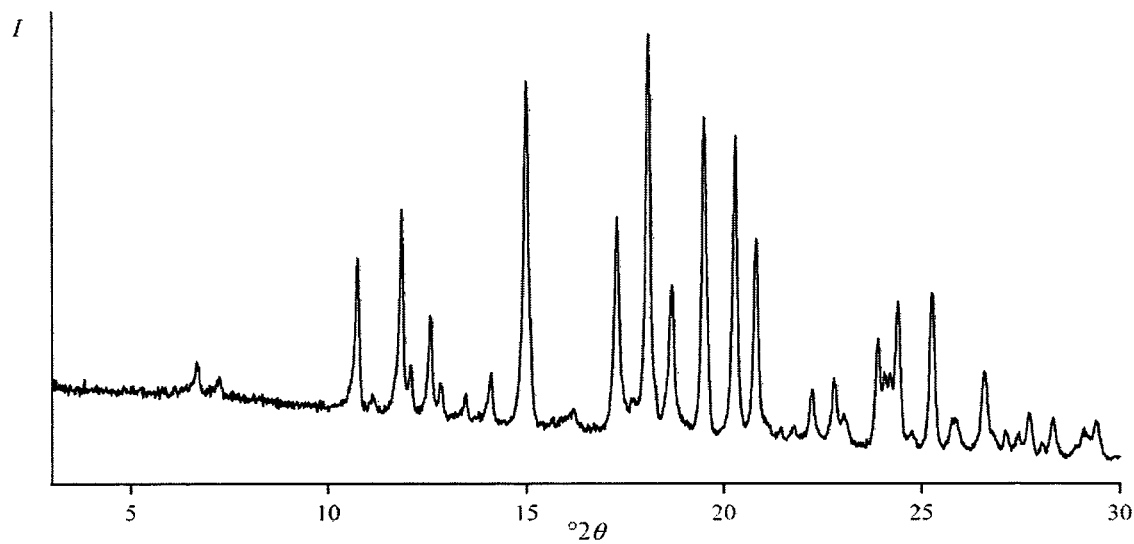
Fig. 9a Powder X-ray diffractogram of Citrate salt form Citrate-NF1
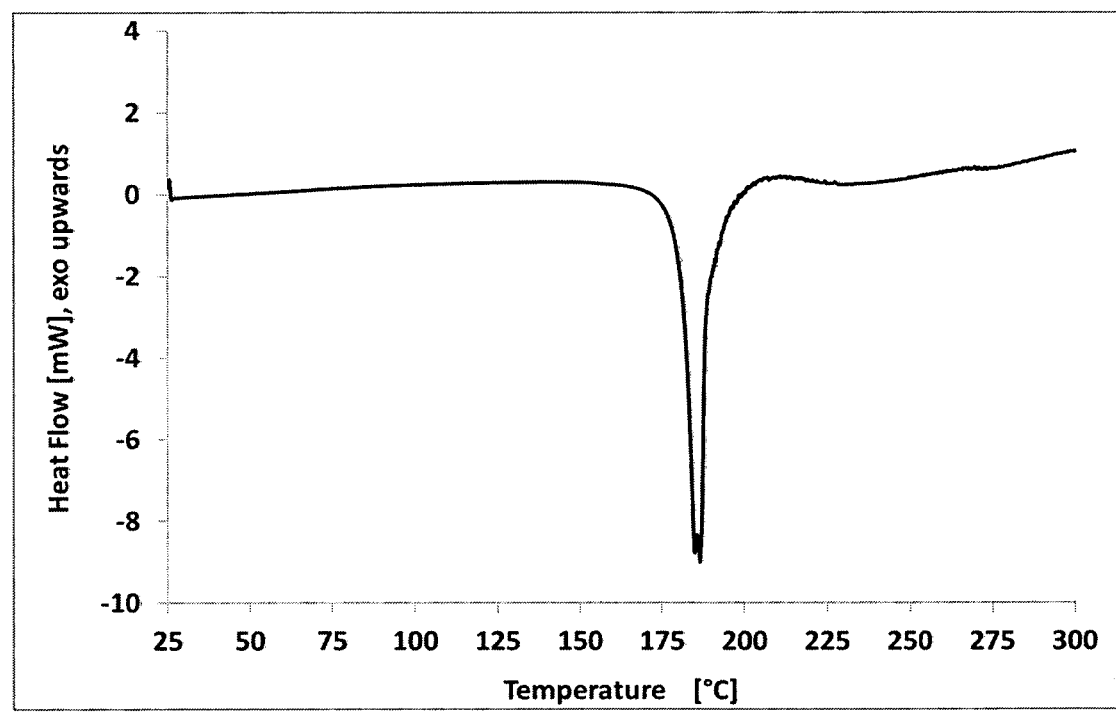
Fig. 9b DSC scan of Citrate salt form Citrate-NF1 (5 K/min)

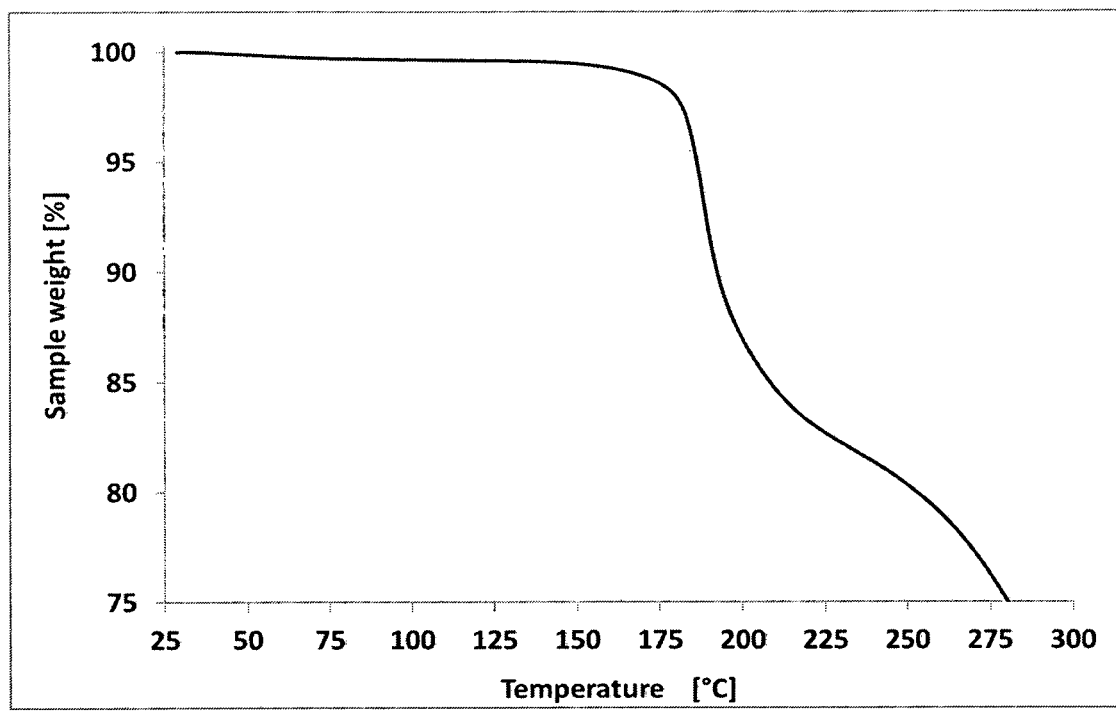
Fig. 9c TGA scan of Citrate salt form Citrate-NF1 (5 K/min)
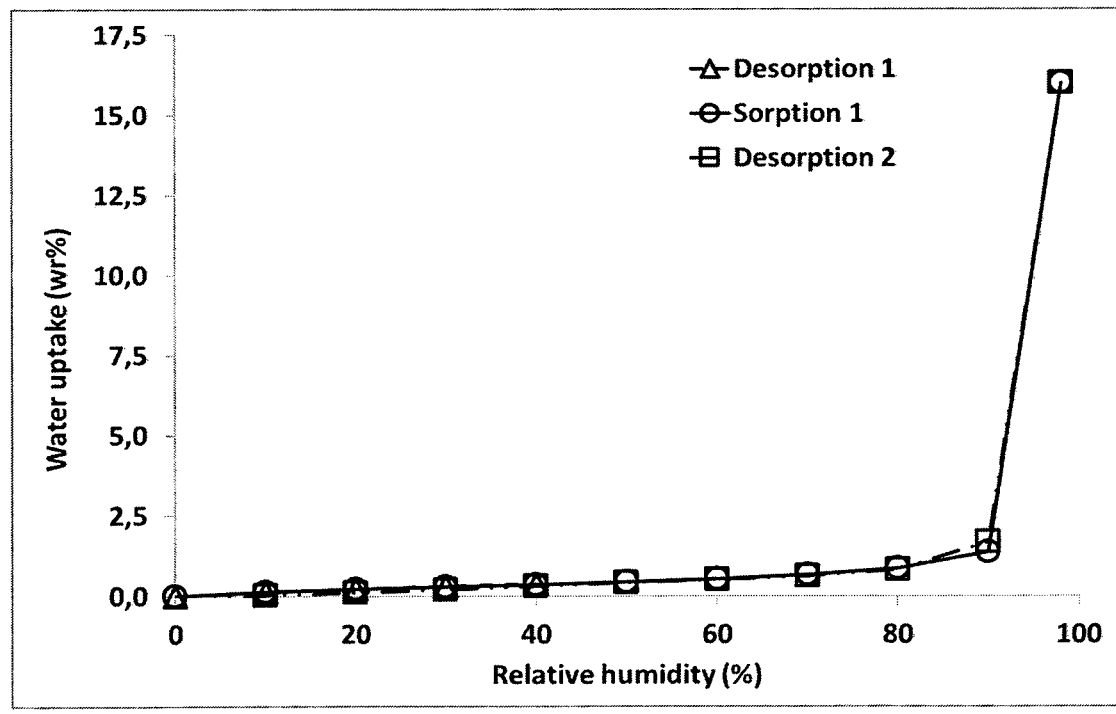
Fig. 9d Water Vapour Sorption Isotherm (25 °C) of Citrate salt form Citrate-NF1

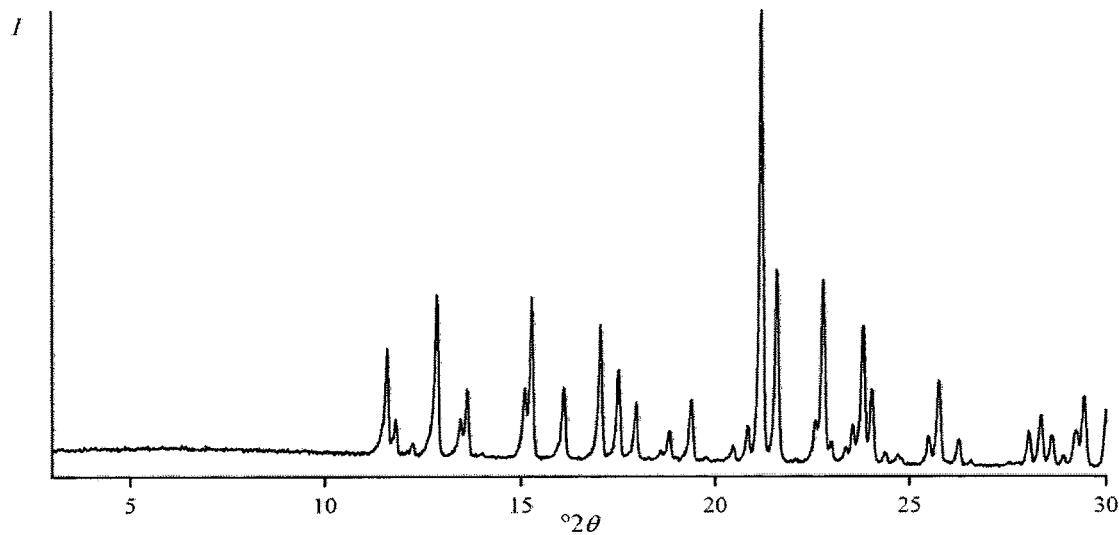
Fig. 10a Powder X-ray diffractogram of Sulfate salt form Sulfate-NF3
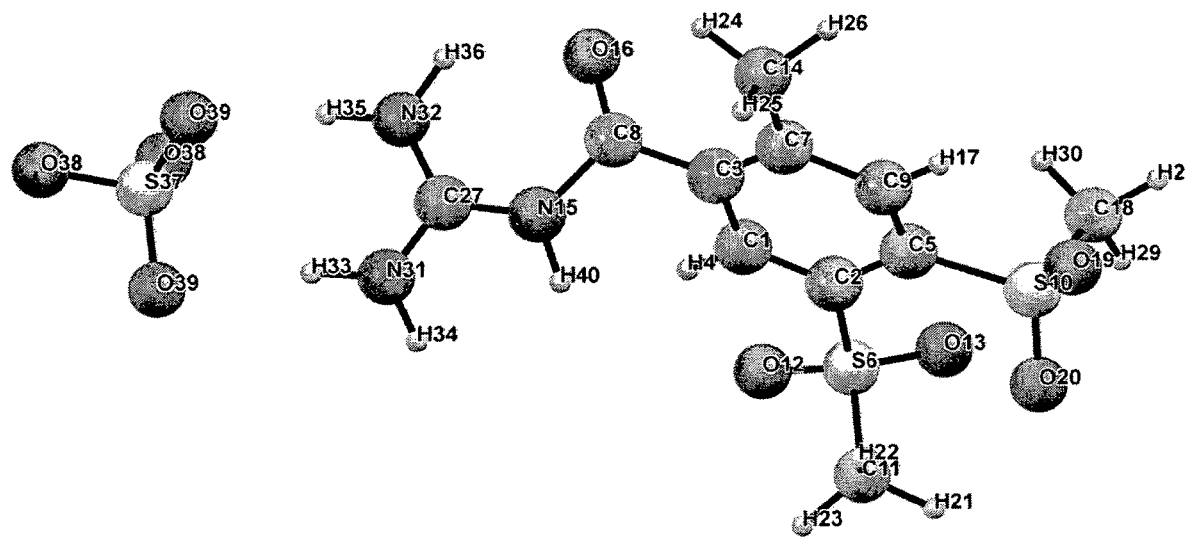
Fig. 10b Crystal structure of Sulfate salt form Sulfate-NF3 viewed approx. along [110]

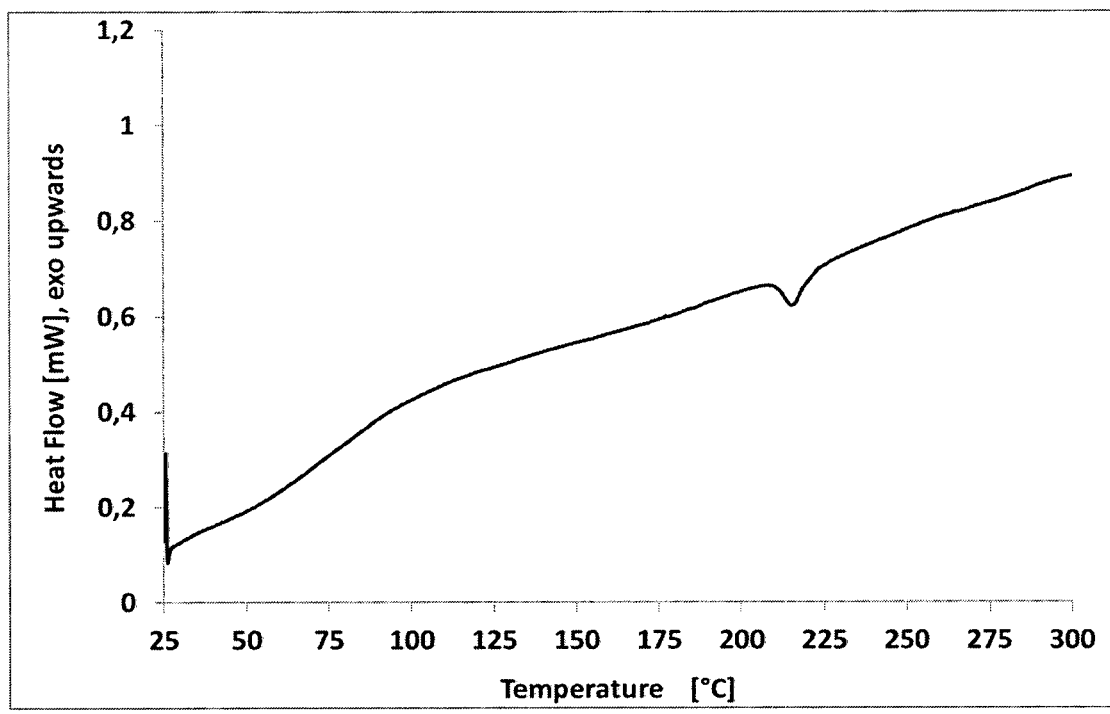
Fig. 10c DSC scan of Sulfate salt form Sulfate-NF3 (5 K/min)
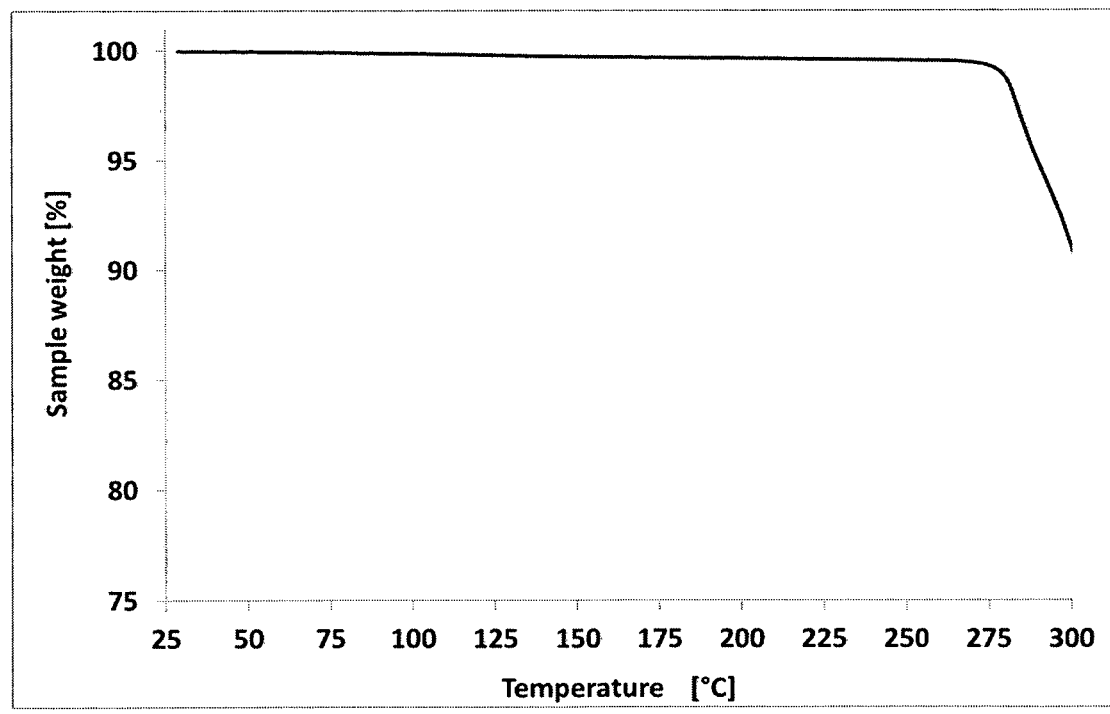
Fig. 10d TGA scan of Sulfate salt form Sulfate-NF3 (5 K/min)

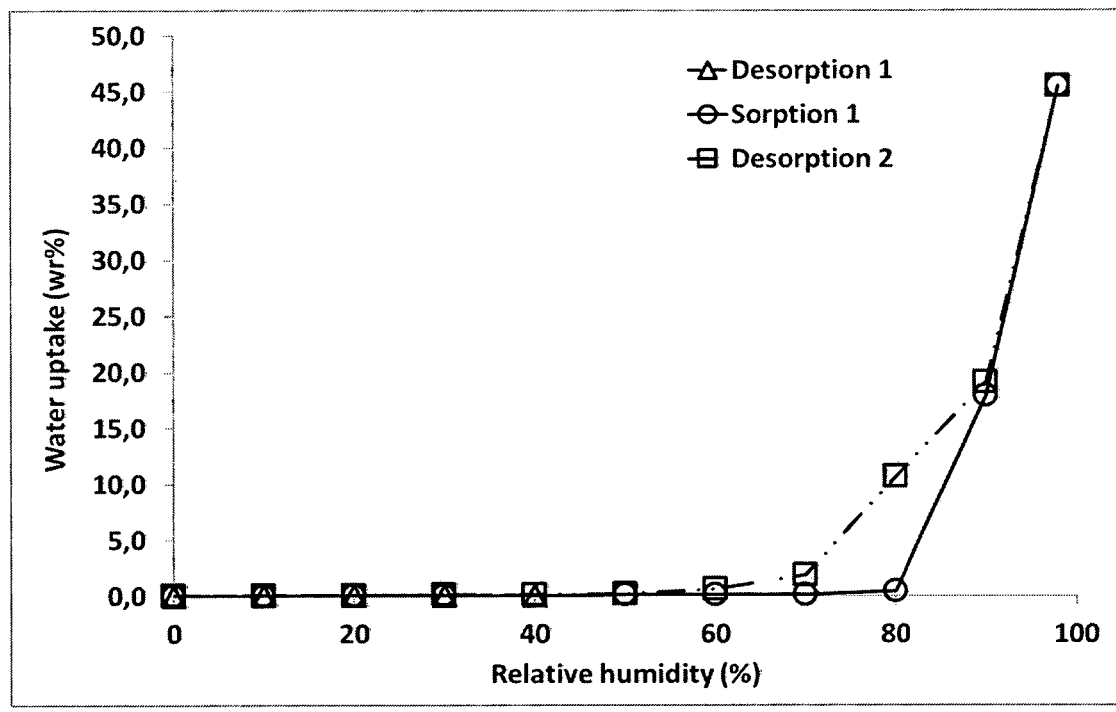
Fig. 10e Water Vapour Sorption Isotherm (25 °C) of Sulfate salt form Sulfate-NF3

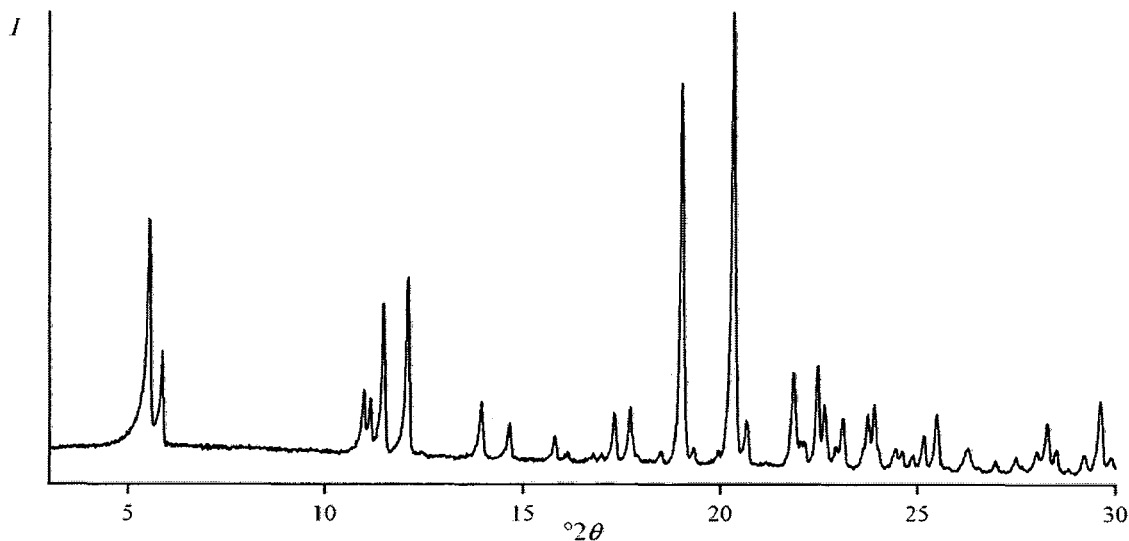
Fig. 11a Powder X-ray diffractogram of Besylate salt form Besylate-NF1
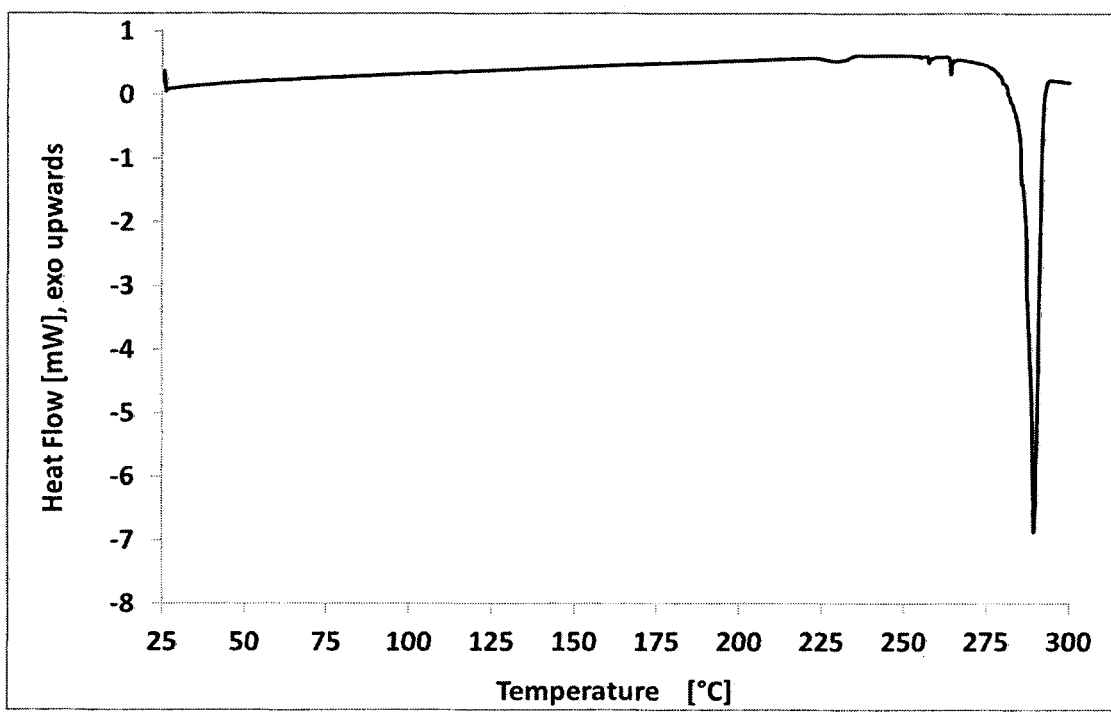
Fig. 11b DSC scan of Besylate salt form Besylate-NF1 (5 K/min)

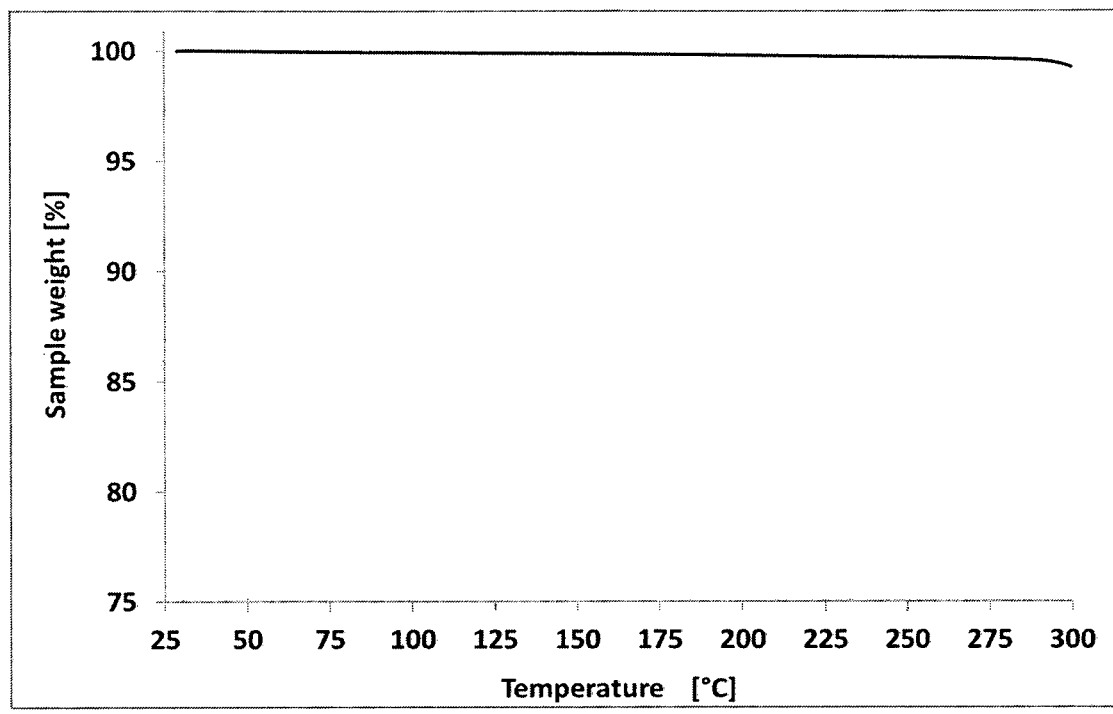
Fig. 11c TGA scan of Besylate salt form Besylate-NF1 (5 K/min)
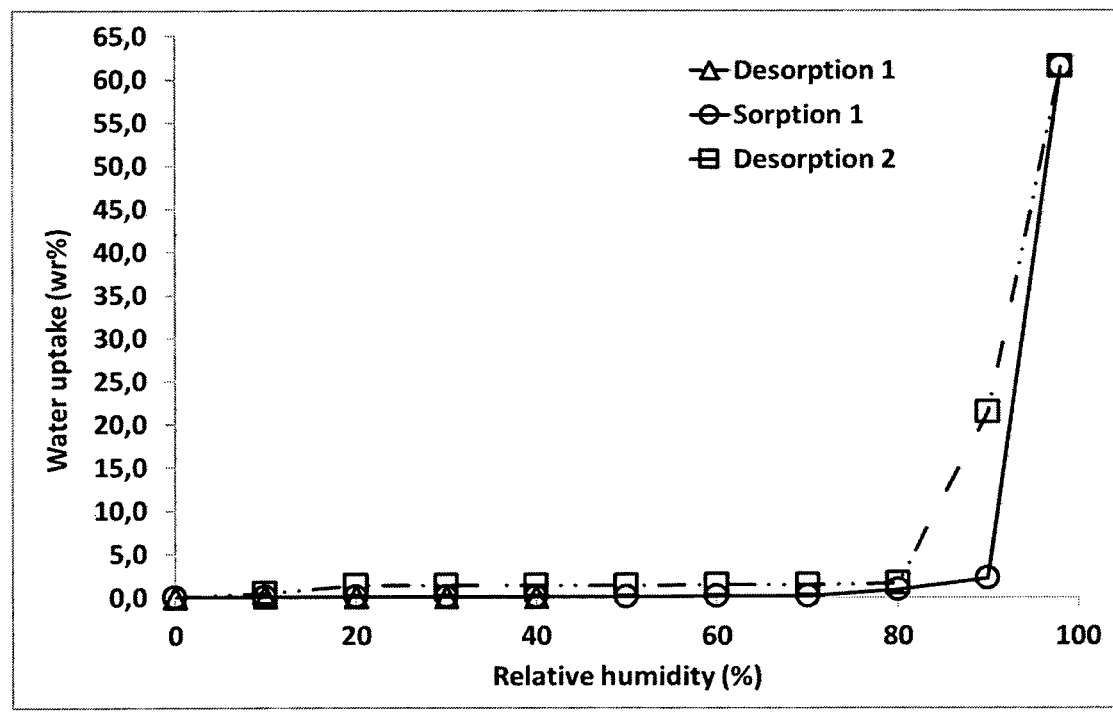
Fig. 11d Water Vapour Sorption Isotherm (25 °C) of Besylate salt form Besylate-NF1

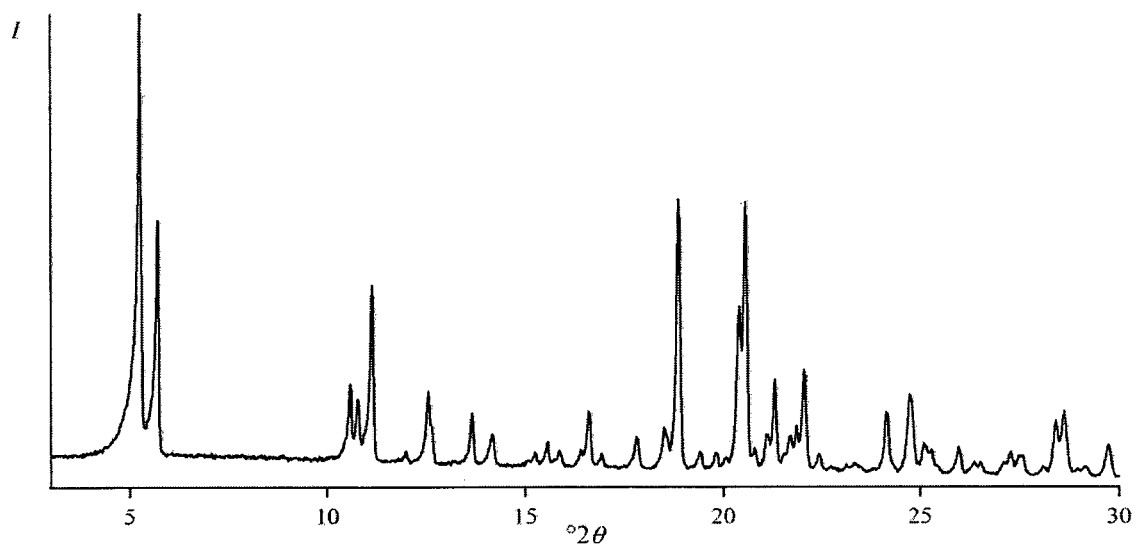
Fig. 12a Powder X-ray diffractogram of p-Tosylate salt form Tosylate-NF1
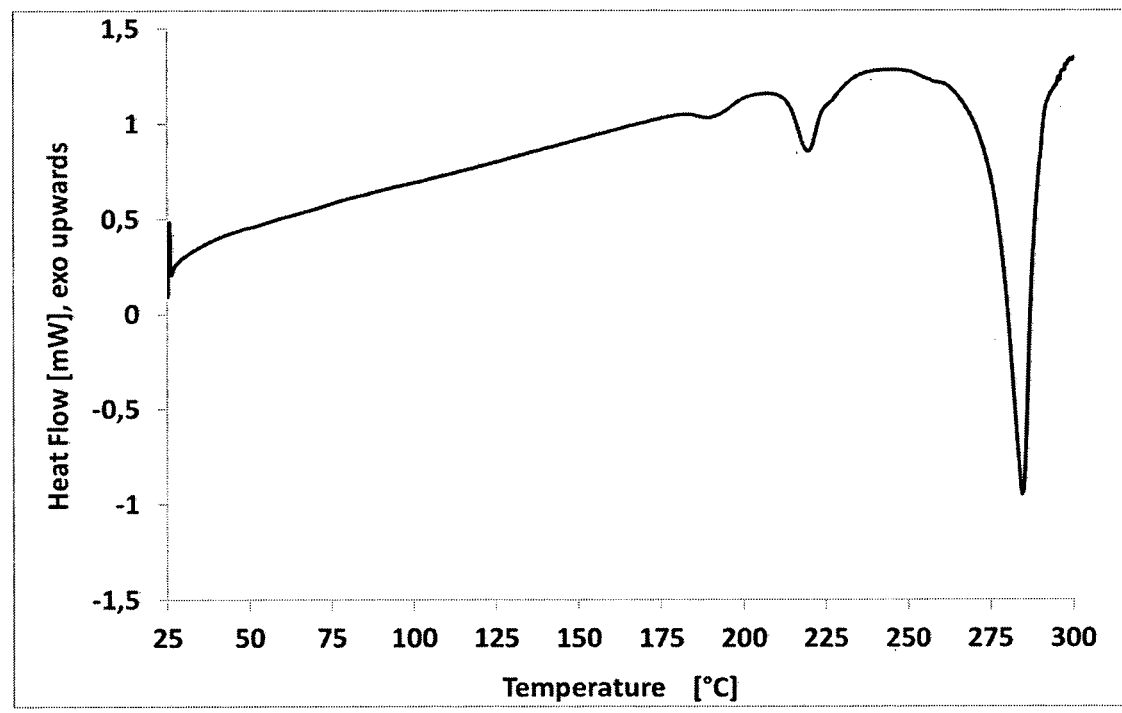
Fig. 12b DSC scan of Tosylate salt form Tosylate-NF1 (5 K/min)

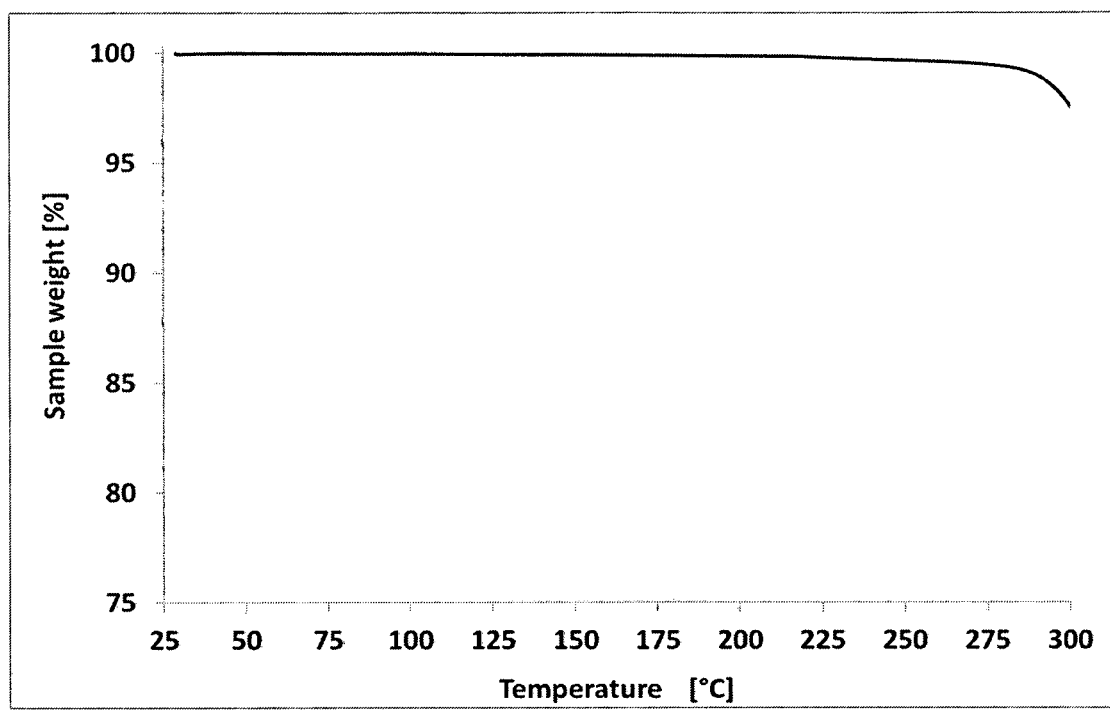
Fig. 12c TGA scan of Tosylate salt form Tosylate-NF1 (5 K/min)
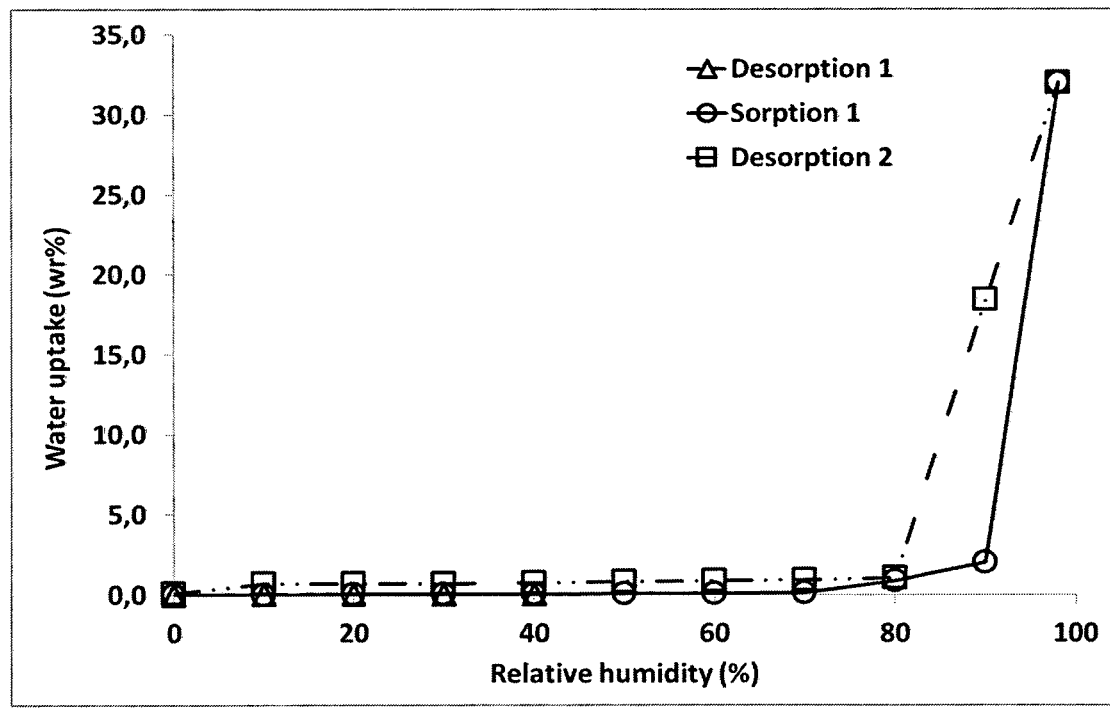
Fig. 12d Water Vapour Sorption Isotherm (25 °C) of Tosylate salt form Tosylate-NF1

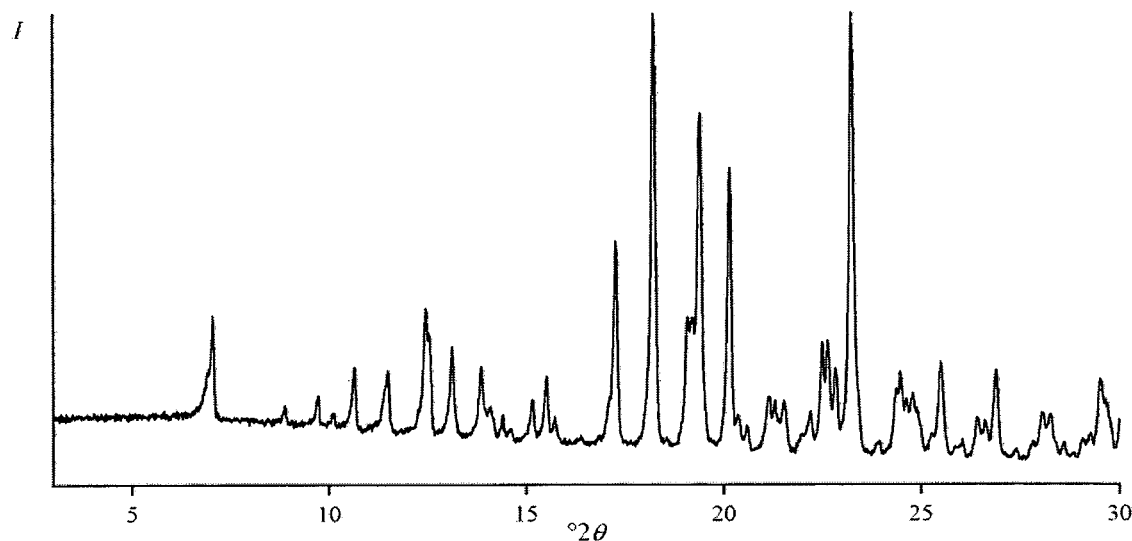
Fig. 13a Powder X-ray diffractogram of Malonate salt form Malonate-NF1
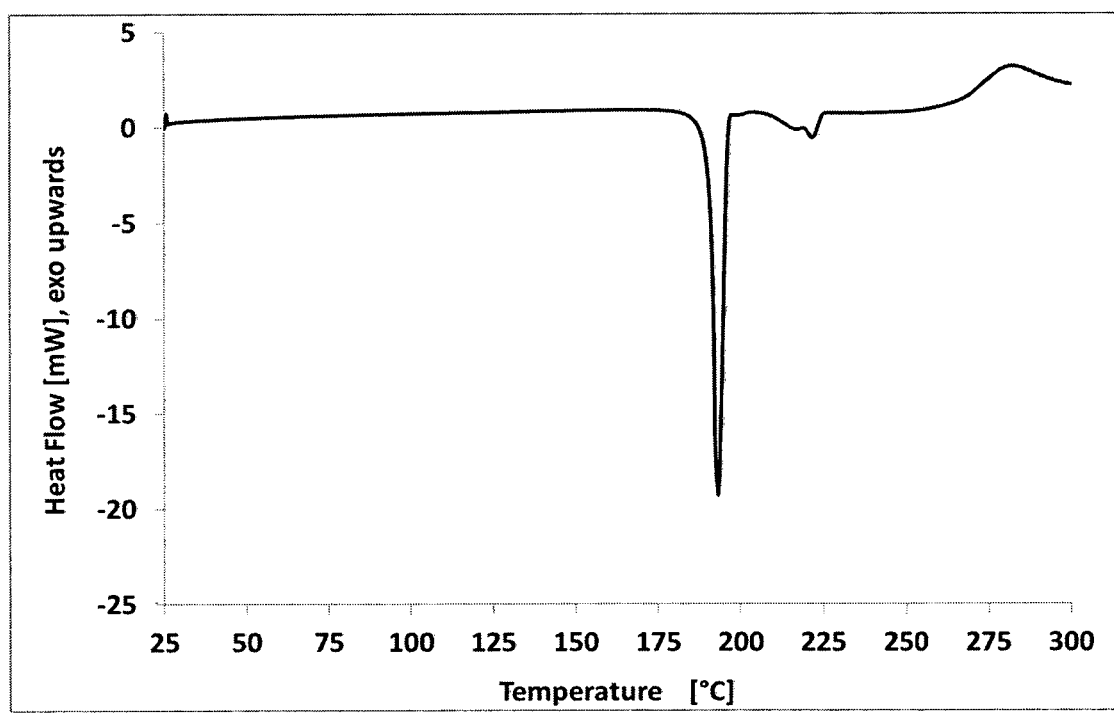
Fig. 13b DSC scan of Malonate salt form Malonate-NF1 (5 K/min)

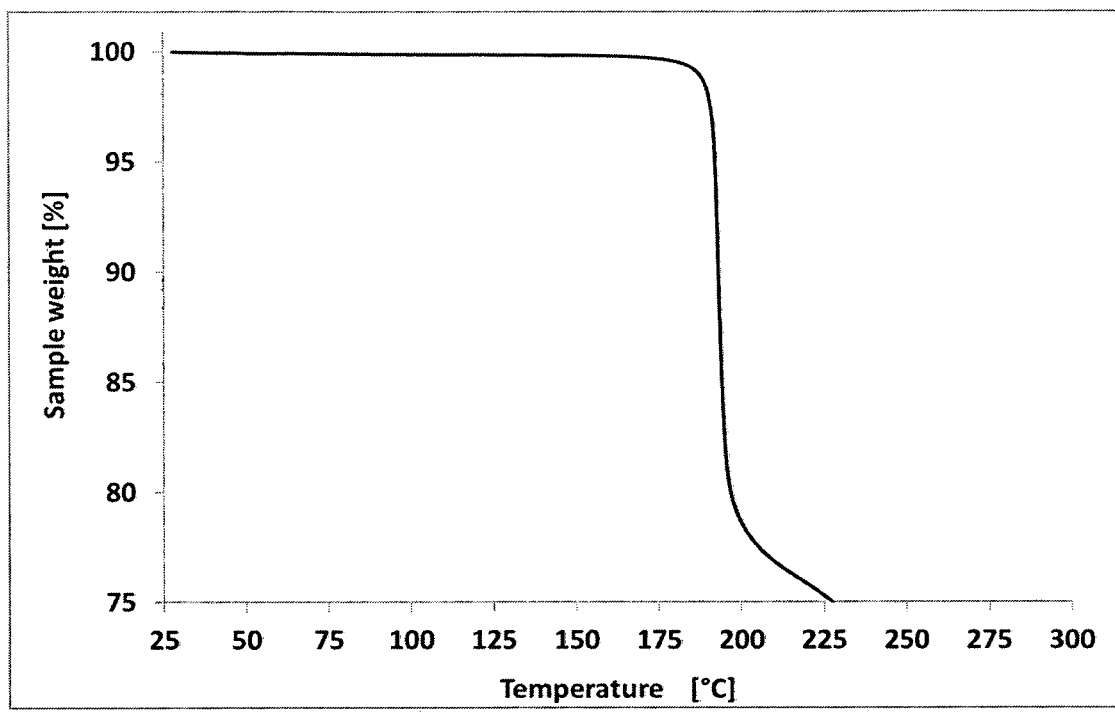
Fig. 13c TGA scan of Malonate salt form Malonate-NF1 (5 K/min)
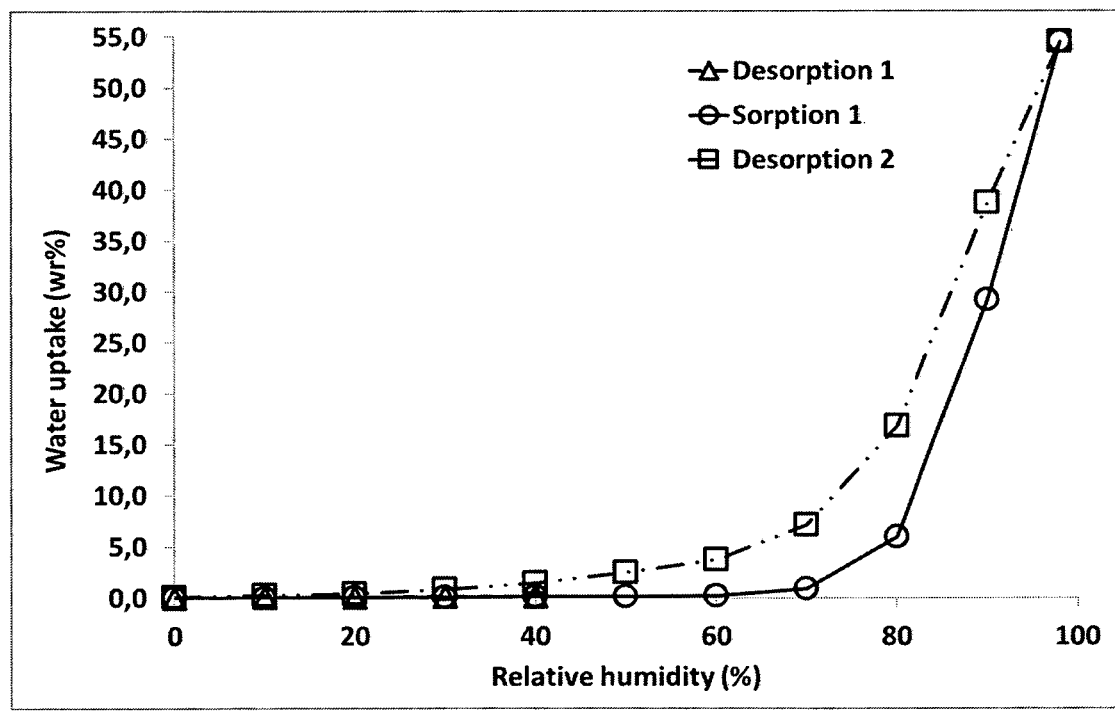
Fig. 13d Water Vapour Sorption Isotherm (25 °C) of Malonate salt form Malonate-NF1

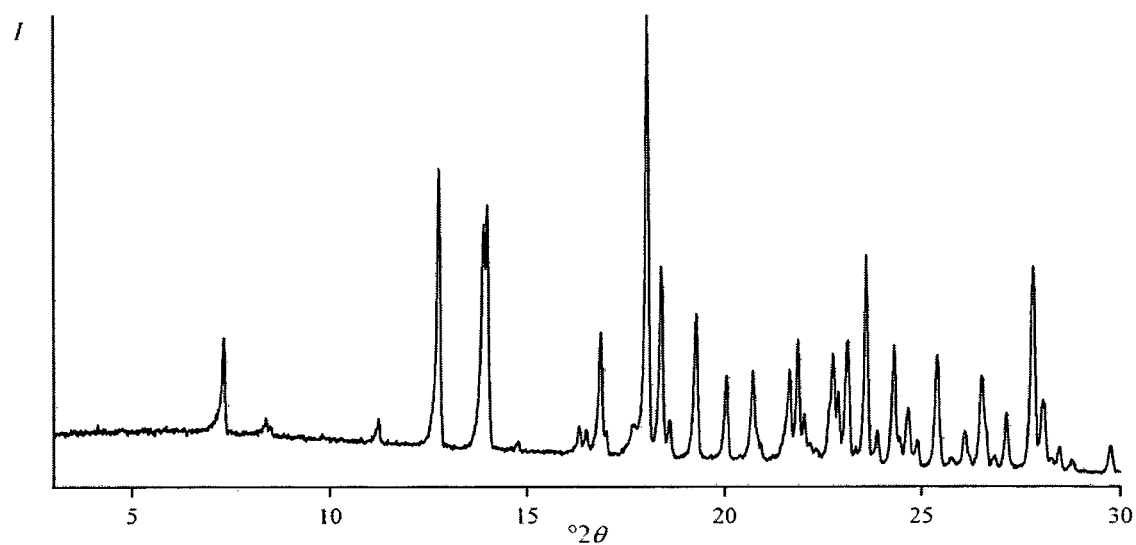
Fig. 14a Powder X-ray diffractogram of Succinate salt form Succinate-NF1

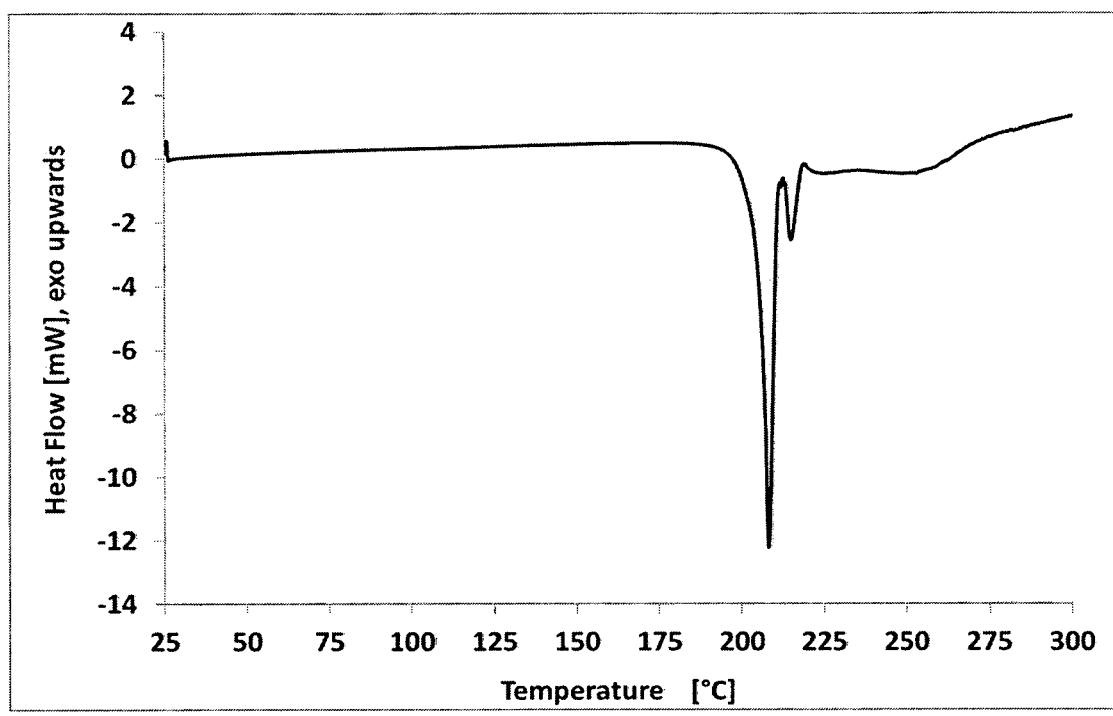
Fig. 14b DSC scan of Succinate salt form Succinate-NF1 (5 K/min)
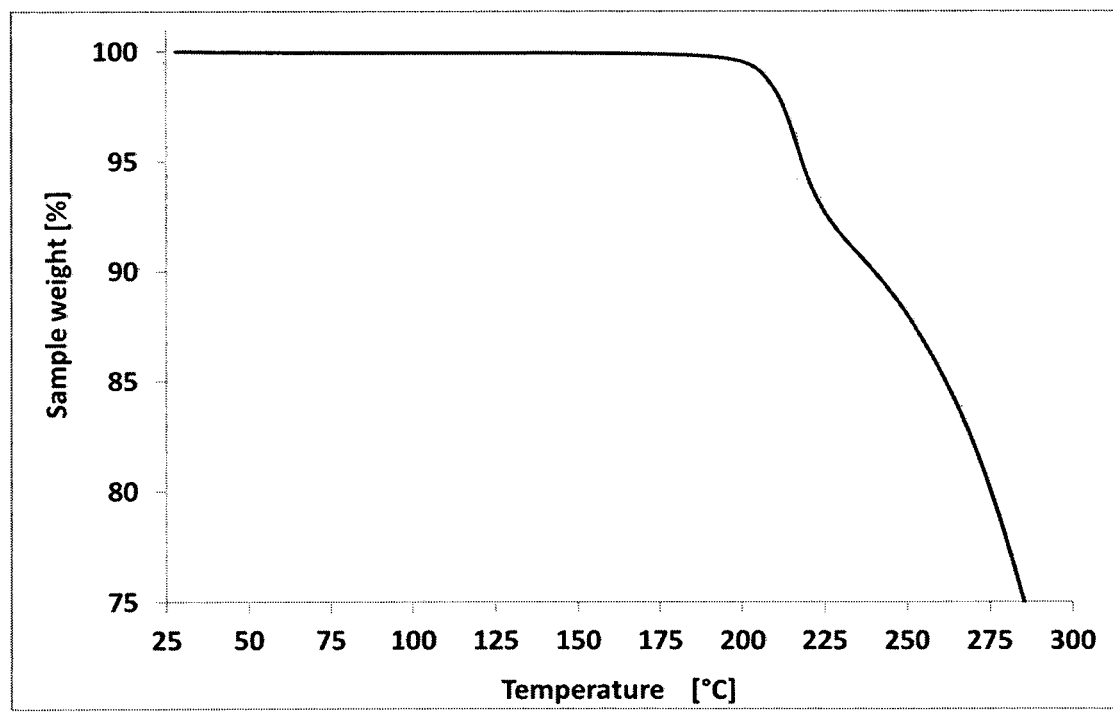
Fig. 14c TGA scan of Succinate salt form Succinate-NF1 (5 K/min)

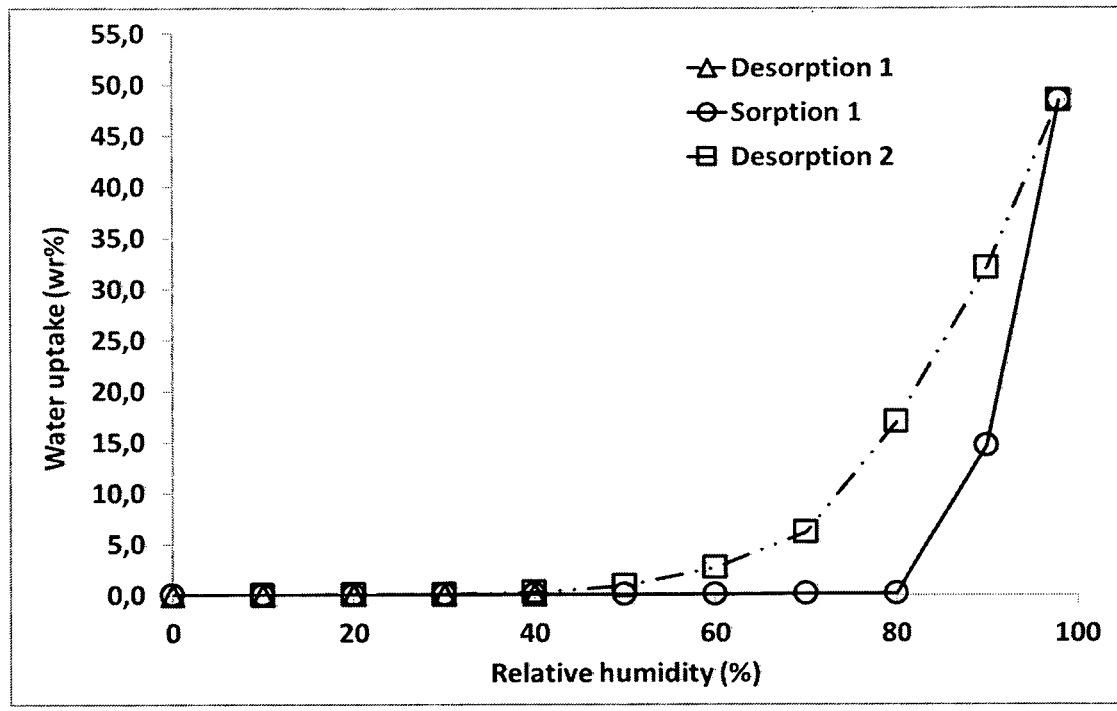
Fig. 14d Water Vapour Sorption Isotherm (25 °C) of Succinate salt form Succinate-NF1

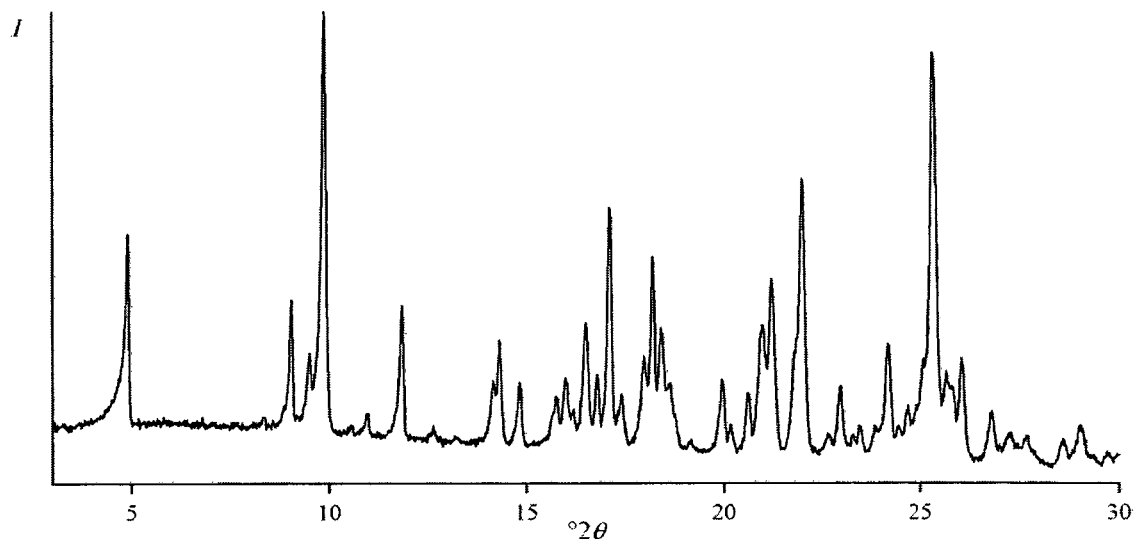
Fig. 15a Powder X-ray diffractogram of Fumarate salt form Fumarate-NF1
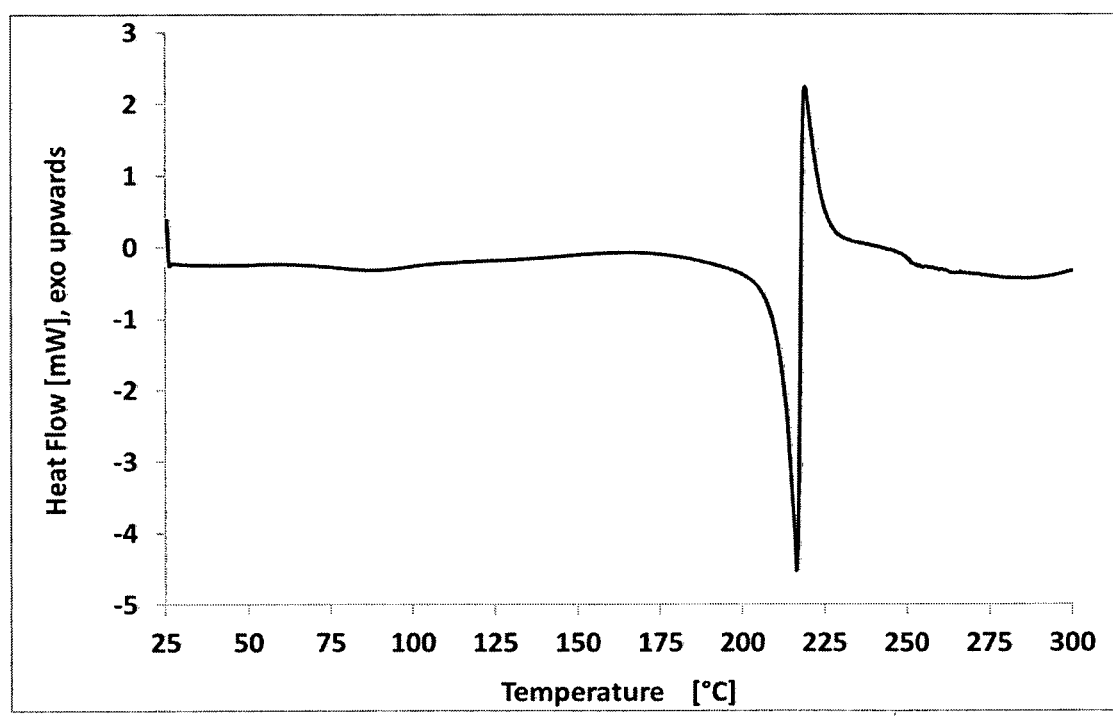
Fig. 15b DSC scan of Fumarate salt form Fumarate-NF1 (5 K/min)

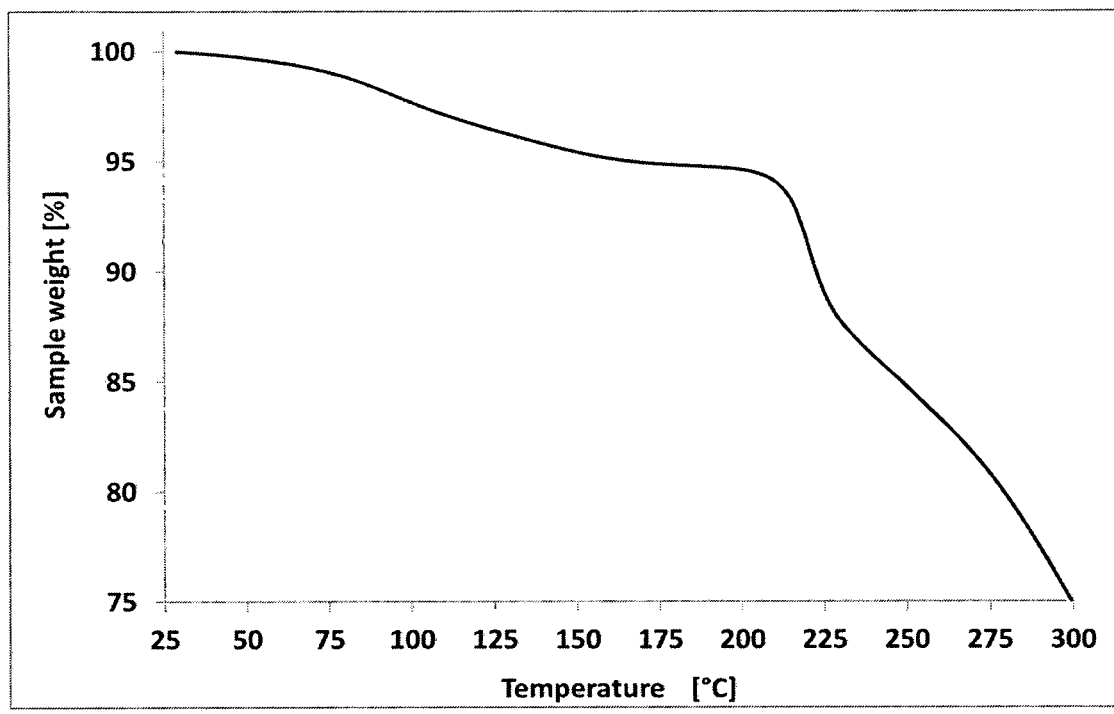
Fig. 15c TGA scan of Fumarate salt form Fumarate-NF1 (5 K/min)
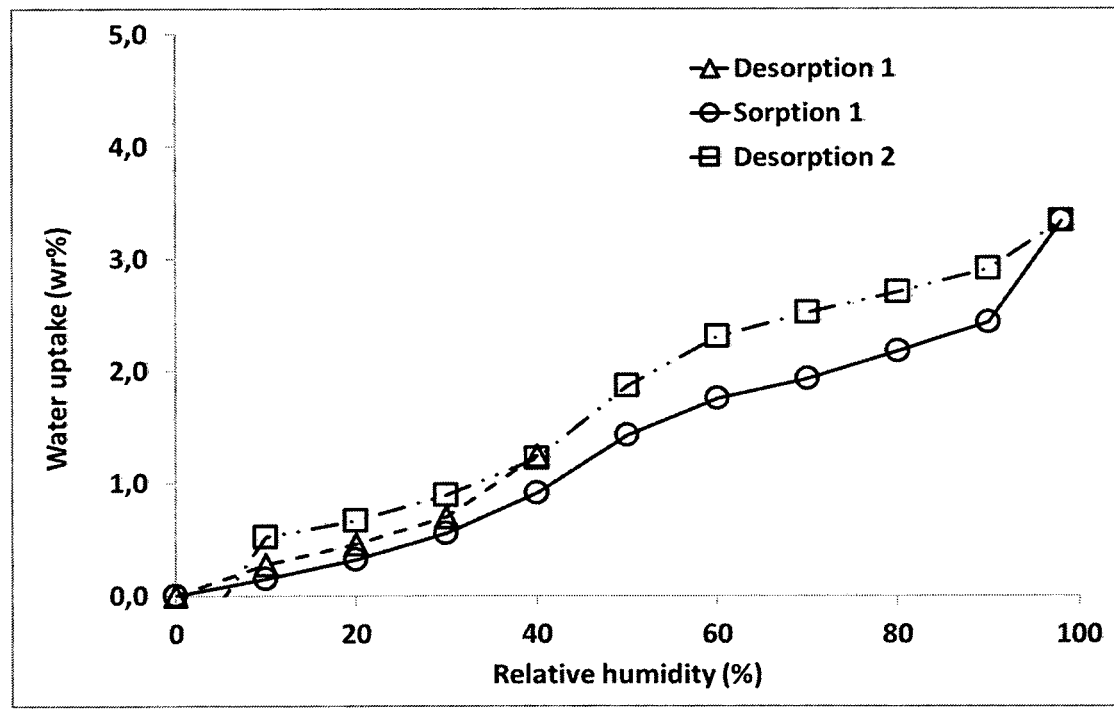
Fig. 15d Water Vapour Sorption Isotherm (25 °C) of Fumarate salt form Fumarate-NF1

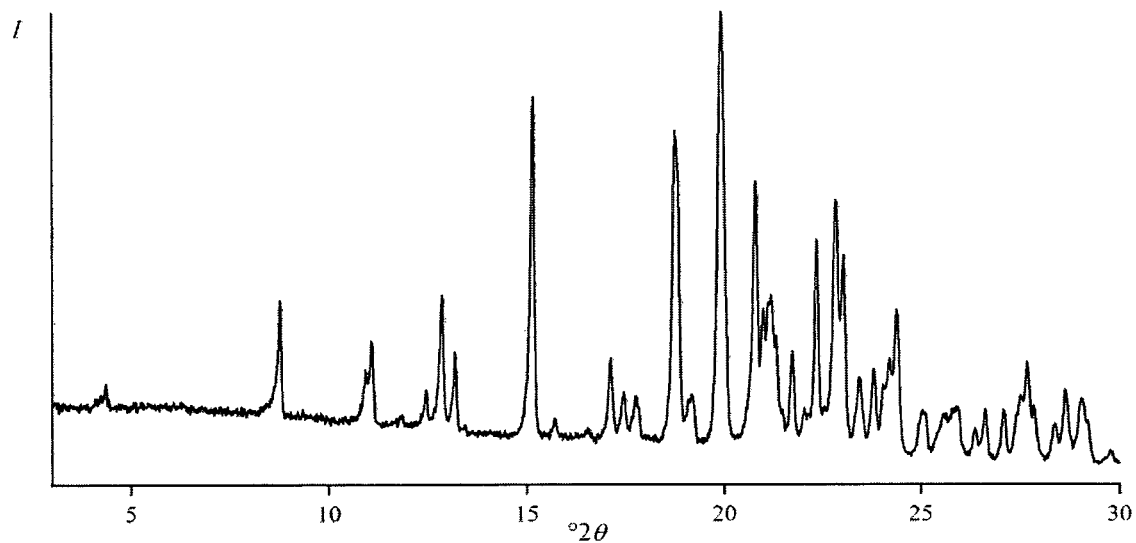
Fig. 16a Powder X-ray diffractogram of Tartrate salt form Tartrate-NF1
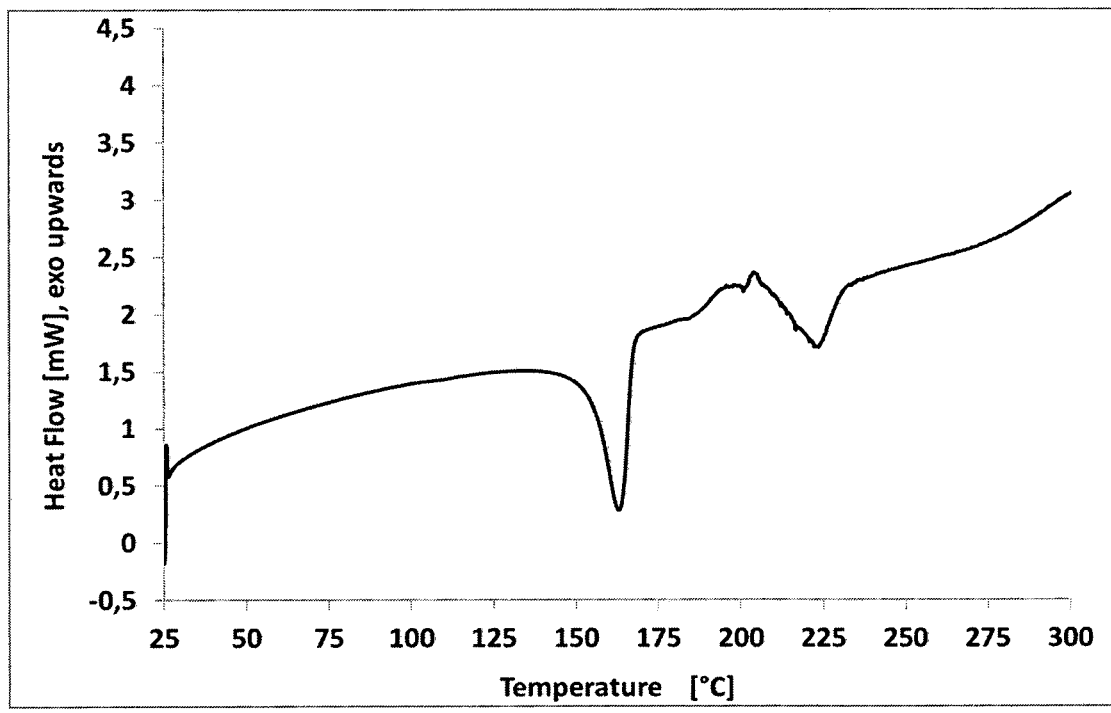
Fig. 16b DSC scan of Tartrate salt form Tartrate-NF1 (5 K/min)

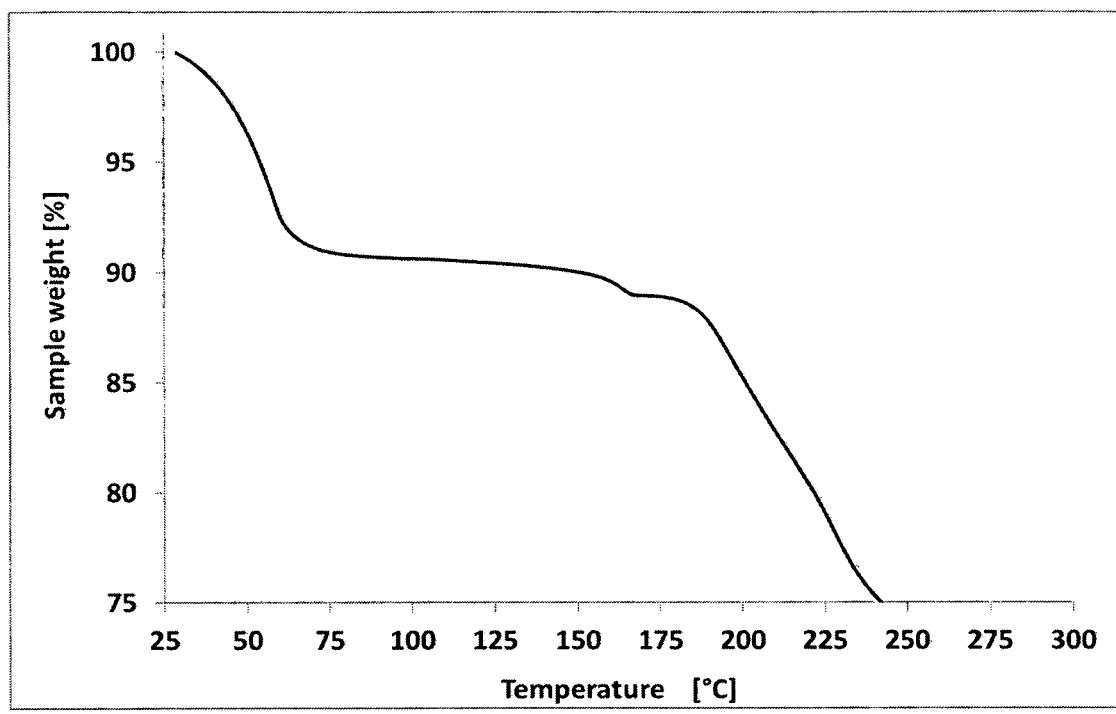
Fig. 16c TGA scan of Tartrate salt form Tartrate-NF1 (5 K/min)
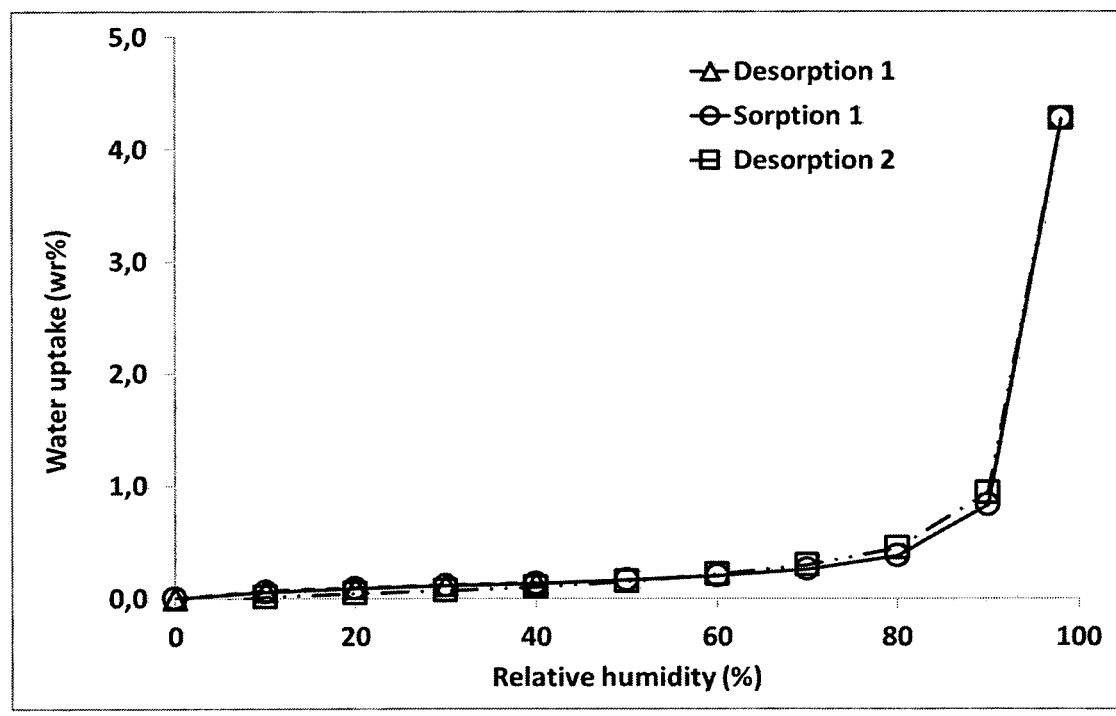
Fig. 16d Water Vapour Sorption Isotherm (25 °C) of Tartrate-NF1

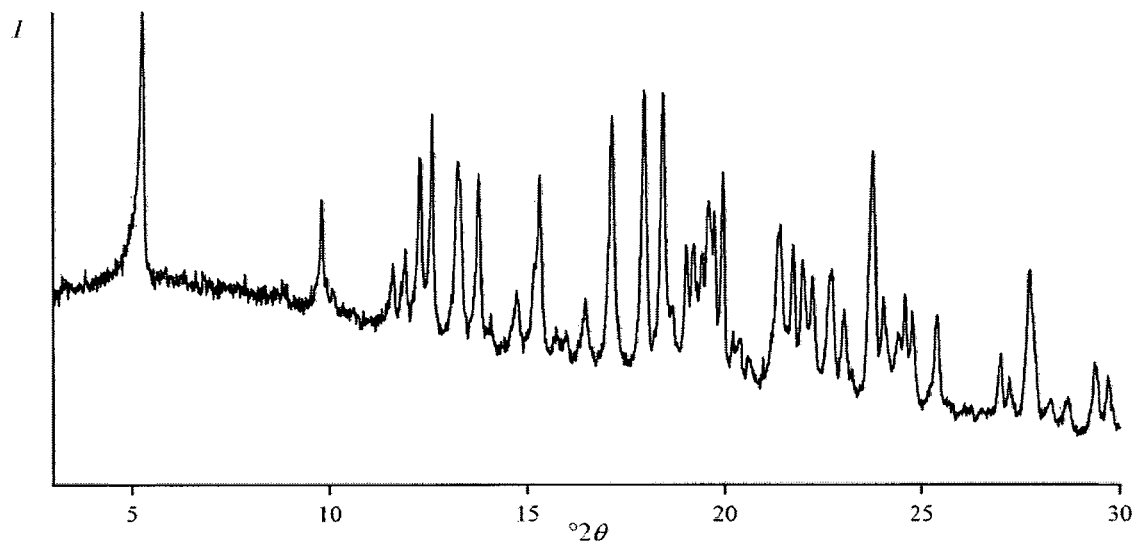
Fig.17a Powder X-ray diffractogram of Malate salt form Malate-NF1
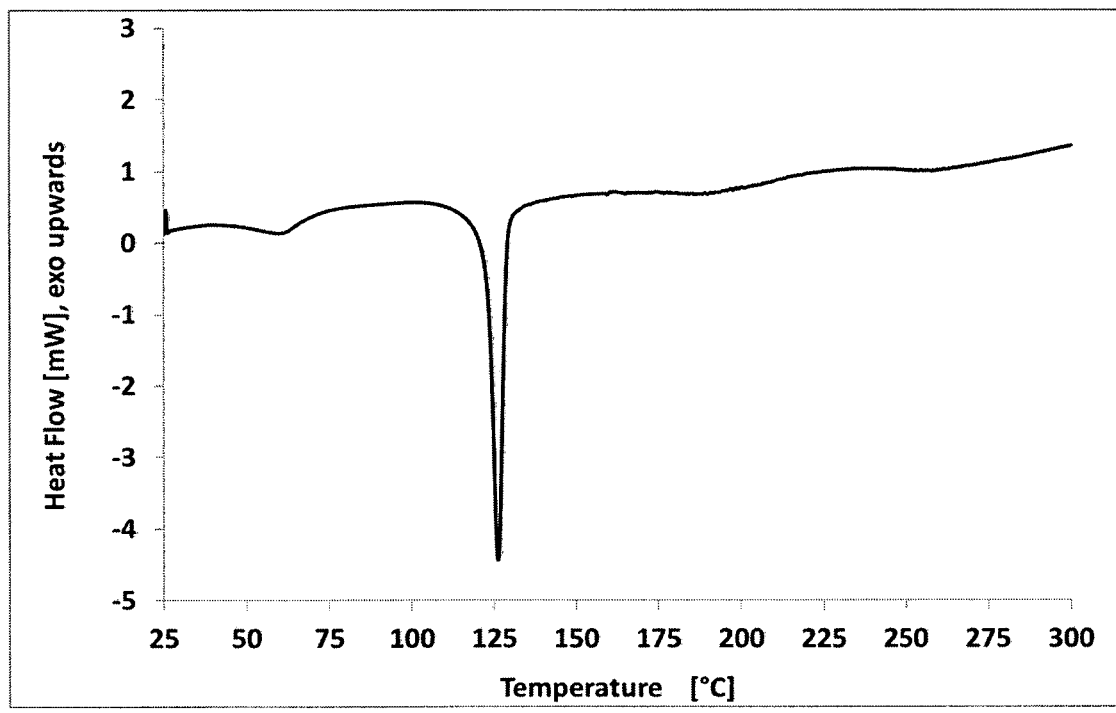
Fig. 17b DSC scan of Malate salt form Malate-NF1 (5 K/min)

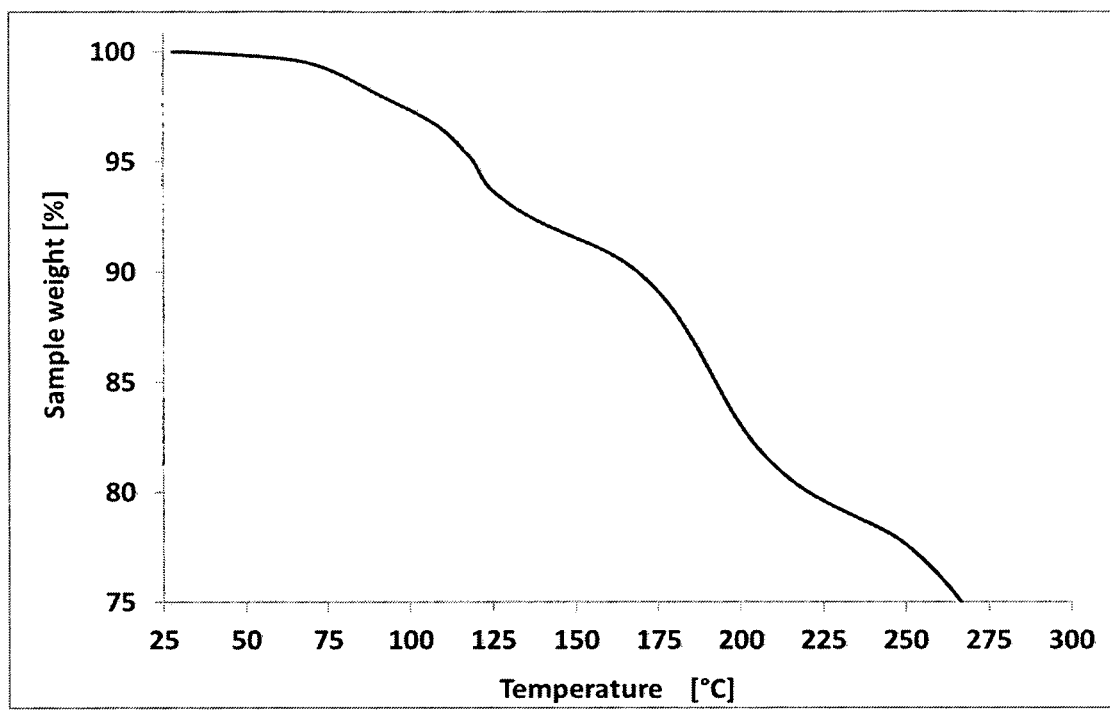
Fig. 17c TGA scan of Malate salt form Malate-NF1 (5 K/min)
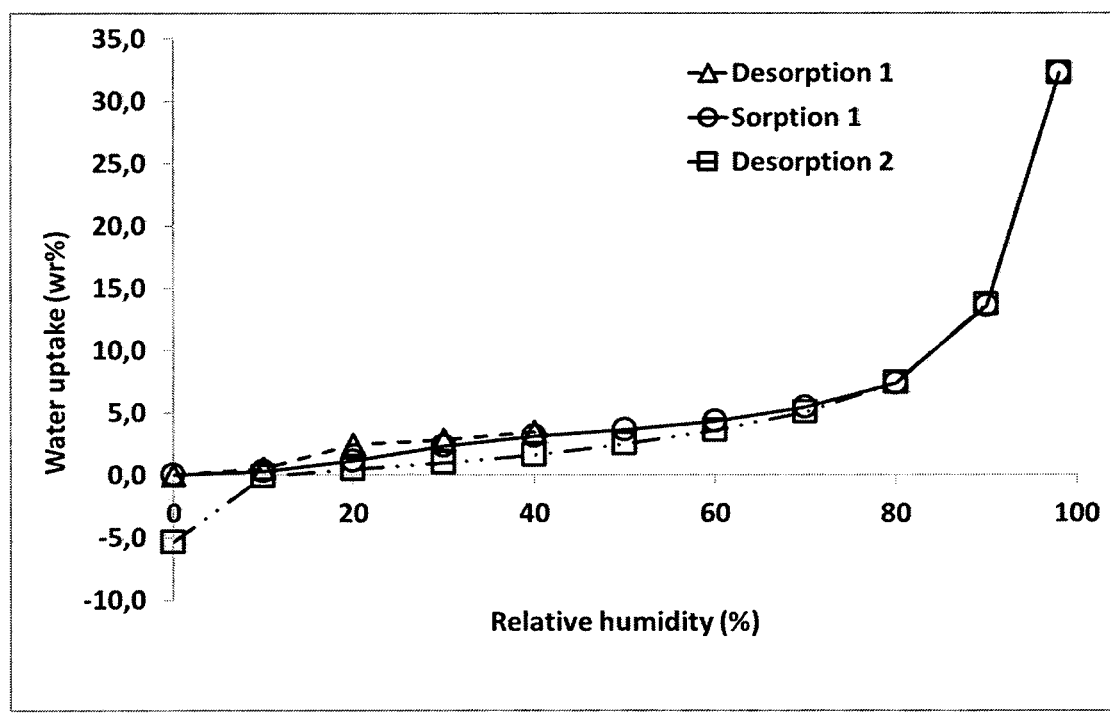
Fig. 17d Water Vapour Sorption Isotherm (25 °C) of Malate salt form Malate-NF1

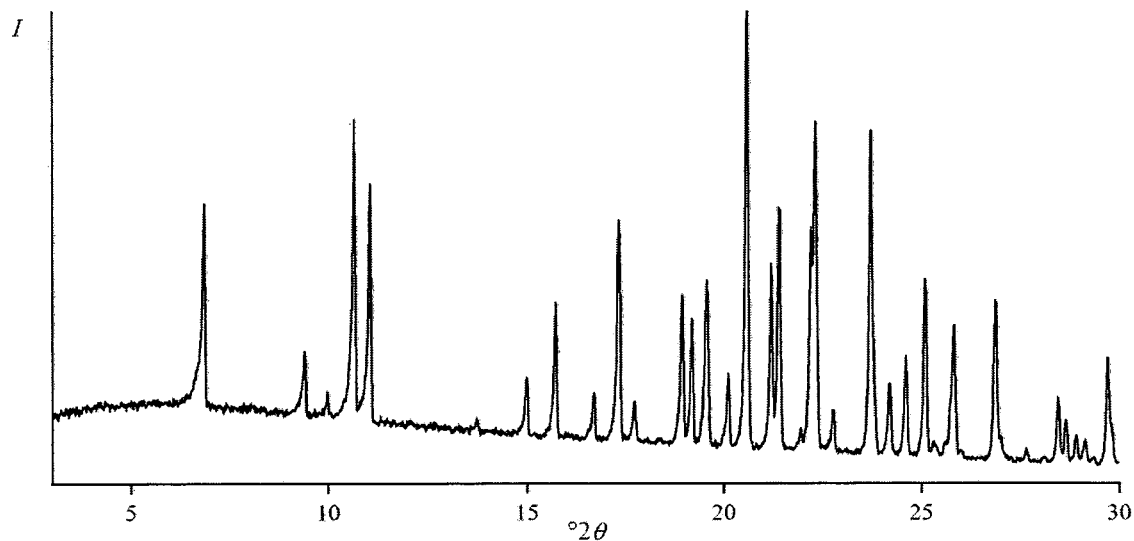
Fig. 18a Powder X-ray diffractogram of HBr salt form HBr-NF1
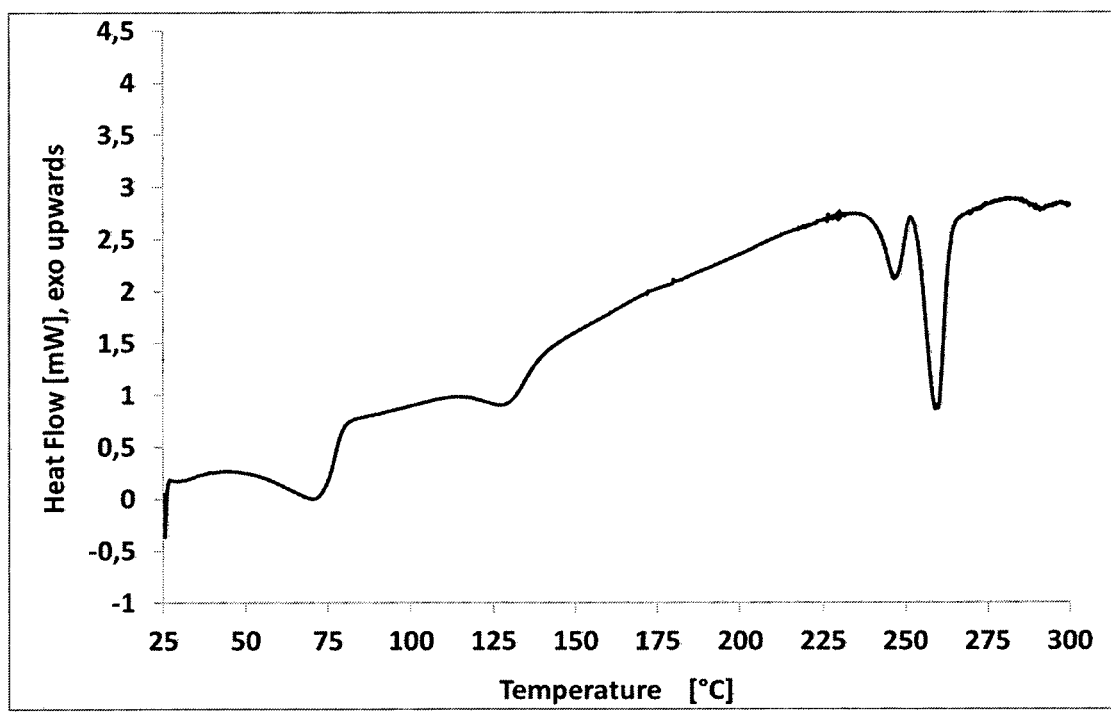
Fig. 18b DSC scan of HBr salt form HBr-NF1 (5 K/min)

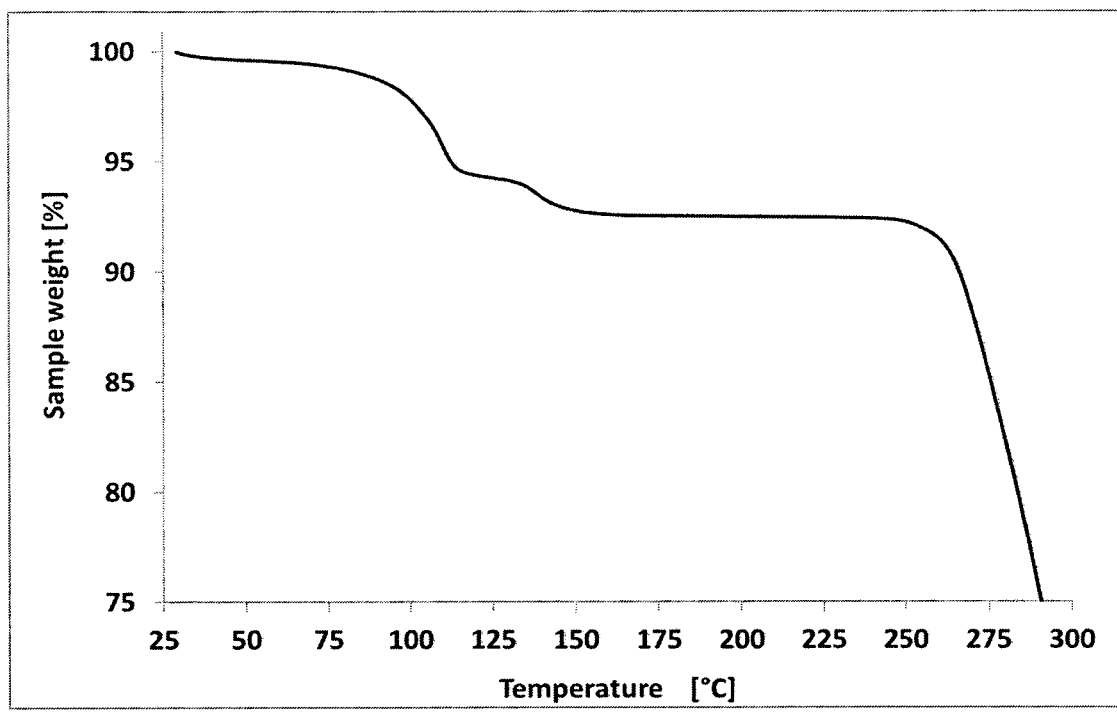
Fig. 18c TGA scan of HBr salt form HBr-NF1 (5 K/min)
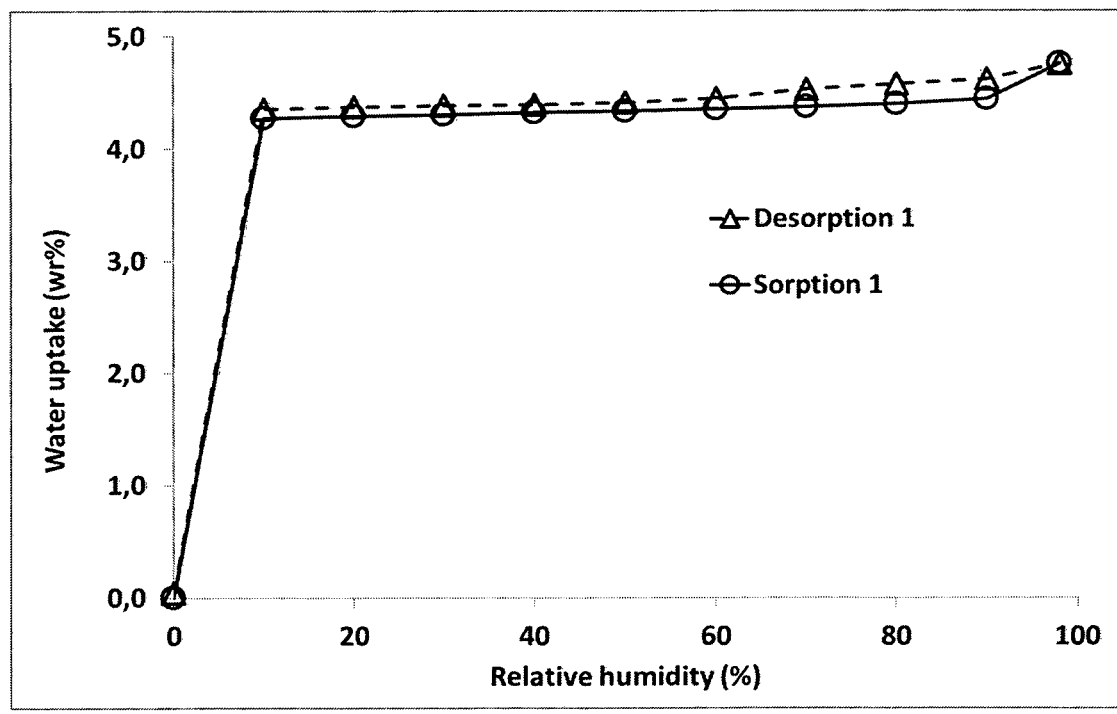
Fig. 18d Water Vapour Sorption Isotherm (25 °C) of HBr salt form HBr-NF1

CRYSTALLINE MODIFICATIONS OF N-(4,5-BISMETHANESULFONYL-2-METHYLBENZOYL)GUANIDINE HYDROCHLORIDE AND N-(4,5-BISMETHANESULFONYL-2-METHYLBENZOYL)GUANIDINE SALTS

CROSS-REFERENCE TO RELATED APPLICATION

This application is the U.S. national stage application of International Patent Application No. PCT/EP2017/000102, filed Jan. 27, 2017.

TECHNICAL FIELD

The present invention relates to novel crystalline modifications of N-(4,5-bismethanesulfonyl-2-methylbenzoyl) guanidine hydrochloride, novel N-(4,5-bismethanesulfonyl-2-methylbenzoyl)guanidine salts, their crystalline modifications and processes of manufacturing and pharmaceutical formulations thereof.

BACKGROUND OF THE INVENTION

Rimeporide, N-(4,5-bismethanesulfonyl-2-methylbenzoyl)guanidine, has the following chemical structure:

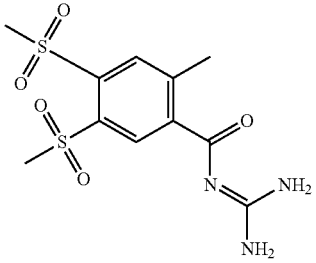 [SMILES: Cc1cc(S(C)(=O)=O)c(S(C)(=O)=O)cc1C(=O)N=C(N)N]

Rimeporide is a potent and selective inhibitor of the ubiquitous sodium-hydrogen antiporter 1 (NHE-1) and has therefore numerous physiological effects. WO 2009/135583 A1 indicates that Rimeporide can be applied as an active ingredient for the treatment of medical indications such as insulin resistance, Diabetes mellitus type 2, metabolic syndrome, diabetic nephropathy and/or peripheral neuropathy (Lupachyk S et al, 2014, J Diab Mellitus), for the enhancement of insulin sensitivity and the preservation or increase of β-cell compensation diseases being linked thereof.

In addition, Rimeporide was shown to be critical in mediating the damage that occurs with myocardial ischemia/reperfusion injury (initial patent application) and is also an important mediator of cardiac hypertrophy. Rimeporide has demonstrated in animal models of DMD and dilated cardiomyopathy (Duchenne Muscular Dystrophy) (Bkaily et al. 2015. J Mol and Cell Cardiology; Chahine et al, 2005. Can. J. Physiol. Pharmacol; Porte Thome et al., 2015, Neuromusc Disorders) to have a good cardioprotective action, which could be useful for the treatment of cardiomyopathy. In addition, in animal models of DMD, Rimeporide has been shown to prevent against the long term accumulation of inflammation and fibrosis in skeletal muscles, the heart and the diaphragm and is thought to be beneficial for the treatment of neuromuscular diseases including Duchenne Muscular Dystrophy, Becker muscular dystrophy, Emery Dreifuss muscular dystrophy, myotonic dystrophy, limb girdle muscular dystrophies, RyR1 muscular dystrophy, and in general any forms of muscular dystrophy/atrophy associated or not with dilated tardiomyopathy.

NHE1 is constitutively active in a neoplastic microenvironment, dysregulating pH homeostasis and altering the survival, differentiation, and proliferation of cancer cells, thereby causing them to become tumorigenic. NHE1 has been shown to contribute to the growth and metastasis of transformed cells. Karki et al (J Bio Chem, 2011) have established that B-Raf associates with and stimulates NHE1 activity and that B-RafV600E also increases NHE1 activity that raises intracellular pH suggesting Rimeporide could be active in melanoma. Other authors have suggested that NHE-1 inhibitors such as Rimeporide could be truly effective anticancer agents in a wide array of malignant tumours including breast cancer, colorectal cancer, NSCLC (non-small lung carcinoma), glioblastoma and leukemia (Harguindey et al, J Trans Med, 2013). To overcome multiple drug resistance, Rimeporide could be used in combination with other chemotherapies such as camptothecin, vinblastine, adriamycin, gemcitabine, paclitaxel (Reshkin et al, Clin Cancer Res, 2003) cariporide and cisplatinum or etoposide (Harguindey et al, J Trans Med, 2013). Rimeporide could also be used in combination with chemotherapeutics drugs and anti angiogenic agents (Pouyssegur et al., Nature, 2006; Gao et al., Leuk Res, 2011) such as adriamycin, cisplatinum, paclitaxel (Reshkin et al., Clin Cancer Res, 2003) and camptothecin and more generally with MAPK inhibitors, MEK inhibitors, JNK inhibitors (Lin et al., Exp. Cell. Re 2011) to promote apoptosis.

In renal diseases, NHE-1 inhibitor abolished Angiotensin II-induced podocyte apoptosis (Liu Y. et al, J Pharmacol Sci, 2013), suggesting that Rimeporide could also be beneficial to treat nephrotic syndromes such as focal segmental glomerulosclerosis, diabetic nephropathy (Li et al., J Diab Res. 2015) and in general in the progression renal impairment.

Liu Y et al, (J Neurosci., 2013) have established that misregulation of local axonal ion homeostasis including pH is an important mechanism for axon degeneration and that selective disruption of NHE1-mediated proton homeostasis in axons can lead to degeneration, suggesting that local regulation of pH is pivotal for axon survival. Rimeporide could be therefore used to present axonal degeneration in Alzheimer's disease, parkinson's disease and other forms of human neurodegenerative diseases.

Pulmonary arterial hypertension (PAH) is a syndrome in which pulmonary arterial obstruction increases pulmonary vascular resistance, which leads to right ventricular (RV) failure and a 15% annual mortality rate. There are 5 categories of pulmonary hypertension (PH) in the latest WHO classification:

| | |
|---|---|
| Group 1. | Pulmonary arterial hypertension (PAH) including:<br>Idiopathic (IPAH)<br>Heritable (HPAH)<br>Drug- and toxin-induced<br>Associated with (APAH)<br>Persistent pulmonary hypertension of the newborn (PPHN)<br>Pulmonary veno-occlusive disease (PVOD) and/or pulmonary capillary haemangiomatosis (PCH) |
| Group 2. | Pulmonary hypertension due to left heart diseases |
| Group 3. | Pulmonary hypertension due to lung diseases and/or hypoxemia |
| Group 4. | Chronic thromboembolic pulmonary hypertension (CTEPH) |
| Group 5. | PH with unclear multifactorial mechanisms |

Hypoxia-induced pulmonary artery hypertension is characterized by elevated pulmonary artery pressure, increased pulmonary vascular resistance, and pulmonary vascular remodeling (Meyrick B., Reid L., Clin Chest Med. 1983; 4 (2): 199-217). With chronic hypoxia there is a rise in pulmonary artery pressure and pulmonary vascular resistance because of both a polycythemia-related increase in blood viscosity and because of a decrease in vascular lumen caused by remodeling. The architectural changes in the pulmonary vasculature include extension of smooth muscle into more distal vessels which are normally nonmuscular, an increase in the muscularity of muscular arteries, and a decrease in the number of countable alveolar arteries. The stimulus for pulmonary artery smooth muscle proliferation is not fully understood, there is growing evidence that activation of the Na+/H+ exchanger may be important in pulmonary cell signaling in response to growth factors as it has been found to be in systemic vessels. (Grinstein S., Rotin D., Mason M. J. Biochim. Biophys, 988(1):73-97, 1989).

Deficiency of the sodium-hydrogen exchanger 1 (NHE1) gene prevented hypoxia-induced pulmonary hypertension and vascular remodeling in mice, which were accompanied by a significantly reduced proliferation of pulmonary artery smooth muscle cells (PASMCs), and which decreased the medial-wall thickness of pulmonary arteries (Huestch J. Shimoda L.; Pulm Circ 2015; 5(2):228-243; 2016).

Increased Na+/H+ exchange with an intracellular alkalization is an early event in cell proliferation. This intracellular alkalization by stimulation of Na+/H+ exchange appears to play a permissive role in the pulmonary artery smooth muscle cell (PASM) proliferation of vascular remodeling.

Inhibition of NHE-1 prevents the development of hypoxia-induced vascular remodeling and PH (Huestch J., Shimoda L. A.; 5 (2):228-243; Pulm Circ 2015). Sabiporide (Wu. D., Doods H., Stassen J M., J Cardiovasc Pharmacol, 48: 34-40), EIPA and Amiloride were shown to inhibit proliferation and migration of human PASMCs in vitro. In vivo, EIPA was shown to inhibit proliferation and migration from. SuHx rats (Huestch J., Jiang H., Larrain C., Shimoda L. A.; Physiologial reports: 4 (5):e 12729, 1-14; 2016). In vivo, cariporide has been shown to attenuate the development of right heart failure in monocrotaline-treated rats (Chen L., Gan T J., Haist J V., Feng Q., Lu X., Chakrabarti S., Karmazyn M., J Pharmacol and Exp Therapeutics; 298: 469-476; 2001).

EndothelineT-1, a circulating factor know to be upregulated in the serum of PH patients (Rubens, C., R. Ewert, M. Halank, R. Wensel, H. D. Orzechowski, H. P. Schultheiss, et al., Chest, 120:1562-1569; 2001), increased NHE activity in normoxic rat PASMCs via activation of ROCK (Undem, C., E. J. Rios, J. Maylor, and L. A. Shimoda. 2012. PLoS One) 7:e46303).

Taken together, Rimeporide could play a beneficial role in all forms (1 to 5) of PAH by inhibiting vascular remodelling, proliferation and migration of PASCMs, with the important caveat that it could also have a positive effect to alleviate myocardial hypertrophic responses in pulmonary vascular injury. The HCl salt of Rimeporide and a crystalline form of the corresponding hydrate are described in EP 0 758 644 A1 and WO 01/30750 A1. Although EP 0 758 644 A1 and WO 01/30750 A1 describe different productions procedures to obtain the crystalline material and also different melting points, a detailed analytical characterization showed that both methods provide the same crystalline modification, which is herein referred to as crystalline modification H1 of N-(4,5-bismethanesulfonyl-2-methylbenzoyl)-guanidine hydrochloride hydrate. EP 0 758 644 A1 describes a melting point of 240° C., this matches with the secondary melding point of re-crystallized H1 phase, which was formed upon heating (see FIG. 1c). WO 01/30750 A1 describes a melting point of 180-188° C., which corresponds to the melting point of form of H1, which is formed upon heating (see FIG. 1c). Other salt forms or crystalline modifications other than crystalline modification H1 are not mentioned EP 0 758 644 A1 and WO 01/30750 A1.

Different salt forms of a compound may have different properties and because of this, different salt forms of a pharmaceutically active ingredient may provide a basis for improving formulation, dissolution profile, stability or shelf-life. Different salts may also give rise to different polymorphic forms, which may provide additional opportunities to improve the properties and characteristics of a pharmaceutical ingredient.

In material science polymorphism is the ability of a solid material to exist in two or more crystal forms that have different arrangements and/or conformations of the molecules in the crystal lattice. Solvates are crystalline solid adducts containing either stoichiometric or non-stoichiometric amounts of a solvent incorporated within the crystal structure. If the incorporated solvent is water, the solvates are also commonly known as hydrates. Polymorphs can be distinguished from one another by different techniques such as powder X-ray diffraction (XRD), thermogravimetric analysis and differential scanning calorimetry. One or more of these techniques may be used to characterize a particular polymorph and to distinguish different polymorphic forms of a compound.

Different polymorphs of a solid material (including solvated forms) can have different properties such as melting point, chemical reactivity, apparent solubility, dissolution rate, vapor pressure, hygroscopicity, particle shape, flowability, compactibility and density. These properties can have a direct effect on the ability to process and manufacture a solid drug substance, as well as on drug product stability, dissolution, and bioavailability. Thus, polymorphism can affect the quality, safety, and efficacy of the drug product. For example, a metastable pharmaceutical solid form can change its crystalline structure or solvate/desolvate in response to changes in environmental conditions or over time. Consequently, stability and shelf life may vary between different polymorphs of a solid substance. New polymorphic forms and solvates of a pharmaceutically useful compound can provide opportunities to improve the performance characteristics of a pharmaceutical product.

After all, there is a need for additional polymorphs and solvates of Rimeporide and its pharmaceutically useful salts.

DESCRIPTION OF THE INVENTION

The present invention provides a crystalline hydrochloride salt of Rimeporide, excluding crystalline modification HCl-H1. In a specific embodiment, the crystalline hydrochloride is an anhydrate form.

In particular, the present invention provides novel solid state forms N-(4,5-bismethanesulfonyl-2-methylbenzoyl) guanidine HCl salt-termed HCl-A1, HCl-A2, HCl-A3 (excluding crystalline modification H1 of N-(4,5-bismethanesulfonyl-2-methylbenzoyl)-guanidine hydrochloride hydrate).

The present invention further provides an anhydrous crystalline salt of Rimeporide selected from a group comprising phosphate salts, citrate salts, oxalate salts, maleate salts, sulfate salts, besylate salts, p-tosylate salts, malonate salts and succinate salts of Rimeporide. The invention also provides a crystalline solvate selected from the group of fumarate salts and tartrate salts of Rimeporide. And the invention provides a crystalline hydrate selected from the group of HBr salts of Rimeporide.

In particular, the present invention further provides following solid state salt forms of N-(4,5-bis-methanesulfonyl-2-methyl-benzoyl)-guanidine:

Phosphate salt, in particular crystalline phosphate salt form termed Phopshate-NF1 (anhydrous form);

Maleate salt, in particular crystalline maleate salt forms termed Maleate-NF1 and Maleate-NF2 (anhydrous forms);

Oxalate salt, in particular crystalline oxalate salt form termed Oxalate-NF1 (anhydrous form);

Citrate salt, in particular crystalline citrate salt form termed Citrate-NF1 (anhydrous form);

Sulfate salt, in particular crystalline sulfate salt form termed Sulfate-NF3 (anhydrous form);

Besylate salt, in particular crystalline besylate salt form termed Besylate-NF1 (anhydrous form);

p-Tosylate salt, in particular crystalline tosylate salt form termed Tosylate-NF1 (anhydrous form);

Malonate salt, in particular crystalline malonate salt form termed Malonate-NF1 (anhydrous form);

Succinate salt, in particular novel crystalline succinate salt form termed Succinate-NF1 (anhydrous form);

fumarate salt, in particular crystalline fumarate salt form termed Fumarate-NF1, representing a 2-propanol-solvate form of fumarate salt entity;

Tartrate salt, in particular crystalline tartrate salt form termed Tartrate-NF1, representing a 2-propanol-solvate form of tartrate salt entity;

Malate salt, in particular crystalline malate salt form termed Malate-NF1, representing a 2-propanol-solvate form of malate salt entity;

HBr salt, in particular crystalline HBr salt form termed HBr-NF1, representing a hydrate form of HBr salt entity.

Unless stated otherwise, the present invention describes solid state forms of Rimeporide, which are chemically pure (chemical purity ≥98% according to NMR analysis).

All forms can be characterized according to standard methods which can be found in e.g. in Rolf Hilfiker, 'Polymorphism in the Pharmaceutical Industry', Wiley-VCH. Weinheim 2006 (Chapter 6: X-Ray Diffraction, Chapter 6: Vibrational Spectroscopy, Chapter 3: Thermal Analysis, Chapter 9: Water Vapour Sorption, and references therein) and H. G. Brittain, 'Polymorphism in Pharmaceutical Solids, Vol. 95, Marcel Dekker Inc., New York 1999 (Chapter 6 and references therein).

As used herein, unless stated otherwise, the X-ray powder diffractogram measurements are taken using monochromatic Cu-Kai radiation wavelength 1.5406 Å. Furthermore, unless stated otherwise, the X-ray powder diffractogram measurements are taken at room temperature.

Solid-state forms of Rimeporide comprise crystal forms or crystalline forms. As used herein, solid-state forms, crystal forms, crystalline forms, polymorphs and polymorphic forms are used interchangeably.

Crystal form may be referred to herein as being characterized by graphical data "substantially as depicted in" or "as depicted in" a Figure. Such graphical data includes for example powder X-ray diffractograms and DSC or TGA. The graphical data potentially provides additional technical information useful to define a particular solid-state form which cannot or not easily be described by reference to numerical values for peak positions and/or relative intensities. The skilled person understands that such graphical representations of data may be subject to small variations, e.g. relative peak intensities and peak positions may vary due to factors such as variations in instrument response and sample concentration and purity. The skilled person would readily be capable of comparing the graphical data shown in the Figures herein with graphical data generated for an unknown crystal form and confirm whether the two sets of graphical data are characterizing the same crystal form or two different crystal forms.

A solid-state form may referred to herein as being characterized by analytical data selected from more different data groupings, such as for example by a X-ray powder diffractogram pattern having a group of specific peaks, or by a X-ray powder diffractogram as shown in a figure, or by "a combination thereof" (or "combinations of these data"). These expressions, e.g., "combination thereof" contemplates that skilled person may characterize a solid state form using any combination of the recited characteristic analytical data. For example, the skilled person may characterize a crystal form using a group, for example, four, five or six characteristic X-ray powder diffractogram peaks, and supplement that characterization with one or more additional features observed in the powder diffractogram, for example an additional peak, characteristic peak shape, peak intensity, or even the absence of a peak at some position in the powder X-ray powder diffractogram pattern. Alternatively, a skilled person may characterize the crystal form using a group of, for example, four, five, six, seven, eight, nine or ten characteristic powder X-ray powder diffractogram peaks, and supplement that characterizing data with one or more additional features observed using another analytical method, for example, using characteristics of the DSC thermogram of the crystal form that is being characterized. As used herein, unless stated otherwise, the XRPD measurements are taken at room temperature using Cu-Kai radiation wavelength 1.5406 Å.

As used herein, unless stated otherwise, the single crystal X-Ray structure data can be obtained with an Oxford Diffraction Xcalibur™ Single Crystal X-ray Diffractometer with Sapphire CCD Detector at 303 K.

Crystal form (or polymorph) described herein are pure or substantially free of any other crystalline (or polymorphic form). As used herein means that the crystalline form contains 10% or less, of any other known form of the subject compound as measured for example by PXRD.

As used herein, unless stated otherwise, the term "powder" refers to a solid compound in the form of particles or granules, wherein the particles or granules can be poured.

As used herein, unless stated otherwise, the DSC measurements are carried out using a Mettler-Toledo DSC 821 with a heating rate of 5 K/min, using nitrogen purge gas at 50 mL/min.

As used herein, unless stated otherwise, the TGA measurements are carried out using a Mettler-Toledo TGA 851 with a heating rate of 5 K/min, using nitrogen purge gas at 50 mL/min.

As used herein, unless stated otherwise, Water Vapour Sorption isotherm measurements are carried out on a DVS-1 or a DVS-Intrinsic system from SMS.

As used herein and unless stated otherwise, the term "anhydrous" refers to crystalline material which contains not more than 1% (w/w) of either water or organic solvents as measured by TGA. In the context of the present invention, an anhydrous solid state form of a compound refers to a form that does not contain crystal water (or other solvents) in a defined amount within the crystal.

As used herein, unless stated otherwise, the term "solvate" refers to a crystal form that incorporates a solvent in the crystal structure. When the solvent is water, such a form is often referred to as a "hydrate".

The following abbreviations refer to the abbreviations used below: iso-BuOH (iso-butanol), n-BuOH (n-butanol), dec (decomposition), DSC (differential scanning calorimetry), DI (de-ionized), DMSO (dimethyl sulfoxide) EtOH (ethanol), FeSSIF (Fed State Simulated Intestinal Fluid), g (gram), HPLC (high performance liquid chromatography), hr (hour), MHz (Megahertz), MeOH (methanol), min (minute), mL (milliliter), mmol (millimole), mM (millimolar), mp (melting point), MS (mass spectrometry), MW (microwave), NMR (Nuclear Magnetic Resonance), Ph. Eur. (Pharmacopoea Europaea), PTFE (Polytetrafluoroethylene), 2-PrOH (2-propanol), RH (relative humidity), RT (room temperature), TGA (thermal gravimetric analysis), THF (tetrahydrofuran), TMS (trimethylsilyl), UV (ultraviolet), wt % (weight percent), X-ray powder diffractogram (XRPD).

In one aspect, the present invention provides a crystalline form of Rimeporide (N-(4,5-bis-methanesulfonyl-2-methyl-benzoyl)-guanidine) HCl salt, designated as form HCl-A1. Crystalline form HCl-A1 can be characterized by following data:
  a) a powder X-ray diffraction pattern having one, two, three, four or five peaks at a diffraction angle (2 theta) of 14.0°±0.2°, 18.5°±0.2°, 19.6°±0.2°, 20.4°±0.2° and/or 22.1°±0.2°;
  b) a powder X-ray diffraction pattern having a peak at a diffraction angle 2 theta of 14.0°±0.2°, 18.5°±0.2°, 19.6°±0.2°, 20.4°±0.2° and 22.1°±0.2° and also having one, two, three, four or five additional peaks a diffraction angle 2 theta of 11.0°±0.2°, 19.0°±0.2°, 23.0°±0.2°, 24.2°±0.2° and/or 24.4°±0.2°;
  c) a powder X-ray diffraction pattern according to TableHCl-A1;
  d) a XRPD pattern substantially as depicted in FIG. 2a; or
  e) monoclinic space group $P2_1/c$, unit cell lattice parameters a=10.2±0.1 Å, b=17.6±0.1 Å, c=9.5±0.1 Å, and β=108.8±0.5° (with α=γ=90°);
and by a combination of these data such as in particular a combination of a) and e), b) and e), c) and e) and d) and e).

A peak list corresponding to the XRPD of FIG. 2a is shown in TableHCl-A1.

| TableHCl-A1 Powder X-ray peak list of HCl salt form HCl-A1 | |
| --- | --- |
| No. | °2θ (Cu-Kα1 radiation) ± 0.2° |
| 1 | 10.0 |
| 2 | 10.4 |
| 3 | 11.0 |
| 4 | 12.1 |
| 5 | 13.6 |
| 6 | 14.0 |
| 7 | 18.5 |
| 8 | 18.7 |
| 9 | 19.0 |
| 10 | 19.6 |
| 11 | 20.4 |
| 12 | 22.1 |
| 13 | 23.0 |
| 14 | 23.8 |
| 15 | 24.2 |
| 16 | 24.4 |
| 17 | 24.8 |
| 18 | 26.9 |
| 19 | 27.6 |
| 20 | 28.1 |

The single crystal structure shown in FIG. 2b indicates that form HCl-A1 represents an HCl salt anhydrous form. HCl salt form HCl-A1 can be further characterized by following physical property:
  Dissolution level in Fed-State Simulated Intestinal Fluid [FeSSIF, pH 5.0] at 37° C. is 0.87±0.02 mg/mL (after 15 min), 2.53±0.02 mg/mL (after 60 min), and 2.76±0.02 mg/mL (after 120 min), respectively (see example 17).

Another aspect of the inventions comprises a crystalline form of Rimeporide HCl salt, designated as form HCl-A2. Form HCl-A2 can be characterized by following data:
  a) a powder X-ray diffraction pattern having one, two, three, four or five peaks at a diffraction angle (2 theta) of 11.9°±0.2°, 14.9°±0.2°, 17.7°±0.2°, 21.8°±0.2° and/or 22.5°±0.2°;
  b) a powder X-ray diffraction pattern having a peak at an angle of diffraction at degrees 2 theta of 11.9°±0.2°, 14.9°±0.2°, 17.7°±0.2°, 21.8°±0.2° and 22.5°±0.2° and also having one, two, three, four or five additional peaks a diffraction angle 2 theta of 13.2°±0.2°, 15.6°±0.2°, 20.3°±0.2°, 21.3°±0.2° and 26.9°±0.2°;
  c) a powder X-ray diffraction pattern according to TableHCl-A2;
  d) a XRPD pattern substantially as depicted in FIG. 3a;
  e) DSC data substantially as depicted in FIG. 3c;
  f) TGA data substantially as depicted in FIG. 3d;
  g) monoclinic space group $P2_1/c$; or
  h) unit cell lattice parameters a=11.9±0.1 Å, b=9.5±0.1 Å, c=14.2±0.1 Å, and β=94.6±0.5° with α=γ=90;
and by a combination of these data such as in particular a combination of a) and e), f), g) and/or h); b) and e), f), g) and/or h); c) and e), f), g) and/or h); d) and e), f), g) and/or h).

A peak list corresponding to the XRPD of FIG. 3a is shown in TableHCl-A2. The single crystal structure shown in FIG. 3b indicates that form HCl-A2 represents an HCl salt anhydrous form.

| TableHCl-A2 Powder X-ray peak list of HCl salt form HCl-A2 | |
| --- | --- |
| No. | °2θ (Cu-Kα₁ radiation) ± 0.2° |
| 1 | 7.4 |
| 2 | 11.9 |
| 3 | 12.6 |
| 4 | 13.2 |
| 5 | 14.9 |
| 6 | 15.6 |
| 7 | 16.9 |
| 8 | 17.7 |
| 9 | 19.1 |
| 10 | 20.3 |
| 11 | 20.9 |
| 12 | 21.3 |
| 13 | 21.8 |
| 14 | 22.5 |
| 15 | 24.5 |
| 16 | 25.6 |
| 17 | 26.9 |

-continued

TableHCl-A2 Powder X-ray peak list of HCl salt form HCl-A2

| No. | °2θ (Cu-Kα₁ radiation) ± 0.2° |
|---|---|
| 18 | 28.1 |
| 19 | 28.3 |
| 20 | 29.7 |

HCl salt form HCl-A2 can be further characterized by following physical properties:

Chloride content (determined by ion chromatography) of 9.1 wt % chloride (corresponds to 0.96 eq. Chloride);

Thermal behavior of form. HCl-A2 shows a strong endothermic event >240° C., which goes along with strong weight loss in the TGA profile. This can be assigned to melting/decomposition processes of form HCl-A2. DSC and TGA profiles are displayed in FIGS. 3c and 3d;

Water Vapour Sorption behavior of form HCl-A2 reveals very small water uptake levels 0.1 wt % in the relative humidity (rh) range 0-80% rh. Form HCl-A2 can be classified as non-hygroscopic acc. to Ph. Eur. criteria (section 5.11.). Water Vapor Sorption isotherm (25° C.) of form HCl-A2 is displayed in FIG. 3e; and/or Dissolution level of form HCl-A2 (measured with a sample containing very small fractions (approx. 10%) of hydrate form H1) in Fed-State Simulated Intestinal Fluid [FeSSIF, pH 5.0] at 37° C. is 1.19±0.02 mg/mL (after 15 min), 1.90±0.02 mg/mL (after 60 min), and 2.21±0.02 mg/mL (after 120 min), respectively (see example 17).

In another aspect the invention provides a crystalline form of HCl salt, designated as form HCl-A3. Form HCl-A3 can be characterized by following data:

a) a powder X-ray diffraction pattern having one, two, three, four or five peaks at a diffraction angle (2 theta) of 14.2°±0.2°, 17.1°±0.2°, 17.4°±0.2°, 18.5°±0.2° and/or 24.1°±0.2°;

b) a powder X-ray diffraction pattern having a peaks at an angle of diffraction at degrees 2 theta of 14.2°±0.2°, 17.1°±0.2°, 17.4°±0.2°, 18.5°±0.2° and/or 24.1°±0.2° and also having one, two, three, four or five additional peaks a diffraction angle 2 theta of 11.9°±0.2°, 12.8°±0.2°, 15.6°±0.2°, 20.4°±0.2° and/or 22.0°±0.2°;

c) a powder X-ray diffraction pattern according to TableHCl-A3;

d) a XRPD pattern substantially as depicted in FIG. 4a;

e) DSC data substantially as depicted in FIG. 4c;

f) TGA data substantially as depicted in FIG. 4d;

g) monoclinic space group P2₁/c, or h) unit cell lattice parameters a=19.1±0.1 Å, b=14.8±0.1 Å, c=11.6±0.1 Å, and β=95.7±0.5° (with α=γ=90°);

and by a combination of these data such as in particular a combination of a) and e), f), g) and/or h); b) and e), f), g) and/or h); c) and e), f), g) and/or h); d) and e), f), g) and/or h).

A peak list corresponding to the XRPD of FIG. 4a is shown in TableHCl-A3. The single crystal structure shown in FIG. 4b indicates that form HCl-A3 represents an HCl salt anhydrous form.

TableHCl-A3 Powder X-ray peak list of HCl salt form HCl-A3

| No. | °2θ (Cu-Kα₁ radiation) ± 0.2° |
|---|---|
| 1 | 4.6 |
| 2 | 7.5 |
| 3 | 10.4 |
| 4 | 11.9 |
| 5 | 12.8 |
| 6 | 14.2 |
| 7 | 15.2 |
| 8 | 15.6 |
| 9 | 16.5 |
| 10 | 17.1 |
| 11 | 17.4 |
| 12 | 18.2 |
| 13 | 18.5 |
| 14 | 19.5 |
| 15 | 19.7 |
| 16 | 20.4 |
| 17 | 22.0 |
| 18 | 22.2 |
| 19 | 23.7 |
| 20 | 24.1 |

HCl salt form HCl-A3 can be further characterized by following physical properties:

Chloride content (determined by ion chromatography) of 9.9 wt % chloride (corresponds to 1.05 eq. Chloride);

Thermal behavior of form HCl-A3 shows strong endothermic events >220° C., which goes along with strong weight loss in the TGA profile. This can be assigned to melting/decomposition processes of form HCl-A3. DSC and TGA profiles are displayed in FIGS. 4c and 4d;

Water Vapour Sorption behavior of form HCl-A3 reveals very small water uptake levels ≤0.4 wt % in the entire relative humidity (rh) range 0-98% rh. Form HCl-A3 can be classified as non-hygroscopic acc. to Ph. Eur. criteria (section 5.11.). Water Vapour Sorption isotherm (25° C.) of form HCl-A3 is displayed in FIG. 4e; and/or Dissolution level of form HCl-A3 (representing a sample with very small fractions (approx. 10%) of hydrate form H1) in Fed-State Simulated Intestinal Fluid [FeSSIF, pH 5.0] at 37° C. is 0.74±0.02 mg/mL (after 15 min), 2.51±0.02 mg/mL (after 60 min), and 3.78±0.02 mg/mL (after 120 min), respectively (see example 17).

In another aspect the invention provides a crystalline form of Rimeporide phosphate salt, designated as form Phosphate-NF1. Form Phosphate-NF1 can be characterized by following data:

a) a powder X-ray diffraction pattern having one, two, three, four or five peaks at a diffraction angle 2 theta of 13.9°±0.2°, 16.9°±0.2°, 17.3°±0.2°, 21.8°±0.2° and/or 22.1°±0.2°;

b) at a diffraction angle 2 theta of 13.9°±0.2°, 16.9°±0.2°, 17.3°±0.2°, 21.8°±0.2° and 22.1°±0.2° and also having one, two, three, four or five additional peaks at a diffraction angle 2 theta of 8.4°±0.2°, 14.6°±0.2°, 17.5°±0.2°, 20.6°±0.2° and/or 22.3°±0.2°;

c) a powder X-ray diffraction pattern according to Table-Phosphate-NF1;

d) a XRPD pattern substantially as depicted in FIG. 5a;

e) DSC data substantially as depicted in FIG. 5b; or f) TGA data substantially as depicted in FIG. 5c;

and by a combination of these data such as in particular a combination of a) and e) and/or f); b) and e) and/or f); c) and e) and/or f); and d) and e) and/or f).

A peak list corresponding to the XRPD of FIG. 5a is shown in TablePhosphate-NF1.

| TablePhosphate-NF1: Powder X-ray peak list of Phosphate salt form Phosphate-NF1 | |
|---|---|
| No. | °2θ (Cu-Kα₁ radiation) ± 0.2° |
| 1 | 8.4 |
| 2 | 13.9 |
| 3 | 14.6 |
| 4 | 15.4 |
| 5 | 16.4 |
| 6 | 16.9 |
| 7 | 17.3 |
| 8 | 17.5 |
| 9 | 19.4 |
| 10 | 20.6 |
| 11 | 20.9 |
| 12 | 21.8 |
| 13 | 22.1 |
| 14 | 22.3 |
| 15 | 23.1 |
| 16 | 24.5 |
| 17 | 26.3 |
| 18 | 26.5 |
| 19 | 28.0 |

Phosphate salt form Phosphate-NF1 can be further characterized by one or more of following physical properties:
  Phosphate content (determined by ion chromatography) of 22.0 wt % phosphate (corresponds to 1.02 eq. Phosphate);
  Thermal behavior of form Phosphate-NF1 shows strong endothermic events >230° C., which goes along with strong weight loss in the TGA profile. This can be assigned to melting/decomposition processes of form Phosphate-NF1. DSC and TGA profiles are displayed in FIGS. 5b and 5c;
  Water Vapor Sorption behavior of form Phosphate-NF1 reveals very small water uptake levels ≤1.0 wt % in the relative humidity (rh) range 0-90% rh. Form Phosphate-NF1 can be classified as slightly hygroscopic acc. to Ph. Eur. criteria (section 5.11.). Water Vapour Sorption isotherm (25° C.) of form Phosphate-NF1 is displayed in FIG. 5d; and/or
  Dissolution level of form Phosphate-NF1 in Fed-State Simulated Intestinal Fluid [FeSSIF, pH 5.0] at 37° C. is 5.92±0.02 mg/mL (after 15 min), 6.35±0.02 mg/mL (after 60 min), and 6.35±0.02 mg/mL (after 120 min), respectively (see example 17).

In another aspect the invention provides a crystalline form of Rimeporide maleate salt, designated as form Maleate-NF1 Form Maleate-NF1 can be characterized by following data:
  a) a powder X-ray diffraction pattern having one, two, three, four or five peaks at a diffraction angle 2 theta of 7.6±0.2°, 11.1°±0.2°, 19.5°±0.2°, 20.3°±0.2° and/or 20.7°±0.2°;
  b) a powder X-ray diffraction pattern having peaks at a diffraction angle 2 theta of 7.6±0.2°, 11.1°±0.2°, 19.5°±0.2°, 20.3°±0.2° and/or 20.7°±0.2° and also having one, two, three, four or five additional peaks at a diffraction angle 2 theta of 7.8°±0.2°, 8.2°±0.2°, 15.1°±0.2°, 18.9°±0.2° and/or 23.4°±0.2°;
  c) a powder X-ray diffraction pattern according to Table-Maleate-NF1;
  d.) a XRPD pattern substantially as depicted in FIG. 6a; or
  e) TGA data substantially as depicted in FIG. 6b;
and by a combination of these data such as in particular a combination of a) and e) and/or f); b) and e) and/or f); and c) and e) and/or f).

A peak list corresponding to the XRPD of FIG. 6a is shown in Table Maleate-NF1.

| TableMaleate-NF1: Powder X-ray peak list of Maleate salt form Maleate-NF1 | |
|---|---|
| No. | °2θ (Cu-Kα₁ radiation) ± 0.2° |
| 1 | 7.6 |
| 2 | 7.8 |
| 3 | 8.2 |
| 4 | 9.9 |
| 5 | 10.1 |
| 6 | 11.1 |
| 7 | 12.3 |
| 8 | 13.7 |
| 9 | 15.1 |
| 10 | 15.8 |
| 11 | 16.4 |
| 12 | 17.0 |
| 13 | 18.9 |
| 14 | 19.5 |
| 15 | 20.3 |
| 16 | 20.7 |
| 17 | 21.9 |
| 18 | 23.4 |
| 19 | 25.4 |
| 20 | 28.6 |

Maleate salt form Maleate-NF1 can be further characterised by following physical properties:
  Maleate content (determined by 1H-NMR spectroscopy) is 1.0 eq. Maleate; and/or
  Thermal behavior of form Maleate-NF1 shows strong weight loss in the TGA profile >170° C. This can be assigned to decomposition processes of form Maleate-NF1. The TGA profile is displayed in FIG. 6b.

In another aspect the invention provides a crystalline form of Rimeporide maleate salt, designated as form Maleate-NF2. Form Maleate-NF2 can be characterized by following data:
  a) a powder X-ray diffraction pattern having one, two, three, four or five peaks at a diffraction angle 2 theta of 16.3±0.2°, 18.7°±0.2°, 20.4°±0.2°, 20.7°±0.2° and/or 25.3°±0.2°;
  b) a powder X-ray diffraction pattern having peaks at a diffraction angle 2 theta of 16.3±0.2°, 18.7°±0.2°, 20.4°±0.2°, 20.7°±0.2° and 25.3°±0.2° and also having one, two, three, four or five additional peaks at a diffraction angle 2 theta of 9.3°±0.2°, 17.1°±0.2°, 19.7°±0.2°, 22.0°±0.2° and/or 26.2°±0.2°;
  c) a powder X-ray diffraction pattern according to Table-Maleate-NF2;
  d) a XRPD pattern substantially as depicted in FIG. 7a;
  e) DSC data substantially as depicted in FIG. 7b; or
  f) TGA data substantially as depicted in FIG. 7c;
and by a combination of these data such as in particular a combination of a) and e), b) and e), c) and e) or d) and e).

A peak list corresponding to the XRPD of FIG. 6a is shown in TableMaleate-NF2.

| TableMaleate-NF2: Powder X-ray peak list of Maleate salt form Maleate-NF2: | |
|---|---|
| No. | °2θ (Cu-Kα₁ radiation) ± 0.2° |
| 1 | 7.9 |
| 2 | 9.3 |
| 3 | 11.3 |
| 4 | 13.0 |

| TableMaleate-NF2: Powder X-ray peak list of Maleate salt form Maleate-NF2: | |
|---|---|
| No. | °2θ (Cu-Kα₁ radiation) ± 0.2° |
| 5 | 15.0 |
| 6 | 15.6 |
| 7 | 16.3 |
| 8 | 17.1 |
| 9 | 18.7 |
| 10 | 19.7 |
| 11 | 20.4 |
| 12 | 20.7 |
| 13 | 21.7 |
| 14 | 22.0 |
| 15 | 22.8 |
| 16 | 23.6 |
| 17 | 25.3 |
| 18 | 26.2 |
| 19 | 28.3 |

Maleate salt form Maleate-NF2 can be further characterised by following physical properties:

Maleate content (determined by 1H-NMR spectroscopy) is 1.0 eq. Maleate;

Thermal behavior of form Maleate-NF2 shows strong endothermic events >200° C., which goes along with strong weight loss in the TGA profile. This can be assigned to melting/decomposition processes of form Maleate-NF2 (see FIGS. 7b and 7c);

Water Vapor Sorption behavior of form Maleate-NF2 reveals very small water uptake levels ≤0.3 wt % in the entire relative humidity (rh) range 0-98% rh. Form Maleate-NF2 can be classified as slightly hygroscopic acc. to Ph. Eur. criteria (section 5.11.). Water Vapour Sorption isotherm (25° C.) of form Maleate-NF2 is displayed in FIG. 7d; and/or Dissolution level of form Maleate-NF2 in Fed-State Simulated Intestinal Fluid [FeSSIF, pH 5.0] at 37° C. is 4.30±0.02 mg/mL (after 15 min), 6.35±0.02 mg/mL (after 60 min), and 6.35±0.02 mg/mL (after 120 min), respectively (see example 17).

In another aspect the invention provides a crystalline form of Rimeporide oxalate salt, designated as form Oxalate-NF1. Form Oxalate-NF1 can be characterized by following data:
a) a powder X-ray diffraction pattern having one, two, three, four or five peaks at a diffraction angle 2 theta of 13.2°±0.2°, 16.4°±0.2°, 17.1°±0.2°, 21.3°±0.2° and/or 23.3°±0.2°;
b) a powder X-ray diffraction pattern having peaks at a diffraction angle 2 theta of 13.2°±0.2°, 16.4°±0.2°, 17.1°±0.2°, 21.3°±0.2° and/or 23.3°±0.2° and also having one, two, three, four or five additional peaks at a diffraction angle 2 theta of 17.9°±0.2°, 20.4°±0.2°, 21.6°±0.2°, 23.0°±0.2° and/or 25.0°±0.2°;
c) a powder X-ray diffraction pattern according to TableOxalate-NF1;
d) a XRPD pattern substantially as depicted in FIG. 8a;
e) DSC data substantially as depicted in FIG. 8b; or
f) TGA data substantially as depicted in FIG. 8c;
and by a combination of these data such as in particular a combination of a) and e) and/or f); b) and e) and/or f); c) and e) and/or f); and d) and e) and/or f).

A peak list corresponding to the XRPD of FIG. 8a is shown in TableOxalate-NF1.

| TableOxalate-NF1: Powder X-ray peak list of Oxalate salt form Oxalate-NF1: | |
|---|---|
| No. | °2θ (Cu-Kα₁ radiation) ± 0.2° |
| 1 | 6.6 |
| 2 | 11.6 |
| 3 | 13.0 |
| 4 | 13.2 |
| 5 | 13.6 |
| 6 | 15.0 |
| 7 | 16.4 |
| 8 | 17.1 |
| 9 | 17.3 |
| 10 | 17.9 |
| 11 | 19.9 |
| 12 | 20.4 |
| 13 | 21.3 |
| 14 | 21.6 |
| 15 | 22.7 |
| 16 | 23.0 |
| 17 | 23.3 |
| 18 | 24.6 |
| 19 | 25.0 |
| 20 | 28.0 |

Oxalate salt form Oxalate-NF1 can be further characterized by one or more of following physical properties:

Oxalate content (determined by ion chromatography) is 12.1 wt % Oxalate (corresponding to 0.52 eq. Oxalate);

Thermal behavior of form Oxalate-NF1 shows strong endothermic events >260° C., which goes along, with strong weight loss in the TGA. profile. This can be assigned to melting/decomposition processes of form Oxalate-NF1. DSC and TGA profiles are displayed in FIGS. 8b and 8c; and/or Dissolution level of form Oxalate-NF1 in Fed State Simulated Intestinal Fluid [FeSSIF, pH 5.0] at 37° C. is 2.09±0.02 mg/mL (after 15 min), 3.04±0.02 mg/mL (after 60 min), and 3.02±0.02 mg/mL (after 120 min), respectively (see example 17).

In another aspect the invention provides a crystalline form of Rimeporide citrate salt, designated as form Citrate-NF1. Form Citrate-NF1 can be characterized by following data:
a) a powder X-ray diffraction pattern having one, two, three, four or five peaks at a diffraction angle 2 theta of 11.9°±0.2, 15.0°±0.2, 18.1°±0.2, 19.5°±0.2 and/or 20.3°±0.2;
b) a powder X-ray diffraction pattern having a peaks at a diffraction angle 2 theta of 11.9°±0.2, 15.0°±0.2, 18.1°±0.2, 19.5°±0.2 and 20.3°±0.2° and also having one, two, three, four or five additional peaks at a diffraction angle 2 theta 10.7°±0.2°, 17.3°±0.2°, 18.7°±0.2°, 20.8°±0.2° and/or 25.3°±0.2°;
c) a powder X-ray diffraction pattern according to TableCitrate-NF1;
d) a XRPD pattern substantially as depicted in FIG. 9a;
e) DSC data substantially as depicted in FIG. 9b; or
f) TGA data substantially as depicted in FIG. 9c.
and by a combination of these data such as in particular a combination of a) and e) and/or f); b) and e) and/or f); c) and e) and/or f); and d) and e) and/or f).

A peak list corresponding to the XRPD of FIG. 9a is shown in TableCitrate-NF1.

| TableCitrate-NF1: Powder X-ray peak list of Citrate salt form Citrate-NF1: | |
|---|---|
| No. | °2θ (Cu-Kα₁ radiation) ± 0.2° |
| 1 | 6.7 |
| 2 | 7.2 |
| 3 | 10.7 |
| 4 | 11.9 |
| 5 | 12.6 |
| 6 | 14.1 |
| 7 | 15.0 |
| 8 | 17.3 |
| 9 | 18.1 |
| 10 | 18.7 |
| 11 | 19.5 |
| 12 | 20.3 |
| 13 | 20.8 |
| 14 | 22.2 |
| 15 | 22.8 |
| 16 | 23.9 |
| 17 | 24.4 |
| 18 | 25.3 |
| 19 | 26.6 |
| 20 | 28.3 |

Citrate salt form Citrate-NF1 can be further characterized by following physical properties:

Citrate content (determined by 1H-NMR spectroscopy) is 0.8 eq. Citrate);

Thermal behavior of form Citrate-NF1 shows strong endothermic events >180° C., which goes along with strong weight loss in the TGA profile. This can be assigned to melting/decomposition processes of form Citrate-NE1;

Water Vapor Sorption behavior of form Citrate-NF1 reveals very small water uptake levels ≤1.5 wt % in the relative humidity (rh) range 0-90% rh. Form Citrate-NF1 can be classified as slightly hygroscopic acc. to Ph. Eur. criteria (section 5.11.). Water Vapour Sorption isotherm (25° C.) of form Citrate-NF1 is displayed in FIG. 9c; and/or Dissolution level of form Citrate-NF1 in Fed-State Simulated Intestinal Fluid [FeSSIF, pH 5.0] at 37° C. is 4.13±0.02 mg/mL (after 15 min), approx. 4.20±0.02 mg/mL (after 60 min), and approx. 4.21±0.02 mg/mL (after 120 min), respectively (see example 17).

In another aspect the invention provides a crystalline form of Rimeporide sulfate salt, designated as form Sulfate-NF3. Form Sulfate-NF3 can be characterized by following data:
a) a powder X-ray diffraction pattern having one, two, three, four or five peaks at a diffraction angle 2 theta of 12.9°±0.2°, 15.3°±0.2°, 21.2°±0.2°, 21.6°±0.2° and/or 22.8°±0.2°;
b) a powder X-ray diffraction pattern having a peaks at a diffraction angle 2 theta of 12.9°±0.2°, 15.3°±0.2°, 21.2°±0.2°, 21.6°±0.2° and/or 22.8°±0.2° and also having one, two, three, four or five additional peaks at a diffraction angle 2 theta of 11.6°±0.2°, 17.1°±0.2°, 17.5°±0.2°, 23.8°±0.2° and/or 25.8°±0.2°;
c) a powder X-ray diffraction pattern according to TableSulfate-NF3; d) a XRPD pattern substantially as depicted in FIG. 10a;
e) DSC data substantially as depicted in FIG. 10c;
f) TGA data substantially as depicted in FIG. 10d;
g) monoclinic space group Pbcn; or
h) unit cell lattice parameters a=9.1±0.2 Å, b=12.9±0.2 Å, and c=27.3±0.2 Å (with α=β=γ=90°);
and by a combination of these data such as in particular a combination of a) and e), f), g) and/or h); b) and e), g) and/or h); c) and e), f), g) and/or h); d) and e), f), g) and/or h).

A peak list corresponding to the XRPD of FIG. 10a is shown in TableSulfate-NF3.

| TableSulfate-NF3: Powder X-ray peak list of Sulfate salt form Sulfate-NF3: | |
|---|---|
| No. | °2θ (Cu-Kα₁ radiation) ± 0.4° |
| 1 | 11.6 |
| 2 | 11.8 |
| 3 | 12.9 |
| 4 | 13.5 |
| 5 | 13.6 |
| 6 | 15.1 |
| 7 | 15.3 |
| 8 | 16.1 |
| 9 | 17.1 |
| 10 | 17.5 |
| 11 | 18.0 |
| 12 | 19.4 |
| 13 | 21.2 |
| 14 | 21.6 |
| 15 | 22.8 |
| 16 | 23.8 |
| 17 | 24.0 |
| 18 | 25.8 |
| 19 | 28.3 |
| 20 | 29.4 |

The crystal structure of Sulfate-NF3 is shown in FIG. 10b indicates that form Sulfate-NF3 represents a sulfate salt, which may incorporate a non-stoichiometric amount of water into a void.

Sulfate salt form Sulfate-NF3 is further characterised by one or more of following physical properties:

Sulfate content (determined by ion chromatography) is 22.4 wt % Sulfate (corresponding to 0.49 eq. Sulfate);

Thermal behaviour of form Sulfate-NF3 shows an endothermic event >210° C. This can be assigned to melting process of form Sulfate-NF3. DSC and TGA profiles are displayed in FIGS. 10c and 10d;

Water Vapor Sorption behaviour of form Sulfate-NF3 reveals very small water uptake levels ≤0.5 wt % in the relative humidity (rh) range 0-80% rh. Form Sulfate-NF3 can be classified as slightly hygroscopic acc. to Ph. Eur. criteria (section 5.11.); and/or Dissolution level of form Sulfate-NF3 in Fed-State Simulated Intestinal Fluid [FeSSIF, pH 5.0] at 37° C. is 3.70±0.02 mg/mL (after 15 min), 4.65±0.02 mg/mL (after 60 min), and 4.70±0.02 mg/mL (after 120 min), respectively (see example 17).

In another aspect the invention provides a crystalline form of Rimeporide besylate salt, designated as form Besylate-NF1. Form Besylate-NF1 can be characterized by following data:
a) a powder X-ray diffraction pattern having one, two, three, four or five peaks at a diffraction angle 2 theta of 5.5°±0.2°, 11.5°±0.2°, 12.1°±0.2°, 19.0°±0.2° and/or 20.3°±0.2°;
b) a powder X-ray diffraction pattern having a peaks at a diffraction angle 2 theta of 5.5°±0.2°, 11.5°±0.2°, 12.1°±0.2°, 19.0°±0.2° and 20.3°±0.2° and also having one, two, three, four or five additional peaks at a diffraction angle 2 theta of 5.9°±0.2°, 11.0°±0.2°, 11.2°±0.2°, 21.9°±0.2° and/or 22.5°±0.2°;
c) a powder X-ray diffraction pattern according to TableBesylate-NF1;
d) a XRPD pattern substantially as depicted in FIG. 11a;
e) DSC data substantially as depicted in FIG. 11b; or
f) TGA data substantially as depicted in FIG. 11c;

and by a combination of these data such as in particular a combination of a) and e) and/or f); b) and e) and/or f); c) and e) and/or f); and d) and e) and/or f).

A peak list corresponding to the XRPD of FIG. 11a is shown in TableBesylate-NF1.

| TableBesylate-NF1: Powder X-ray peak list of Besylate salt form Besylate-NF1: | |
|---|---|
| No. | °2θ (Cu-Kα$_1$ radiation) ± 0.2° |
| 1 | 5.5 |
| 2 | 5.9 |
| 3 | 11.0 |
| 4 | 11.2 |
| 5 | 11.5 |
| 6 | 12.1 |
| 7 | 14.0 |
| 8 | 14.7 |
| 9 | 17.3 |
| 10 | 17.7 |
| 11 | 19.0 |
| 12 | 20.3 |
| 13 | 20.7 |
| 14 | 21.9 |
| 15 | 22.5 |
| 16 | 23.1 |
| 17 | 25.2 |
| 18 | 25.5 |
| 19 | 28.3 |
| 20 | 29.6 |

Besylate form. Besylate-NF1 is further characterised by one or more of following physical properties:
  Besylate content (determined by 1H-NMR spectroscopy) of 1.3 eq. Besylate;
  Thermal behaviour of form Besylate-NF1 shows strong endothermic events >290° C. This can be assigned to melting process of form Besylate-NF1. DSC and TGA profiles are displayed in FIGS. 11b and 11c;
  Water Vapour Sorption behaviour of form Besylate-NF1 reveals very small water uptake levels 1.0 wt % in the relative humidity (rh) range 0-80% rh. Form Besylate-NF1 can be classified as slightly hygroscopic acc. to Ph. Eur. criteria (section 5.11.); and/or
  Dissolution level of form Besylate-NF1 in Fed-State Simulated Intestinal Fluid [FeSSIF, pH 5.0] at 37° C. is 5.57±0.02 mg/mL (after 15 min), 5.57±0.02 mg/mL (after 60 min), and 3.87±0.02 mg/mL (after 120 min), respectively (see example 17).

In another aspect the invention provides a crystalline form of Rimeporide p-tosylate salt, designated as form Tosylate-NF1. Form Tosylate-NF1 can be characterized by data:
  a) a powder X-ray diffraction pattern having one, two, three, four or five peaks at a diffraction angle 2 theta of 5.3°±0.2°, 5.7°±0.2°, 11.1°±0.2°, 18.9°±0.2° and/or 20.6°±0.2°;
  b) a powder X-ray diffraction pttern having peaks at a diffraction angle 2 theta of 5.3°±0.2°, 5.7°±0.2°, 11.1°±0.2°, 18.9°±0.2° and 20.6°±0.2° and also having one, two, three, four or five additional peaks at a diffraction angle 2 theta of 10.6°±0.2°, 12.6°±0.2°, 20.4°±0.2°, 21.3°±0.2° and/or 22.1°±0.2°;
  c) a powder X-ray diffraction pattern according to Table-Tosylate-NF1;
  d) a XRPD pattern substantially as depicted in FIG. 12a;
  e) DSC data substantially as depicted in FIG. 12b; or
  f) TGA data substantially as depicted in FIG. 12c;
and by a combination of these data such as in particular a combination of a) and e) and/or f); b) and e) and/or f); c) and e) and/or f); and d) and e) and/or f).

A peak list corresponding to the XRPD of FIG. 11a is shown in TableTosylate-NF1.

| TableTosylate-NF1: Powder X-ray peak list of p-Tosylate salt form Tosylate-NF1: | |
|---|---|
| No. | °2θ (Cu-Kα$_1$ radiation) ± 0.2° |
| 1 | 5.3 |
| 2 | 5.7 |
| 3 | 10.6 |
| 4 | 10.8 |
| 5 | 11.1 |
| 6 | 12.6 |
| 7 | 13.6 |
| 8 | 14.2 |
| 9 | 16.6 |
| 10 | 18.5 |
| 11 | 18.9 |
| 12 | 20.4 |
| 13 | 20.6 |
| 14 | 21.3 |
| 15 | 22.1 |
| 16 | 24.1 |
| 17 | 24.7 |
| 18 | 26.0 |
| 19 | 28.4 |
| 20 | 28.6 | p-Tosylate salt form Tosylate-NF1 can be further characterised by following physical properties:
  Tosylate content (determined by 1H-NMR spectroscopy) of 1.2 eq. Tosylate;
  Thermal behaviour of form Tosylate-NF1 shows a strong endothermic event >280° C. This can be assigned to melting process of form Tosylate-NF1. DSC and TGA profiles are displayed in FIGS. 12b and 12c;
  Water Vapour Sorption behaviour of form Tosylate-NF1 reveals very small water uptake levels 1.0 wt % in the relative humidity (rh) range 0-80% rh. Form Tosylate-NF1 can be classified as slightly hygroscopic acc. to Ph. Eur. criteria (section 5.11.); and/or
  Dissolution level of form Tosylate-NF1 in Fed-State Simulated Intestinal Fluid [FeSSIF, pH 5.0] at 37° C. is 4.85±0.02 mg/mL (after 15 min), 5.28±0.02 mg/mL (after 60 min), and 2.86±0.02 mg/mL (after 120 min), respectively (see example 17).

In another aspect the invention provides a crystalline form of Rimeporide malonate salt, designated as form Malonate-NF1. Form Malonate-NF1 can be chars acterized by data:
  a) a powder X-ray diffraction pattern having one, two, three, four or five peaks at a diffraction angle 2 theta of 17.3°±0.2°, 18.2°±0.2°, 19.4°±0.2° 20.1°±0.2° and/or 23.2°±0.2°;
  b) a powder X-ray diffraction pattern having peaks at a diffraction angle 2 theta of 17.3°±0.2°, 18.2°±0.2°, 19.4°±0.2°, 20.1°±0.2° and 23.2°±0.2° and also having one, two, three, four or five additional peaks at a diffraction angle 2 theta of 7.0°±0.2°, 12.5°±0.2°, 13.1°±0.2°, 19.1°±0.2° and/or 22.5°±0.2°;
  c) a powder X-ray diffraction pattern according to Table-Malonate-NF1;
  d) a XRPD pattern substantially as depicted in FIG. 13a;
  e) DSC data substantially as depicted in FIG. 13b; or
  f) TGA data substantially as depicted in FIG. 13c;
and by a combination of these data such as in particular a combination of a) and e) and/or f); b) and e) and/or f); c) and e) and/or f); and d) and e) and/or f).

A peak list corresponding to the XRPD of FIG. 13a is shown in TableMalonate-NF1.

| TableMalonate-NF1: Powder X-ray peak list of Malonate salt form Malonate-NF1: | |
|---|---|
| No. | °2θ (Cu-Kα₁ radiation) ± 0.2° |
| 1 | 7.0 |
| 2 | 8.9 |
| 3 | 9.7 |
| 4 | 10.6 |
| 5 | 12.5 |
| 6 | 13.1 |
| 7 | 13.9 |
| 8 | 15.5 |
| 9 | 17.3 |
| 10 | 18.2 |
| 11 | 19.1 |
| 12 | 19.4 |
| 13 | 20.1 |
| 14 | 22.5 |
| 15 | 22.6 |
| 16 | 22.8 |
| 17 | 23.2 |
| 18 | 25.5 |
| 19 | 26.9 |
| 20 | 29.5 |

Malonate salt form Malonate-NF1 is characterised by one or more of following physical properties:

Malonate content (determined by 1H-NMR spectroscopy) of 1.4 eq. Malonate;

Thermal behaviour of form. Malonate-NF1 shows strong endothermic events >190° C. This can be assigned to melting process of form Malonate-NF1. DSC and TGA profiles are displayed in FIGS. 13b and 13c;

Water Vapour Sorption behaviour of form Malonate-NF1 reveals very small water uptake levels ≤1.0 wt % in the relative humidity (rh) range 0-80% rh. Form Malonate-NF1 can be classified as slightly hygroscopic acc. to Ph. Eur. criteria (section 5.11.); and/or Dissolution level of form Malonate-NF1 in Fed-State Simulated Intestinal Fluid [FeSSIF, pH 5.0] at 37° C. is 4.85±0.02 mg/mL (after 15 min), 5.77±0.02 mg/mL (after 60 min), and 5.79±0.02 mg/mL (after 120 min), respectively (see example 17).

In another aspect the invention provides a crystalline form of succinate salt, designated as form. Succinate-NF1. Form Succinate-NF1 can be characterized by following data:
  a) a powder X-ray diffraction pattern having one, two, three, four or five peaks at a diffraction angle 2 theta of 12.8°±0.2° 13.9°±0.2°, 18.1°±0.2°, 18.4°±0.2° and/or 23.6°±0.2°;
  b) a powder X-ray diffraction pattern having peaks at a diffraction angle 2 theta of 12.8°±0.2°, 13.9°±0.2°, 18.1°±0.2°, 18.4°±0.2° and 23.6°±0.2° and also having one, two, three, four or five additional peaks at a diffraction angle 2 theta of 7.3°±0.2°, 16.9°±0.2°, 19.3°±0.2°, 23.1°±0.2° and/or 27.8°±0.2°;
  c) a powder X-ray diffraction pattern according to Table-Succinate-NF1;
  d) a XRPD pattern substantially as depicted in FIG. 14a;
  e) DSC data substantially as depicted in FIG. 14b; or
  f) TGA data substantially as depicted in FIG. 14c;
and by a combination of these data such as in particular a combination of a) and e) and/or f); b) and e) and/or f); c) and e) and/or f); and d) and e) and/or f).

A peak list corresponding to the XRPD of FIG. 14a is shown in TableSuccinate-NF1.

| Powder X-ray peak list of succinate salt form Succinate-NF1: | |
|---|---|
| No. | °2θ (Cu-Kα₁ radiation) ± 0.2° |
| 1 | 7.3 |
| 2 | 8.4 |
| 3 | 11.2 |
| 4 | 12.8 |
| 5 | 13.9 |
| 6 | 16.9 |
| 7 | 18.1 |
| 8 | 18.4 |
| 9 | 19.3 |
| 10 | 20.0 |
| 11 | 20.7 |
| 12 | 22.7 |
| 13 | 23.1 |
| 14 | 23.6 |
| 15 | 24.3 |
| 16 | 25.4 |
| 17 | 26.5 |
| 18 | 27.1 |
| 19 | 27.8 |
| 20 | 28.1 |

Furthermore, succinate salt form Succinate-NF1 can be characterised by one or more of following physical properties:

Succinate content (determined by 1H-NMR spectroscopy) of 1.0 eq. Succinate;

Thermal behaviour of form. Succinate-NF1 shows strong endothermic events >200° C. This can be assigned to melting process of form Succinate-NF1. DSC and TGA profiles are displayed in FIGS. 14b and 14c;

Water Vapour Sorption behaviour of form Succinate-NF1 reveals very small water uptake levels ≤0.2 wt % in the relative humidity (rh) range 0-80% rh. Form Succinate-NF1 can be classified as non-hygroscopic acc. to Ph. Eur. criteria (section 5.11.). Water Vapour Sorption isotherm (25° C.) of form Succinate-NF1 is displayed in FIG. 14d; and/or Dissolution level of form Succinate-NF1 in Fed-State Simulated Intestinal Fluid [FeSSIF, pH 5.0] at 37° C. is 3.26±0.02 mg/mL (after 15 min), 5.10±0.02 mg/mL (after 60 min), and 5.03±0.02 mg/mL (after 120 min), respectively (see example 17).

In another aspect the invention provides a crystalline form of Rimeporide fumarate salt, designated as form Fumarate-NF1. Form Fumarate-NF1 can be characterized by following data:
  a) a powder X-ray diffraction pattern having one, two, three, four or five peaks at a diffraction angle 2 theta of 4.9°±0.2°, 9.9°±0.2°, 17.1°±0.2°, 21.9°±0.2° and/or 25.3°±0.2°;
  b) a powder X-ray diffraction pattern having a peaks at a diffraction angle 2 theta of 4.9°±0.2°, 9.9°±0.2°, 17.1°±0.2°, 21.9°±0.2° and 25.3°±0.2° and also having any one, two, three, four or five additional peaks at a diffraction angle 2 theta of 9.1'°±0.2°, 11.9°±0.2°, 18.2°±0.2°, 21.0°±0.2° and 21.2°±0.2°;
  c) a powder X-ray diffraction pattern according to Table-Fumarate-NF1;
  d) a XRPD pattern substantially as depicted in FIG. 15a;
  e) DSC data substantially as depicted in FIG. 15b; or
  f) TGA data substantially as depicted in FIG. 15c;
and by a combination of these data such as in particular a combination of a) and e) and/or f); b) and e) and/or f); c) and e) and/or f); and d) and e) and/or f).

A peak list corresponding to the XRPD of FIG. 15a is shown in TableFumarate-NF-1.

| TableFumarate-NF-1: Powder X-ray peak list of Fumarate salt form Fumarate-NF1: | |
|---|---|
| No. | °2θ (Cu-Kα$_1$ radiation) ± 0.2° |
| 1 | 4.9 |
| 2 | 9.1 |
| 3 | 9.5 |
| 4 | 9.9 |
| 5 | 11.9 |
| 6 | 14.3 |
| 7 | 14.8 |
| 8 | 16.5 |
| 9 | 17.1 |
| 10 | 18.2 |
| 11 | 18.4 |
| 12 | 19.9 |
| 13 | 21.0 |
| 14 | 21.2 |
| 15 | 21.9 |
| 16 | 22.9 |
| 17 | 24.2 |
| 18 | 25.3 |
| 19 | 26.0 |
| 20 | 26.8 |

Fumarate salt form Fumarate-NF1 can be further characterised by one or more of following physical properties:
Fumarate content (determined by $^1$H-NMR spectroscopy) of 1.0 eq. Fumarate, and 0.4 eq. 2-PrOH;
Thermal behaviour of form Fumarate-NF1 shows strong endothermic events >200° C., which goes along with strong weight loss steps in the TGA profile. This can be assigned to melting/decomposition processes of form Fumarate-NF1. Prior to melting/decomposition, TGA profile reveals a weight loss step (~3.5 wt %) up to ~165° C., which goes along with a broad endothermic event in the DSC profile. This event can be attributed to thermal desolvation of 2-PrOH. DSC and TGA profiles are displayed in FIGS. 15b and 15c;
Water Vapour Sorption behaviour of form Fumarate-NF1 reveals very small water uptake levels 0.3.5 wt % in the entire relative humidity (rh) range 0-98% rh. Form Fumarate-NF1 can be classified as slightly hygroscopic acc. to Ph. Eur. criteria (section 5.11.). Water Vapour Sorption isotherm (25° C.) of form Fumarate-NF1 is displayed in FIG. 15d; and/or
Dissolution level of form Fumarate-NF1 in Fed-State Simulated Intestinal Fluid [FeSSIF, pH 5.0] at 37° C. is 4.22±0.02 mg/mL (after 15 min), 4.34±0.02 mg/mL (after 60 min), and 4.36±0.02 mg/mL (after 120 min), respectively (see example 17).

In another aspect the invention provides a crystalline form of Rimeporide tartrate salt, designated as form Tartrate-NF1. Form Tartrate-NF1 can be characterized by following data:
a) a powder X-ray diffraction pattern having one, two, three, four or five peaks at a diffraction angle 2 theta of 15.1°±0.2°, 18.7°±0.2° 19.9°±0.2°, 20.8°±0.2° and/or 22.8°±0.2°;
b) a powder X-ray diffraction pattern having a peaks at a diffraction angle 2 theta of 15.1°±0.2°, 18.7°±0.2°, 19.9°±0.2°, 20.8°±0.2° and 22.8°±0.2° and also having any one, two, three, four or five additional peaks at a diffraction angle 2 theta 8.8°±0.2°, 11.0°±0.2°, 12.9°±0.2°, 22.3°±0.2° and 23.0°±0.2° degrees two theta;
c) a powder X-ray diffraction pattern according to TableTartrate-NF1;
d) a XRPD pattern substantially as depicted in FIG. 16a;
e) DSC data substantially as depicted in FIG. 16b;
f) TGA data substantially as depicted in FIG. 16c; and and by a combination of these data such as in particular a combination of a) and e) and/or f); b) and e) and/or f); c) and e) and/or f); and d) and e) and/or f).

A peak list corresponding to the XRPD of FIG. 16a is shown in TableTartrate-NF1.

| TableTartrate-NF1: Powder X-ray peak list of Tartrate salt form Tartrate-NF1: | |
|---|---|
| No. | °2θ (Cu-Kα$_1$ radiation) ± 0.2° |
| 1 | 4.3 |
| 2 | 8.8 |
| 3 | 11.0 |
| 4 | 12.4 |
| 5 | 12.9 |
| 6 | 13.2 |
| 7 | 15.1 |
| 8 | 17.1 |
| 9 | 17.4 |
| 10 | 17.8 |
| 11 | 18.7 |
| 12 | 19.9 |
| 13 | 20.8 |
| 14 | 22.3 |
| 15 | 22.8 |
| 16 | 23.0 |
| 17 | 23.8 |
| 18 | 25.1 |
| 19 | 28.6 |
| 20 | 29.1 |

Tartrate salt form Tartrate-NF1 is characterised by one or more of following physical properties:
Tartrate content (determined by $^1$H-NMR spectroscopy) of 1.1 eq. Tartrate, and 0.7 eq. 2-PrOH;
Thermal behaviour of form Tartrate-NF1 shows strong endothermic events >150° C. This can be assigned to melting processes of form Tartrate-NF1. Prior to melting, TGA profile reveals a weight loss step (~7.3 wt %) up to ~80° C. This event can be attributed to thermal desolvation of 2-PrOH. DSC and TGA profiles are displayed in FIGS. 16b and 16c;
Water Vapour Sorption behaviour of form Tartrate-NF1 reveals very small water uptake levels ≤1.0 wt % in the relative humidity (rh) range 0-90% rh. Form Tartrate-NF1 can be classified as slightly hygroscopic acc. to Ph. Eur. criteria (section 5.11.). Water Vapour Sorption isotherm (25° C.) of form Tartrate-NF1 is displayed FIG. 16d; and/or
Dissolution level of form Tartrate-NF1 in Fed-State Simulated Intestinal Fluid [FeSSIF, pH 5.0] at 37° C. is 5.17±0.02 mg/mL (after 15 min), 5.17±0.02 mg/mL (after 60 min), and 5.17±0.02 mg/mL (after 120 min), respectively (see example 17).

In another aspect the invention provides a crystalline form of Rimeporide malate salt, designated as form Malate-NF1. Form Malate-NF1 can be characterized by following data:
a) a powder X-ray diffraction pattern having one, two, three, four or five peaks at a diffraction angle 2 theta of 5.3°±0.2°, 12.6°±0.2°, 17.2°±0.2°, 18.0°±0.2° and/or 18.4°±0.2°;
b) a powder X-ray diffraction pattern having peaks at a diffraction angle 2 theta of 5.3±0.2°, 12.6°±0.2°, 17.2°±0.2°, 18.0°±0.2° and 18.4°±0.2° and also having one, two, three, four or five peaks at a diffraction angle 2 theta of 12.3°±0.2°, 13.3°±0.2°, 13.8°±0.2°, 20.0°±0.2° and 23.8°±0.2°;

c) a powder X-ray diffraction pattern according to TableMalate-NF1;
d) a XRPD pattern substantially as depicted in FIG. 17a;
e) DSC data substantially as depicted in FIG. 17b; or
f) TGA data substantially as depicted in FIG. 17c;
and by a combination of these data such as in particular a combination of a) and e) and/or f); b) and e) and/or f); c) and e) and/or f); and d) and e) and/or f).

A peak list corresponding to the XRPD of FIG. 17a is shown in TableMalate-NF1.

| TableMalate-NF1: Powder X-ray peak list of Malate salt form Malate-NF1: | |
|---|---|
| No. | °2θ (Cu-Kα$_1$ radiation) ± 0.2° |
| 1 | 2.6 |
| 2 | 5.3 |
| 3 | 9.8 |
| 4 | 11.9 |
| 5 | 12.3 |
| 6 | 12.6 |
| 7 | 13.3 |
| 8 | 13.8 |
| 9 | 15.3 |
| 10 | 17.2 |
| 11 | 18.0 |
| 12 | 18.4 |
| 13 | 20.0 |
| 14 | 21.4 |
| 15 | 21.7 |
| 16 | 22.0 |
| 17 | 22.7 |
| 18 | 23.8 |
| 19 | 25.4 |
| 20 | 27.7 |

Malate salt form Malate-NF1 can be further characterised by one or more of following physical properties:

Malate content (determined by $^1$H-NMR spectroscopy) of 1.1 eq. Malate, and 0.7 eq. 2-PrOH;

Thermal behaviour of form Malate-NF1 shows strong endothermic events >120° C. This can be assigned to melting/decomposition processes of form Malate-NF1. Overlapping with melting/decomposition, TGA profile reveals a weight loss step (~6.1 wt %) up to ~137° C., which can be attributed to thermal desolvation of 2-PrOH. DSC and TGA profiles are displayed FIGS. 17b and 17c;

Water Vapour Sorption behaviour of form Malate-NF1 reveals very small water uptake levels 7.5 wt % in relative humidity (rh) range 0-90% rh. Form Malate-NF1 can be classified as hygroscopic acc. to Ph. Eur. criteria (section 5.11.). Water Vapour Sorption isotherm (25° C.) of form Malate-NF1 is displayed in FIG. 17d; and/or Dissolution level of form Malate-NF1 in Fed-State Simulated Intestinal Fluid [FeSSIF, pH 5.0] at 37° C. was determined to be 5.51±0.02 mg/mL (after 1.5 min), 5.51±0.02 mg/mL (after 60 min), and 4.27±0.02 mg/mL (after 120 min), respectively (see example 17).

In another aspect the invention provides a crystalline form of Rimeporide HBr salt, designated as form HBr-NF1. Form HBr-NF1 can be characterized be following data:

a) a powder X-ray diffraction pattern having one, two, three, four or five peaks at a diffraction angle 2 theta of 10.7°±0.2°, 11.1°±0.2°, 20.6°±0.2°, 22.2°±0.2° and/or 23.7°±0.2°;

b) a powder X-ray diffraction pattern having peaks at a diffraction angle 2 theta of 10.7°±0.2°, 11.1°±0.2°, 20.6°±0.2°, 22.2°±0.2° and 23.7°±0.2° and also having any one, two, three, four or five additional peaks at a diffraction angle 2 theta of 6.9°±0.2°, 17.4°±0.2°, 21.2°±0.2°, 21.4°±0.2° and 25.1°±0.2°;

c) a powder X-ray diffraction pattern according to TableHBr-NF1;

d) a XRPD pattern substantially as depicted in FIG. 18a;
e) DSC data substantially as depicted in FIG. 18b;
f) TGA data substantially as depicted in FIG. 18c; or
and by a combination of these data such as in particular a combination of a) and e) and/or f); b) and e) and/or f); c) and e) and/or; and d) and e) and/or f).

A peak list corresponding to the XRPD of FIG. 18a is shown in TableHBr-NF1.

| TableHBr-NF1: Powder X-ray peak list of HBr salt form HBr-NF1: | |
|---|---|
| No. | °2θ (Cu-Kα$_1$ radiation) ± 0.2° |
| 1 | 6.9 |
| 2 | 9.4 |
| 3 | 10.0 |
| 4 | 10.7 |
| 5 | 11.1 |
| 6 | 15.0 |
| 7 | 15.7 |
| 8 | 17.4 |
| 9 | 18.9 |
| 10 | 19.2 |
| 11 | 19.6 |
| 12 | 20.6 |
| 13 | 21.2 |
| 14 | 21.4 |
| 15 | 22.2 |
| 16 | 23.7 |
| 17 | 25.1 |
| 18 | 25.8 |
| 19 | 26.9 |
| 20 | 29.7 |

HBr salt form HBr-NF1 can be further characterised by one or more of following physical properties:

HBr content (determined by ion chromatography) of 19.2 wt % Bromide (corresponding to 1.0 eq. Bromide).

Thermal behaviour of form HBr-NF1 shows strong endothermic events >250° C., which goes along with beginning strong weight loss in TGA profile. This can be assigned to melting/decomposition processes of form HBr-NF1. Prior to melting, TGA profile reveals weight loss steps (~5-6 wt %) up to ~150° C. This can be attributed to thermal dehydration. DSC and TGA profiles are displayed in FIGS. 18b and 18c.

Water Vapour Sorption behaviour of form HBr-NF1 reveals almost constant water uptake levels 4.3-4.4 wt % in the relative humidity (rh) range 10-90% rh. Form HBr-NF1 can be classified as non-hygroscopic acc. to Ph. Eur. criteria (section 5.11.). Water Vapour Sorption isotherm (25° C.) of form HBr-NF1 is displayed in FIG. 18d.

Depending on the solid state form they are compared with, the solid state forms of the present invention may have advantageous properties selected from at least one of: chemical or polymorphic purity, increased crystallinity, solubility, dissolution rate, bioavailability, morphology or crystal habit, specific surface and pycnometric density, chemical stability, thermal stability, mechanical stability, a lower degree of hygroscopicity, low content of residual solvents and advantageous processing and handling characteristics (e.g. compressibility, flowability and bulk/tap density).

Following properties of the solid state forms according to the invention may be particular advantageous over prior-art form HCl-H1:

HCl salt form HCl-A1 is an anhydrous crystalline morphic form with very good crystallinity.

HCl salt form HCl-A2 is an anhydrous crystalline morphic form with very good crystallinity. Moreover, HCl-A2 has a very high thermal stability (mp/dec>240° C.).

HCl salt form HCl-A3 an anhydrous crystalline morphic form with very good crystallinity. Moreover, HCl-A3 has a high thermal stability (mp/dec>240° C.).

Phosphate salt form. Phosphate-NF1 is another anhydrous crystalline morphic form with very good crystallinity and high thermal stability (mp/dec>230° C.). Phosphate salt form Phosphate-NF1 is slightly hygroscopic acc. to Ph. Eur., with no tendency to undergo hydrate formation upon exposure to elevated RH levels. Phosphate salt form Phosphate-NF1 is characterized by an improved dissolution behavior in biorelevant media under Fed-state conditions (FeSSIF, pH 5.0) compared to of prior-art form HCl-H1.

Citrate salt form Citrate-NF1 is an anhydrous crystalline morphic form with very good crystallinity. Citrate salt form Citrate-NF1 has a high thermal stability (mp/dec ~180° C.), hence no risk of phase conversion due to dehydration upon thermal processing. Citrate salt form Citrate-NF1 is slightly hygroscopic acc. to Ph. Eur., with no tendency to undergo hydrate formation upon exposure to elevated RH levels. Compared to prior-art form HCl-H1, citrate salt form Citrate-NF1 has an improved dissolution behavior in biorelevant media under Fed-state conditions (FeSSIF, pH 5.0).

Oxalate salt form Oxalate-NF1 is an anhydrous crystalline morphic form with very good crystallinity. Oxalate salt form Oxalate-NF1 has a high thermal stability (mp/dec>260° C.). Oxalate salt form Oxalate-NF1 is non-hygroscopic acc. to Ph. Eur., with no tendency to undergo hydrate formation upon exposure to elevated RH levels. Oxalate salt form Oxalate-NF1 has an improved dissolution behavior in biorelevant media under Fed-state conditions (FeSSIF, pH 5.0) compared to prior-art form HCl-H1.

Maleate salt form Maleate-NF1 is another anhydrous crystalline morphic form with very good crystallinity and high thermal stability (mp/dec>170° C.).

Maleate salt form Maleate-NF2 is an anhydrous crystalline morphic form with very good crystallinity and high thermal stability (mp/dec>200° C.). Maleate salt form Maleate-NF2 is non-hygroscopic acc. to Ph. Eur., with no tendency to undergo hydrate formation upon exposure to elevated RH levels. Maleate salt form Maleate-NF2 has an improved dissolution behavior in biorelevant media under Fed-state conditions compared to prior-art form HCl-H1 (FeSSIF, pH 5.0).

Sulfate salt form Sulfate-NF3 is an anhydrous crystalline morphic form with very good crystallinity and high thermal stability (mp/dec>210° C. Sulfate salt form Sulfate-NF3 is slightly hygroscopic acc. to Ph. Eur., Sulfate salt form Sulfate-NF3 is characterized by an improved dissolution behavior in biorelevant media under Fed-state conditions (FeSSIF, pH 5.0) compared to prior-art form HCl-H1.

Besylate salt form Besylate-NF1 is an anhydrous crystalline morphic form with very good crystallinity. Besylate salt form Besylate-NF1 shows a high thermal stability (mp/dec>280° C.). Besylate salt form Besylate-NF1 is slightly hygroscopic acc. to Ph. Eur., Besylate salt form Besylate-NF1 NF2 has an improved dissolution behavior in biorelevant media under Fed-state conditions compared to prior-art form HCl-H1 (FeSSIF, pH 5.0).

p-Tosylate salt form Tosylate-NF1 is an anhydrous crystalline morphic form with very good crystallinity. p-Tosylate salt form Tosylate-NF1 is thermally stable up to ~180° C. p-Tosylate salt form Tosylate-NF1 is slightly hygroscopic acc. to Ph. Eur., p-Tosylate salt form Tosylate-NF1 has an improved dissolution behavior in biorelevant media under Fed-state conditions compared to prior-art form HCl-H1 (FeSSIF, pH 5.0).

Malonate salt form Malonate-NF1 is an anhydrous crystalline morphic form with very good crystallinity. Malonate salt form Malonate-NF1 shows a high thermal stability (mp/dec>190° C.), hence no risk of phase conversion due to dehydration upon thermal processing. Malonate salt form Malonate-NF1 has an improved dissolution behavior in biorelevant media under Fed-state conditions (FeSSIF, pH 5.0) compared to prior-art form HCl-H1.

Succinate salt form Succinate-NF1 is an anhydrous crystalline morphic form with very good crystallinity and high thermal stability (mp/dec>200° C. Succinate salt form Succinate-NF1 is non-hygroscopic acc. to Ph. Eur. and shows an improved dissolution behavior in biorelevant media under Fed-state conditions (FeSSIF, pH 5.0) compared to prior-art form. HCl-H1.

Fumarate salt form Fumarate-NF1 is an anhydrous crystalline morphic form with very good crystallinity. Fumarate salt form Fumarate-NF1 is only slightly hygroscopic acc. to Ph. Eur. and shows an improved dissolution behavior in biorelevant media under Fed-state conditions (FeSSIF, pH 5.0) compared to prior-art form HCl-H1.

Tartrate salt form Tartrate-NF1 is an anhydrous crystalline morphic form with very good crystallinity. Tartrate salt form Tartrate-NF1 is slightly hygroscopic acc. to Ph. Eur. and shows an improved dissolution behavior in biorelevant media under Fed-state conditions (FeSSIF, pH 5.0) compared to prior-art form HCl-H1.

Malate salt form Malate-NF1 is an anhydrous crystalline morphic form with very good crystallinity and shows an improved dissolution behavior in biorelevant media under Fed-state conditions (FeSSIF, pH 5.0) compared to prior-art form HCl-H1.

In general, anhydrous solid state forms are particular advantageous with regard to the process and/or manufacture of solid drug substances, because anhydrates don't have any risk of phase conversion due to dehydration upon thermal processing.

In a further aspect of the invention a crystalline compound according to the present invention is provided for use as a medicament.

The invention also relates to a crystalline compound according to the present invention for use in the treatment of a disease selected from muscular dystrophy (in particular muscular dystrophy with dilated cardiomyopathy; in particular Duchenne Muscular Dystrophy, Becker muscular dystrophy, Emery Dreifuss muscular dystrophy, myotonic dystrophy, limb girdle muscular dystrophies, RyR1 muscular dystrophy), myocardial ischemia, reperfusion, cardiac hypertrophy, cancer (in particular melanoma, breast cancer, colon carcinoma, NSCLC, and leukaemias; to increase efficacy of chemotherapies or to overcome resistance to chemotherapeutic agents), nephrotic syndromes (such as focal segmental glomerulosclerosis, diabetic nephropathy, renal impairment), neurodegenerative diseases (such as Alzheimer's disease, parkinson's disease) insulin resistance, diabetes mellitus type 2, metabolic syndrome, pulmonary hypertension (such as pulmonary arterial hypertension (including IPAH, HPAH, drug- and toxin-induced PAH, APAH, PHN, PVOD and/or PCH), pulmonary hypertension due to left heart diseases, pulmonary hypertension due to lung diseases and/or hypoxemia, CTEPH, PH with unclear multifactorial mechanisms), diabetic and/or neuropathy, for the enhancement of insulin sensitivity and the preservation or increase of β-cell compensation diseases being linked thereof.

In addition, the invention relates to a pharmaceutical composition comprising a therapeutically effective amount of at least one crystalline compound according to the present invention. In a specific embodiment, the pharmaceutical composition further comprises at least one additional compound selected from the group consisting of physiologically acceptable excipients, auxiliaries, adjuvants, diluents, carriers and/or additional pharmaceutically active substances other than the crystalline compounds according to the present invention.

The present invention further encompasses a kit comprising a therapeutically effective amount of at least one crystalline compound according to the present invention and/or at least one pharmaceutical composition according to the present invention and a therapeutically effective amount of at least one further pharmacologically active substance other than the crystalline compounds according to the present invention.

The present invention further encompasses a method for treating muscular dystrophy, comprising administering to a human in need of such a treatment a therapeutically effective amount of crystalline compound according to the present invention.

Products of the invention may be used in combination with one or more other pharmacologically active substances (ingredients, drugs) in the treatment, prevention, suppression or amelioration of diseases or conditions for which products of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a product of the invention. When a product of the invention is used contemporaneously with one or more other drugs, a combination product containing such other drug(s) and the product of the invention is preferred. However, combination therapy also includes therapies in which the product of the invention and one or more other drugs are administered on different overlapping schedules. It is contemplated that when used in combination with other active ingredients, the product of the present invention or the other active ingredient or both may be used effectively in lower doses than when each is used alone. Accordingly, the pharmaceutical compositions of the present invention (pharmaceutical compositions as described herein) include those that contain one or more other active ingredients, in addition to a product of the invention.

Examples of other pharmacologically active substances (ingredients, drugs) that may be administered in combination with a product of the invention, and either administered separately or in the same pharmaceutical composition, include, but are not limited to the compounds classes and specific compounds listed in Table 1:

TABLE 1

| Disease | Class of compounds | Example of compounds |
| --- | --- | --- |
| Neuromuscular diseases and cardiomyopathy | Exon skipping, corticosteroids, anti-fibrotic, ACE inhibitors, Angiotensin II receptors Blockers, Beta blockers, | Eteplirsen, drisapersen, ataluren, idebenone, halofuginone, prednisolone, deflazacort, enalapril, ramipril, quinalapril, lisinopril, quinalapril, losartan, olmesartan, irbesartan, bisoprolol, propranolol. |
| Oncology | Anti-angiogenics, anti tumorigenics | Cisplatinum, carboplatinum, vinblastine, vincristine, imatinib, camptothecin, gemcitabine, paclitaxel, |
| Beta cell dysfunction | Biguanides, sulfonylureas, meglitinides, Glucagon-likepeptide-1 receptor agonists (GLP1 agonists), Dipeptidyl peptidase inhibitors (DDP4 inhibitors), thiazolidindione | Metformin, Glibenclamide, exenatide, liraglutilde, insulin, repaglinide, pioglitazone, sitagliptine, |
| Kidney diseases | Diuretics, corticosteroids, immunosuppressants, calcineurin inhibitors, ACE inhibitors, Angiotensin II receptors Blockers | Furosemide, Mycophenolate mofetil, methotrexate, enalapril, ramipril, quinalapril, lisinopril, quinalapril, losartan, olmesartan, irbesartan. |
| Neurodegenerative diseases | Dopaminergic agonists, monoamine oxidase B (MAO-B) inhibitors, anticholinergics, catechol-O-methyltransferase (COMT) inhibitors, cholinesterase inhibitors, NMDA receptors antagonists | Carbidopa, levodopa, Bromocriptine, Selegiline, rasagiline, entacapone, tolcapone, Benzotropine mesylate, Donepezil, galantamine and rivastigmin, memantine |

The pharmaceutical compositions of the present invention (as described herein) may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art.

In general, non-chemical routes for the production of pharmaceutical compositions and/or pharmaceutical preparations comprise processing steps on suitable mechanical means known in the art that transfer one or more products of the invention into a dosage form suitable for administration to a patient in need of such a treatment. Usually, the transfer of one or more products of the invention into such a dosage form comprises the addition of one or more compounds, selected from the group consisting of carriers, excipients, auxiliaries and pharmaceutical active ingredients other than the products of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The products of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the products of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and, suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suits able for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The products of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically to effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the products of the invention is known to the skilled artisan or can be easily determined by standard methods known in the art.

The products of the invention and the additional pharmacologically active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind, of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

The present invention further encompasses a process for manufacturing of a crystalline modification according to the present invention.

A specific embodiment includes a process for manufacturing of crystalline modification HCl-A1 comprising following steps:
  Providing a dispersion of Rimeporide HCl salt in isobutanol, wherein the free base concentration is preferably in the range of 50-100 mg/mL;
  Agitation of the dispersion at ambient temperature; and
  Separation of the solid material and subsequent drying of the solid material at ambient temperature (preferably under nitrogen atmosphere).

A further specific embodiment includes a process for manufacturing of crystalline modification HCl-A1 comprising following steps:
  Providing a dispersion of Rimeporide HCl salt in a mixture of methanol/methylisobutylketone (preferably 1:1 (v/v)), wherein the free base concentration is preferably in the range of 5-20 mg/mL;
  Agitation of the dispersion at ambient temperature; and
  Separation of the solid material, subsequent evaporation of the resulting solution to dryness.

Another embodiment includes a process for manufacturing of crystalline modification HCl-A2 comprising following steps:
  Providing a dispersion of Rimeporide HCl salt in 2-propanol, wherein the free base concentration is preferably in the range ~50-100 mg/mL;
  Agitation of the dispersion at ambient temperature; and
  Separation of the solid material and subsequent drying of the solid material at ambient temperature (preferably under nitrogen atmosphere).

Another embodiment includes a process for manufacturing of crystalline modification HCl-A3 comprising following steps:
  Providing a dispersion of Rimeporide HCl salt in n-butanol, wherein the free base concentration is preferably in the range of ~50-100 mg/mL;
  Agitation of the dispersion at ambient temperature; and
  Separation of the solid material and subsequent drying of the solid at ambient temperature (preferably under nitrogen atmosphere).

Another embodiment includes a process for manufacturing of crystalline modification Phosphate-NF1 comprising following steps:
  Providing a solution of Rimeporide free base in 2-propanol at a temperature of 60° C.±5° C., wherein the free base concentration is preferably in the range of ~10-20 mg/mL;
  Addition of diluted solution of concentrated phosphoric acid (preferably water:aqueous phosphoric acid solution (85%) 1:10 (v:v));
  Repetitive cooling/heating cycles (preferably 3 cycles) from 60° C.±5° C. to 5° C.±5° C. (preferably with 0.1 K/min);
  Separation of the obtained solid-state material subsequent drying at ambient temperature (preferably under nitrogen atmosphere).

In a specific embodiment of such a manufacturing process a post slurry step (stirring) is performed after the repetitive cooling/heating cycles. The post slurry step is preferably performed at a temperature of 5° C.±5° C. (preferably for at least 4 h).

Another embodiment includes a process for manufacturing of crystalline modification Maleate-NF1 comprising following, steps:
  Providing a solution of Rimeporide free base in 2-propanol at a temperature of 60° C.±5° C., wherein the free base concentration is preferably in the range of 10-20 mg/mL;
  Addition of maleic acid (1.0-1.3 eq., preferably 1.1-1.2 eq.);
  The obtained solution is objected to repetitive cooling/heating cycles (preferably 3 cycles) from 60° C.±5° C. to 5° C.±5° C. (preferably with 0.1 K/min);
  Separation of the obtained solid-state material subsequent drying at ambient temperature (preferably under nitrogen atmosphere).

Such a process is particularly suitable for scale in the range of 10-100 mg (free base). In a specific embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Maleate-NF2 comprising following steps:
- Providing a solution of Rimeporide free base in 2-propanol at a temperature of 60° C.±5° C., wherein the free base concentration is preferably in the range of ~30-60 mg/mL;
- Addition of maleic acid (1.0-1.3 eq., preferably 1.1-1.2 eq.);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent drying at ambient temperature (preferably under nitrogen atmosphere).

Such a process is particularly suitable for scale in the range of 100-1000 mg. In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Oxalate-NF1 comprising following steps:
- Providing a solution of Rimeporide free base in 2-propanol at a temperature of 60° C.±5° C., wherein the free base concentration is preferably in the range of ~30-60 mg/mL;
- Addition of oxalic acid (1.0-1.3 eq., preferably 1.1-1.2 eq.);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Citrate-NF1 comprising following steps:
- Providing a solution of Rimeporide free base in 2-propanol at a temperature of 60° C.±5° C., wherein the free base concentration is preferably in the range of ~30-60 mg/mL;
- Addition of citric acid (1.0-1.3 eq., preferably 1.1-1.2 eq.);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Sulfate-NF3 comprising following steps:
- Providing a solution of Rimeporide free base in 2-propanol at a temperature of 60° C.±5° C., wherein the free base concentration is preferably in the range of ~30-60 mg/mL;
- Addition of a diluted solution of concentrated sulfuric acid (preferably water:aqueous sulfuric acid solution (95%) 1:10 (v:v);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Besylate-NF1 comprising following steps:
- Providing a solution of Rimeporide free base in 2-propanol at a temperature of 60° C.±5° C., wherein the free base concentration is preferably in the range of ~30-60 mg/mL;
- Addition of benzene sulfonic acid (1.0-1.3 eq., preferably 1.1-1.2 eq.);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Tosylate-NF1 comprising following steps:
- Providing a solution of Rimeporide free base in 2-propanol at a temperature of 60° C.±5° C., wherein the free base concentration is preferably in the range of ~30-60 mg/mL;
- Addition of p-toluenesulfonic acid monohydrate (1.0-1.3 eq., preferably 1.1-1.2 eq.);
- The obtained solution is subjected to repetitive cooling/heating cycles (preferably 3 cycles) from 60° C.±5° C. to 5° C.±5° C. (preferably with 0.1 K/min);
- Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Malonate-NF1 comprising following steps:

Providing a solution of Rimeporide free base in 2-propanol at a temperature of 60° C.±5° C., wherein the free base concentration is preferably in the range of ~30-60 mg/mL;

Addition of malonic acid (1.0-1.3 eq., preferably 1.1-1.2 eq.);

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Succinate-NF1 comprising following steps:

Providing a solution of Rimeporide free base in 2-propanol at a temperature of 60° C.±5° C., wherein the free base concentration is preferably in the range of ~30-60 mg/mL;

Addition of succinic acid (1.0-1.3 eq., preferably 1.1-1.2 eq.);

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification Fumarate-NF1 comprising following steps:

Providing a solution of Rimeporide free base in 2-propanol at a temperature of 60° C.±5° C., wherein the free base concentration is preferably in the range of ~30-60 mg/mL;

Addition of a fumaric acid (1.0-1.3 eq., preferably 1.1-1.2 eq.);

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of a crystalline modification Tartrate-NF1 comprising following steps:

Providing a solution of Rimeporide free base in 2-propanol at a temperature of 60° C.±5° C., wherein the free base concentration is preferably in the range of 30-60 mg/mL;

Addition of a DL-trataric acid (1.0-1.3 eq., preferably 1.1-1.2 eq.);

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent drying at ambient temperature (preferably under nitrogen atmosphere)

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of a crystalline modification Malate-NF1 comprising following steps:

Providing a solution of Rimeporide free base in 2-propanol at a temperature of 60° C.±5° C., wherein the free base concentration is preferably in the range of ~30-60 mg/mL;

Addition of a D-malic acid (1.0-1.3 eq., preferably 1.1-1.2 eq.);

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Another embodiment includes a process for manufacturing of crystalline modification HBr-NF1 comprising following steps:

Providing a solution of Rimeporide free base in 2-propanol at a temperature of 60° C.±5° C., wherein the free base concentration is preferably in the range of ~30-60 mg/mL;

Addition of a diluted solution of concentrated HBr (preferably water:aqueous HBr solution (47%) 1:10 (v:v));

The obtained solution is subjected to repetitive cooling/heating cycles (preferably 3 cycles) from 60° C.±5° C. to 5° C.±5° C. (preferably with 0.1 K/min);

Separation of the obtained solid-state material subsequent drying at ambient temperature (preferably under nitrogen atmosphere).

In a specific and particular preferred embodiment of such a manufacturing process a post slurry step is performed after the repetitive cooling/heating cycles. The post slurry step is preferably performed at a temperature of 5° C.±5° C. (preferably for at least 4 h).

Below and above, ambient temperature is understood to be a temperature in the range of 20° C.±2° C. to 23° C.±2° C.

In the course of the present invention, all general and individual specific temperatures given herein, for instance as part of the various process steps and substeps, refer to temperatures at standard pressure (approx. 1000 hPa/1000 mbar). It is well-known to the person skilled in the art that reduction or increase of pressure affects the general and individual specific temperatures given herein, i.e. a reduction of pressure will lead to lower respective temperatures whereas an increase will result in higher respective temperatures. It lies within the expert knowledge of the skilled artisan to adopt the herein disclosed process steps and substeps to lower and higher pressures, i.e. adopting the respective temperatures accordingly. Such temperature-adopted processes are within the scope and spirit of the present invention.

BRIEF DESCRIPTION OF THE DRAWINGS

FIG. 1a shows a typical Powder X-ray diffractogram of HCl salt form HCl-H1;

FIG. 1b depicts the single crystal structure of HCl salt form HCl-H1 viewed approx. along a-axis;

FIG. 1c shows a typical DSC scan of HCl salt form HCl-H1 (5 K/min);

FIG. 1d shows a typical TGA scan of HCl salt form HCl-H1 (5 K/min);

FIG. 1e shows a typical Water Vapour Sorption Isotherm (25° C.) of HCl salt form HCl-H1;

FIG. 2a shows a typical Powder X-ray diffractogram of HCl salt form HCl-A1;

FIG. 2b depicts the single crystal structure of HCl salt form HCl-A1 viewed approx. along a-axis;

FIG. 3a shows a typical Powder X-ray diffractogram of HCl salt form HCl-A2;

FIG. 3b depicts the single crystal structure of HCl salt form HCl-A2 viewed approx. along [111];

FIG. 3c shows a typical DSC scan of HCl salt form HCl-A2 (5 K/min);

FIG. 3d shows a typical TGA scan of NCl salt form HCl-A2 (5 K/min);

FIG. 3e shows a typical Water Vapour Sorption Isotherm (25° C.) of HCl salt form HCl-A2;

FIG. 4a shows a typical Powder X-ray diffractogram of HCl salt form HCl-A3;

FIG. 4b depicts the single crystal structure of HCl salt form HCl-A3 viewed approx. along b-axis;

FIG. 4c shows a typical DSC scan of HCl salt form HCl-A3 (5 K/min);

FIG. 4d shows a typical TGA scan of HCl salt form HCl-A3 (5 K/min);

FIG. 4e shows a typical Water Vapour Sorption Isotherm (25° C.) of HCl salt form HCl-A3;

FIG. 5a shows a typical Powder X-ray diffractogram of phosphate salt form Phosphate-NF1;

FIG. 5b shows a typical DSC scan of phosphate salt form Phosphate-NF1 (5 K/min);

FIG. 5c shows a typical TGA scan of phosphate salt form Phosphate-NF1 (5 K/min);

FIG. 5d shows a typical Water Vapour Sorption Isotherm (25° C.) of phosphate salt form Phosphate-NF1;

FIG. 6a shows a typical Powder X-ray diffractogram of maleate salt form Maleate-NF1;

FIG. 6b shows a typical TGA scan of maleate salt form Maleate-NF1 (5 K/min);

FIG. 7a shows a typical Powder X-ray diffractogram of maleate salt form Maleate-NF2;

FIG. 7b shows a typical DSC scan of maleate salt form Maleate-NF2 (5 K/min);

FIG. 7c shows a typical TGA scan of maleate salt form Maleate-NF2 (5 K/min);

FIG. 7d shows a typical Water Vapour Sorption Isotherm (25° C.) of maleate salt form Maleate-NF2;

FIG. 8a shows a typical Powder X-ray diffractogram of oxalate salt form Oxalate-NF;

FIG. 8b shows a typical DSC scan of oxalate salt form Oxlate-NF1 (5 K/min);

FIG. 8c shows a typical TGA scan of oxalate salt form Oxalate-NF1 (5 K/min);

FIG. 9a shows a typical Powder X-ray diffractogram of citrate salt form Citrate-NF1;

FIG. 9b shows a typical DSC scan of citrate salt form Citrate-NF1 (5 K/min);

FIG. 9c shows a typical TGA scan of Citrate salt form Citrate-NF1 (5 K/min);

FIG. 9d shows a typical Water Vapour Sorption Isotherm (25° C.) of citrate salt form Citrate-NF1;

FIG. 10a shows a typical Powder X-ray diffractogram of sulfate salt form Sulfate-NF3;

FIG. 10b depicts the crystal structure of sulfate salt form Sulfate-NF3 viewed approx. along [110];

FIG. 10c shows a typical. DSC scan of sulfate salt form Sulfate-NF3 (5 K/min);

FIG. 10d shows a typical TGA scan of sulfate salt form Sulfate-NF3 (5 K/min);

FIG. 10e shows a typical Water Vapour Sorption. Isotherm (25° C.) of sulfate salt form Sulfate-NF3;

FIG. 11a shows a typical Powder X-ray diffractogram of besylate salt form Besylate-NF1;

FIG. 11b shows a typical DSC scan of Besylate salt form besylate-NF1 (5 K/min);

FIG. 11c shows a typical TGA scan of Besylate salt form besylate-NF1 (5 K/min);

FIG. 11d shows a typical Water Vapour Sorption Isotherm (25° C.) of besylate salt form Besylate-NF1;

FIG. 12a shows a typical Powder X-ray diffractogram of p-tosylate salt form Tosylate-NF1;

FIG. 12b shows a typical. DSC scan of tosylate salt form Tosylate-NF1 (5 K/min);

FIG. 12c shows a typical TGA scan of tosylate salt form. Tosylate-NF1 (5 K/min);

FIG. 12d shows a typical Water Vapour Sorption Isotherm (25° C.) of tosylate salt form Tosylate-NF1;

FIG. 13a shows a typical Powder X-ray diffractogram of malonate salt form Malonate-NF1;

FIG. 13b shows a typical DSC scan of malonate salt form Malonate-NF1 (5 K/min);

FIG. 13c shows a typical TGA scan of malonate salt form Malonate-NF1 (5 K/min);

FIG. 13d shows a typical Water Vapour Sorption Isotherm (25° C.) of malonate salt form Malonate-NF1;

FIG. 14a shows a typical Powder X-ray diffractogram of succinate salt form Succinate-NF1;

FIG. 14b shows a typical DSC scan of succinate salt form Succinate-NF1 (5 K/min);

FIG. 14c shows a typical TGA scan of succinate salt form Succinate-NF1 (5 K/min);

FIG. 14d shows a typical Water Vapour Sorption Isotherm (25° C.) of succinate salt form Succinate-NF1;

FIG. 15a shows a typical Powder X-ray diffractogram of fumarate salt form Fumarate-NF1;

FIG. 15b shows a typical DSC scan of fumarate salt form Fumarate-NF1 (5 K/min);

FIG. 15c shows a typical TGA scan of fumarate salt form Fumarate-NF1 (5 K/min);

FIG. 15d shows a typical Water Vapour Sorption Isotherm (25° C.) of fumarate salt form Fumarate-NF1;

FIG. 16a shows a typical Powder X-ray diffractogram of tartrate salt form Tartrate-NF1;

FIG. 16b shows a typical DSC scan of tartrate salt form Tartrate-NF1 (5 K/min);

FIG. 16c shows a typical TGA scan of tartrate salt form Tartrate-NF1 (5 K/min);

FIG. 16d shows a typical Water Vapour Sorption Isotherm (25° C.) of tartrate salt form Tartrate-NF1;

FIG. 17a shows a typical Powder X-ray diffractogram of malate salt form Malate-NF1;

FIG. 17b shows a typical DSC scan of malate salt form Malate-NF1 (5 K/min);

FIG. 17c shows a typical TGA scan of malate salt form. Malate-NF1 (5 K/min);

FIG. 17d shows a typical Water Vapour Sorption Isotherm (25° C.) of malate salt form. Malate-NF1;

FIG. 18a shows a typical Powder X-ray diffractogram of HBr salt form HBr-NF1;

FIG. 18b shows a typical DSC scan of HBr salt form HBr-NF1 (5 K/min);

FIG. 18c shows a typical TGA scan of HBr salt form HBr-NF1 (5 K/min); and

FIG. 18d shows a typical Water Vapour Sorption Isotherm (25° C.) of HBr salt form HBr-NF1.

The invention is explained in more detail by means of the following examples without, however, being restricted thereto.

EXAMPLES

Example 1: Prior Art Form a) Re-Work of Example 4 of EP 0 758 644 B1

Approx. 30 mg N-(4,5-bismethanesulfonyl-2-methylbenzoyl)guanidine (free base) are dispersed in 5 mL of DI Water at RT (approx. 22° C.). Approx. 180 μL of 1N HCl solution is added, and resulting dispersion is filtrated (0.45 μm PTFE membrane filter) to obtain a clear solution. The clear solution is frozen in liquid nitrogen in a 50 mL round-bottom flask. Frozen sample is then attached to a lyophilisator (Steris, Lyovac GT2) operating at approx. 0.3 mbar. After 1 day, a white solid residue is obtained as dry powder.

Chemical purity ≥98% (NMR analysis).

| PXRD: | |
|---|---|
| No. | °2θ (Cu-Kα$_1$ radiation) ± 0.2° |
| 1 | 9.5 |
| 2 | 10.7 |
| 3 | 11.1 |
| 4 | 15.8 |
| 5 | 17.4 |
| 6 | 19.1 |
| 7 | 19.7 |
| 8 | 20.5 |
| 9 | 20.7 |
| 10 | 21.3 |
| 11 | 21.6 |
| 12 | 22.4 |
| 13 | 22.5 |
| 14 | 23.9 |
| 15 | 25.1 |
| 16 | 26.1 |
| 17 | 27.1 |
| 18 | 28.7 |
| 19 | 29.9 |
| 20 | 30.5 | b) Re-Work of Example 3.1 of WO 01/30750 A1:

2.7 kg of N-(4,5-bismethanesulfonyl-2-methylbenzoyl)guanidine are suspended in 25 l of water at 60°, and 10.6 l of 1N HCl solution are added. On warming to 80° C., a clear solution is obtained. The solution is allowed to cool slowly, with crystallisation beginning at 50°, giving N-(4,5-bismethanesulfonyl-2-methylbenzoyl)guanidine, hydrochloride hydrate in a yield of 97%, mp 181-188°.

1H NMR (400 MHz, DMSO-d6) δ=12.71 (s, 1H), 8.70 (s br, 2H), 8.59-8.41 (m, 3H), 8.19 (s, 1H), 3.53 (s, 3H), 3.51 (s, 3H), 2.64 (s, 3H).

Chemical purity ≥98% (NMR analysis).

Example 2: Further Characterization of HCl Salt Form HCl-H1 (Prior Art Form)

Analytical characterization showed that the solid material, which was obtained in example 1a) and example 1b) shows matching analytical data. Thus, the methods described in example 1a) and example 1b) provide the same crystalline modification, which is herein referred to as HCl-H1. A detailed characterization of crystalline form HCl-H1 is described below.

A Powder X-Ray Diffraction pattern of HCl salt form HCl-H1, which was obtained by standard techniques as described in the European Pharmacopeia 6th Edition chapter 2.9.33, is characterised by the X-ray powder diffractogram (monochromatic Cu-Kα$_1$ radiation, A=1.5406 Å, Stoe StadiP 611 KL transmission diffractometer) shown in FIG. 1a, the corresponding Powder X-ray peak list is shown in TableHCl-H1.

| TableHCl-H1: Powder X-ray peak list of HCl salt form HCl-H1: | |
|---|---|
| No. | °2θ (Cu-Kα$_1$ radiation) ± 0.2° |
| 1 | 9.5 |
| 2 | 10.8 |
| 3 | 11.1 |
| 4 | 15.8 |
| 5 | 17.4 |
| 6 | 19.1 |
| 7 | 19.7 |
| 8 | 20.6 |
| 9 | 20.8 |
| 10 | 21.4 |
| 11 | 21.6 |
| 12 | 22.4 |
| 13 | 22.5 |
| 14 | 23.9 |
| 15 | 25.1 |
| 16 | 26.1 |
| 17 | 27.1 |
| 18 | 28.7 |
| 19 | 29.9 |
| 20 | 30.5 |

According to single crystal X-Ray Structure data obtained on HCl salt form HCl-H1 (see FIG. 1b, Oxford Diffraction Xcalibur™ Single Crystal X-ray Diffractometer with Sapphire CCD Detector at 303 K) HCl salt form HCl-H1 crystallizes in the monoclinic space group P21/c with the lattice parameters a=5.3±0.1 Å, b=18.6±0.1 Å, c=17.6±0.1 Å, and β=92.9±0.5° (with α=γ=90°). The single crystal structure shows that form HCl-H1 represents an HCl salt monohydrate form.

HCl salt form HCl-H1 is further characterised by following physical properties:

Chloride content (determined by ion chromatography) reveals 8.5 wt % chloride (corresponds to 0.93 eq. Chloride taking into account water content of 4.6 wt %).

Water content (determined by Karl-Fischer titration) reveals 4.6 wt % water (corresponds to 0.98 eq. water taking into account Chloride content of 8.5 wt %).

Thermal behavior of form HCl-H1 shows broad endothermic events overlapping with a TGA step in the temperature range ~80-150° C., which is due to thermal dehydration of the monohydrate form. A second endothermic event occurs at >180° C., which is due to melting of the dehydrated form. This is followed by immediate re-crystallisation (exothermic event), and subsequent melting of the re-crystallized phase at >240° C. DSC and TGA profiles are displayed in FIGS. 1c and 1d. DSC scan of form HCl-H1 was acquired on a Mettler-Toledo DSC 821 with a heating rate of 5 K/min, using nitrogen purge gas at 50 mL/min. TGA scan of form HCl-H1 was acquired on a Mettler-Toledo TGA 851 with a heating rate of 5 K/min, using nitrogen purge gas at 50 mL/min.

Water Vapour Sorption behavior of form HCl-H1 reveals very small water uptake levels ≤0.2 wt % in the full relative humidity (rh) range 0-98% rh. Form HCl-H1 can be classified as non-hygroscopic acc. to Ph. Eur. criteria (section 5.11.). Water Vapor Sorption isotherm (25° C.) of form HCl-H1 is displayed in FIG. 1e. Water Vapour Sorption isotherm was acquired on a DVS-1 system from SMS.

Dissolution level of form HCl-H1 in Fed-State Simulated Intestinal Fluid [FeSSIF, pH 5.0] at 37° C. was determined to be approx. 1.50 mg/mL (after 15 min), approx. 4.16 mg/mL (after 60 min), and approx. 4.54 mg/mL (after 120 min), respectively (see example 17).

Example 3: Preparation Processes for Novel Anhydrous Forms HCl-A1, HCl-A2, HCl-A3 of HCl Salt a) Form HCl'-A1:
i) Slurry Experiment in Iso-BuOH:
Approx. 50 mg of N-(4,5-bis-methanesulfonyl-2-methyl-benzoyl)-guanidine HCl salt form H1 are dispersed in 0.6 mL iso-butanol and agitated at RT (approx. 20-23° C.) for 5 days. Resulting solid-state residue is separated from supernatant liquid by centrifugation, and dried under nitrogen purge gas at ambient temperature for few hours to give a powder sample.
Chemical purity ≥98% (NMR analysis).
ii) Evaporation Crystallisation from Methanol:Methylisobutylketone (1:1, v:v):
Approx. 30 mg of N-(4,5-bis-methanesulfonyl-2-methyl-benzoyl)guanidine HCl salt form H1 are dispersed in 4 mL of a mixture of methanol:methylisobutylketone (1:1, v:v), and equilibrated at 50° C. under agitation for several hours. Non-dissolved solid-state residues after that are filtrated off (0.45 µm syringe filter), and resulting clear solution was evaporated at 50° C. to dryness to yield a powder sample.
Chemical purity ≥98% (NMR analysis).

b) Form HCl-A2:
i) Slurry Experiment in 2-PrOH:
Approx. 50 mg of N-(4,5-bis-methanesulfonyl-2-methyl-benzoyl)-guanidine HCl salt form H1 are dispersed in 0.6 mL 2-propanol and agitated at RT (approx. 20-23° C.) for 5 days. Resulting solid-state residue is separated from supernatant liquid by centrifugation, and dried under nitrogen purge gas at ambient temperature for few hours to give a powder sample.
Chemical purity ≥98% (NMR analysis).

c) Form HCl-A3:
i) Slurry Experiment in n-BuOH:
Approx. 50 mg of N-(4,5-bis-methanesulfonyl-2-methyl-benzoyl)-guanidine HCl salt form H1 are dispersed in 0.6 mL 1-butanol and agitated at RT (approx. 20-23° C.) for 5 days. Resulting solid-state residue is separated from supernatant liquid by centrifugation, and dried under nitrogen purge gas at ambient temperature for few hours to give a powder sample.
Chemical purity ≥98% (NMR analysis).

Example 4: Preparation Processes for Novel Phosphate Salt Form a) Phosphate Salt Phosphate-NF1 Preparation:
i) Experiment from 2-PrOH:
Approx. 94 mg of N-(4,5-bis-methanesulfonyl-2-methyl-benzoyl)-guanidine free base are dissolved in 8 mL of 2-propanol at 60° C. Approx. 192 µL of a 1:10 diluted solution of concentrated phosphoric acid (85%) is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.
Chemical purity ≥98% (NMR analysis).

Example 5: Preparation Processes for Novel Maleate Salt Forms a) Maleate Salt Maleate-NF1 Preparation:
i) Experiment from 2-PrOH:
Approx. 32.5 mg of N-(4,5-bis-methanesulfonyl-2-methyl-benzoyl)-guanidine free base are dissolved in 2 mL of 2-propanol at 60° C. Approx. 13 mg maleic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.
1H NMR (400 MHz, DMSO-d6) δ=8.43 (s, 1H), 8.35-7.25 (m, 5H), 6.14 (s, 2H), 3.49 (s, 3H), 3.47 (s, 3H), 2.63 (s, 3H).
Chemical purity ≥98% (NMR analysis).

b) Maleate Salt Maleate-NF2 Preparation:
i) Experiment from 2-PrOH:
Approx. 354 mg of N-(4,5-bis-methanesulfonyl-2-methyl-benzoyl)-guanidine free base are dissolved in 8 mL of 2-propanol at 60° C. Approx. 143.5 mg maleic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.
1H NMR (500 MHz, DMSO-d6) δ=8.41 (s, 1H), 8.38-7.29 (m, 5H), 6.13 (s, 2H), 3.48 (s, 3H), 3.46 (s, 3H), 2.62 (s, 3H).
Chemical purity ≥98% (NMR analysis).

Example 6: Preparation Processes for Novel Oxalate Salt Form a) Oxalate Salt Oxalate-NF1 Preparation:
i) Experiment from 2-PrOH:
Approx. 354 mg of N-(4,5-bis-methanesulfonyl-2-methyl-benzoyl)-guanidine free base are dissolved in 8 mL of 2-propanol at 60° C. Approx. 151.8 mg oxalic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

Chemical purity ≥98% (NMR analysis).

Example 7: Preparation Processes for Novel Citrate Salt Form a) Citrate Salt Citrate-NF1 Preparation:
i) Experiment from 2-PrOH:
Approx. 149 mg of N-(4,5-bis-methanesulfonyl-2-methyl-benzoyl)-guanidine free base are dissolved in 3 mL of 2-propanol at 60° C. Approx. 90.9 mg citric acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H-NMR: 1H NMR (500 MHz, DMSO-d6) δ 12.04 (s br, 2H), 8.46 (s, 1H), 8.05 (m, 3H), 6.89 (s br, 2H), 3.46 (s, 3H), 3.45 (s, 3H), 2.67 (d, J=15.3 Hz, 2H), 2.64 (s, 3H), 2.59 (d, J=15.3 Hz, 2H).

Chemical purity ≥98% (NMR analysis).

Example 8: Preparation Processes for Novel Sulfate Salt Forms a) Sulfate Salt Sulfate-NF3 Preparation:
i) Experiment from 2-PrOH:
Approx. 341 mg of N-(4,5-bis-methanesulfonyl-2-methyl-benzoyl)-guanidine free base are dissolved in 8 mL of 2-propanol at 60° C. Approx. 620 µL of a 1:10 diluted solution of concentrated sulfuric acid (95%) is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

Chemical purity ≥98% (NMR analysis).

Example 9: Preparation Processes for Novel Besylate Salt Form a) Besylate Salt Besylate-NF1 Preparation:
i) Experiment from 2-PrOH:
Approx. 147 mg of N-(4,5-bis-methanesulfonyl-2-methyl-benzoyl)-guanidine (free base) are dissolved in 3 mL of 2-propanol at 60° C. Approx. 73.4 mg benzenesulfonic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H-NMR: 1H NMR (500 MHz, DMSO-d6) δ=11.77 (s, 1H), 8.63-8.09 (m, 6H), 7.68-7.52 (m, 2H), 7.41-7.24 (m, 3H), 3.51 (s, 3H), 3.49 (s, 3H), 2.61 (s, 3H).

Chemical purity ≥0.98% (NMR analysis).

Example 10: Preparation Processes for Novel p-Tosylate Salt Form a) Tosylate Salt Tosylate-NF1 Preparation:
i) Experiment from 2-PrOH:
Approx. 150 mg of N-(4,5-bis-methanesulfonyl-2-methyl-benzoyl)-guanidine (free base) are dissolved in 3 mL of 2-propanol at 60° C. Approx. 81.3 mg p-toluenesulfonic acid monohydrate is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=11.78 (s, 1H), 8.70-7.99 (m, 6H), 7.46 (d, J=8.0 Hz, 2H), 7.11 (d, J=8.0 Hz, 2H), 3.50 (s, 3H), 3.47 (s, 3H), 2.60 (s, 3H), 2.29 (s, 3H).

Chemical purity ≥98% (NMR analysis).

Example 11: Preparation Processes for Novel Malonate Salt Form a) Malonate Salt Malonate-NF1 Preparation:
i) Experiment from 2-PrOH:
Approx. 150 mg of N-(4,5-bis-methanesulfonyl-2-methyl-benzoyl)-guanidine free base are dissolved in 3 mL of 2-propanol at 60° C. Approx. 58.5 mg malonic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=3.88 (s br, 2H), 8.44 (s, 1H), 8.40-7.47 (m, 3H), 6.90 (s br, 2H), 3.45 (s, 3H), 3.43 (s, 3H), 3.04 (s, 2H), 2.63 (s, 3H).

Chemical purity ≥98% (NMR analysis).

Example 12: Preparation Processes for Novel Succinate Salt Form a) Succinate Salt Succinate-NF1 Preparation:
i) Experiment from 2-PrOH:
Approx. 149 mg of N-(4,5-bis-methanesulfonyl-2-methyl-benzoyl)-guanidine free base are dissolved in 3 mL of 2-propanol at 60° C. Approx. 62.7 mg succinic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=14.10 (s br, 1H), 8.46 (s, 1H), 8.29-7.66 (m, 3H), 6.89 (s br, 2H), 3.46 (s, 3H), 3.44 (s, 3H), 2.64 (s, 3H), 2.34 (s, 4H).

Chemical purity ≥98% (NMR analysis).

Example 13: Preparation Processes for Novel Fumarate Salt Form a) Fumarate Salt Fumarate-NF1 Preparation:
  i) Experiment from 2-PrOH:

Approx. 347 mg of N-(4,5-bis-methanesulfonyl-2-methyl-benzoyl)guanidine free base are dissolved in 8 mL of 2-propanol at 60° C. Approx. 137.8 mg fumaric acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=8.44 (s, 1H), 8.38-7.68 (m, 3H), 6.90 (s br, 2H), 6.62 (s, 2H), 3.45 (s, 3H), 3.43 (s, 3H), 2.63 (s, 3H).

Chemical purity ≥98% (NMR analysis).

Example 14: Preparation Processes for Novel Tartrate Salt Form a) Tartrate Salt Tartrate-NF1 Preparation:
  i) Experiment from 2-PrOH:

Approx. 147 mg of N-(4,5-bis-methanesulfonyl-2-methyl-benzoyl)-guanidine free base are dissolved in 3 mL of 2-propanol at 60° C. Approx. 67.9 mg DL-tartaric acid is added to the clear solution, and the solution was subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=8.44 (s, 1H), 8.37-7.61 (m, 3H), 6.95 (s br, 2H), 4.03 (s, 2H), 3.45 (s, 3H), 3.43 (s, 3H), 2.63 (s, 3H).

Chemical purity ≥98% (NMR analysis).

Example 15: Preparation Processes for Novel Malate Salt Form a) Malate Salt Malate-NF1 Preparation:
  i) Experiment from 2-PrOH:

Approx. 151 mg of N-(4,5-bis-methanesulfonyl-2-methyl-benzoyl)-guanidine free base are dissolved in 3 mL of 2-propanol at 60° C. Approx. 65.3 mg D-malic acid is added to the clear solution, and the solution is subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=8.46 (s, 1H), 8.37-7.65 (m, 3H), 6.88 (s br, 2H), 4.32 (s br, 1H), 4.18 (t, J=6.5 Hz, 1H), 3.46 (s, 3H), 3.44 (s, 3H), 2.64 (s, 3H), 2.59 (dd, J=15.6, 6.1 Hz, 1H), 2.42 (dd, J=15.6, 6.9 Hz, 1H).

Chemical purity ≥98% (NMR analysis).

Example 16: Preparation Processes for Novel HBr Salt Form a) HBr Salt HBr-NF1 Preparation:
  i) Experiment from 2-PrOH:

Approx. 90 mg of N-(4,5-bis-methanesulfonyl-2-methyl-benzoyl)-guanidine free base are dissolved in 2 mL of 2-propanol at 60° C. Approx. 93 μL of a 1:3 diluted solution of concentrated HBr (47%) is added to the clear solution, and the solution was subjected to 3 repetitive cooling/heating cycles from 60-5° C. with 0.1 K/min, followed by a post-slurry step at the end of the 3rd cooling segment at 5° C. Obtained solid-state residue after the repetitive cooling/heating cycle is separated by centrifugation, and dried under nitrogen purge gas at ambient temperature for few hours to give a powder sample.

1H NMR (500 MHz, DMSO-d6) δ=11.77 (s, 1H), 8.64-8.08 (m, 6H), 3.50 (s, 3H), 3.49 (s, 3H), 2.61 (s, 3H).

Chemical purity ≥98% (NMR analysis).

Example 17: Mini-Dissolution Data of Novel Salt Forms Vs Prior-Art

Approximately 10-12 mg of N-(4,5-bis-methanesulfonyl-2-methyl-benzoyl)guanidine form HCl-H1 (HCl salt hydrate form, prior-art), HCl salt anhydrous forms (forms HCl-A1, HCl-A2, HCl-A3), and novel salt forms [phosphate salt (form Phosphate-NF1), maleate salt (form Maleate-NF2), oxalate salt (form Oxalate-NF1), citrate salt (form citrate-NF1), sulfate salt (form Sulfate-NF3), succinate salt (form Succinate-NF1), malonate salt (form Malonate-NF1), besylate salt (form Besylate-NF1), p-tosylate salt (form Tosylate-NF1), malate salt (form Malate-NF1), fumarate salt (form Fumarate-NF1), tartrate salt (form Tartrate-NF1)] are weighed into 4 mL glass vials, and dispersed in 4 mL FeSSIF medium (pH 5.0, Acetate buffer capacity increased by factor 4 to ensure stable pH conditions over course of dissolution experiments).

All dispersions are agitated at 37° C. for up to 2 hours. At defined time intervals (5 min, 15 min, 60 min, 120 min), 0.4 mL sample aliquots of homogeneous dispersions are withdrawn by a syringe, and filtrated via syringe filter adapters (PTFE, 0.2 μm). Clear filtrates are diluted (1:20) with respective Acetate blank buffer, and diluted samples analyzed by HPLC for dissolved quantities of N-(4,5-bis-methanesulfonyl-2-methyl-benzoyl)-guanidine.

Results from mini dissolution studies are summarized below.

| | Dissolution levels in FeSSIF pH 5.0 (mg/mL) | | | |
|---|---|---|---|---|
| Time | HCl salt HCl-H1 (prior-art) | HCl salt HCl-A1 | HCl salt HCl-A2 | HCl salt HCl-A3 |
| 5 min | 0.494 | 0.541 | 0.990 | 0.418 |
| 15 min | 1.499 | 0.866 | 1.193 | 0.738 |
| 60 min | 4.162 | 2.535 | 1.897 | 2.506 |
| 120 min | 4.543 | 2.765 | 2.213 | 3.781 |

| | Dissolution levels in FeSSIF pH 5.0 (mg/mL) | | | |
|---|---|---|---|---|
| Time | Phosphate salt Phosphate-NF1 | Maleate salt Maleate-NF2 | Oxalate salt Oxalate-NF1 | Citrate salt Citrate-NF1 |
| 5 min | 3.373 | 2.043 | 1.329 | 2.056 |
| 15 min | 5.919 | 4.296 | 2.095 | 4.132 |
| 60 min | 6.345 | 6.350 | 3.042 | 4.204 |
| 120 min | 6.345 | 6.350 | 3.025 | 4.208 |

| | Dissolution levels in FeSSIF pH 5.0 (mg/mL) | | | |
|---|---|---|---|---|
| Time | Sulfate salt Sulfate-NF3 | Succinate salt Succinate-NF1 | Malonate salt Malonate-NF1 | Besylate salt Besylate-NF1 |
| 5 min | 2.590 | 1.105 | 3.527 | 4.059 |
| 15 min | 3.703 | 3.260 | 5.340 | 5.570 |
| 60 min | 4.646 | 5.104 | 5.770 | 5.570 |
| 120 min | 4.705 | 5.032 | 5.790 | 3.873 |

| | Dissolution levels in FeSSIF pH 5.0 (mg/mL) | | | |
|---|---|---|---|---|
| Time | p-Tosylate salt Tosylate-NF1 | Malate salt Malate-NF1 | Fumarate salt Fumarate-NF1 | Tartrate salt Tartrate-NF1 |
| 5 min | 1.961 | 5.510 | 2.606 | 5.165 |
| 15 min | 4.850 | 5.510 | 4.222 | 5.165 |
| 60 min | 5.285 | 5.510 | 4.337 | 5.165 |
| 120 min | 2.859 | 4.275 | 4.361 | n.a. |

The invention claimed is:

1. A crystalline hydrochloride salt of Rimeporide, excluding crystalline modification HCl-H1.

2. The crystalline hydrochloride salt according to claim 1, wherein the crystalline hydrochloride salt is an anhydrate form.

3. The crystalline hydrochloride salt according to claim 1, said crystalline hydrochloride salt being designated as form HCl-A1, characterized by a powder X-ray diffraction pattern having one, two, three, four or five peaks at a diffraction angle (2 theta) of 14.0°±0.2°, 18.5°±0.2°, 19.6°±0.2°, 20.4°±0.2° and/or 22.1°±0.2°.

4. The crystalline hydrochloride salt according to claim 1, said crystalline hydrochloride salt being designated as form HCl-A2, characterized by powder X-ray diffraction pattern having one, two, three, four or five peaks at a diffraction angle (2 theta) of 11.9±0.2°, 14.9°±0.2°, 17.7°±0.2°, 21.8°±0.2° and/or 22.5°±0.2°.

5. The crystalline hydrochloride salt according to claim 1, said crystalline hydrochloride salt being designated as form HCl-A3, characterized by powder X-ray diffraction pattern having one, two, three, four or five peaks at a diffraction angle (2 theta) of 14.2°±0.2°, 17.1°±0.2°, 17.4°±0.2°, 18.5°±0.2° and/or 24.1°±0.2°.

6. An anhydrous crystalline salt of Rimeporide selected from phosphate salts, citrate salts, oxalate salts, maleate salts, sulfate salts, besylate salts, p-tosylate salts, malonate salts and succinate salts of Rimeporide.

7. The anhydrous crystalline salt according to claim 6, said anhydrous crystalline salt being:
a) an anhydrous crystalline phosphate salt of Rimeporide designated as form Phosphate-NF1, characterized by a powder X-ray diffraction pattern having one, two, three, four or five peaks at a diffraction angle 2 theta of 13.9°±0.2°, 16.9°±0.2°, 17.3°±0.2°, 21.8°±0.2° and/or 22.1°±0.2°;
b) an anhydrous crystalline maleate salt of Rimeporide designated as form Maleate-NF1, characterized by a powder X-ray diffraction pattern having one, two, three, four or five peaks at a diffraction angle 2 theta of 7.6±0.2°, 11.1°±0.2°, 19.5°±0.2°, 20.3°±0.2° and/or 20.7°±0.2°;
c) an anhydrous crystalline maleate salt of Rimeporide designated as form Maleate-NF2, characterized by a powder X-ray diffraction pattern having one, two, three, four or five peaks at a diffraction angle 2 theta of 16.3±0.2°, 18.7°±0.2°, 20.4°±0.2°, 20.7°±0.2° and/or 25.3°±0.2°;
d) an anhydrous crystalline oxalate salt of Rimeporide, designated as form Oxalate-NF1, characterized by a powder X-ray diffraction pattern having one, two, three, four or five peaks at a diffraction angle 2 theta of 13.2°±0.2°, 16.4°±0.2°, 17.1°±0.2°, 21.3°±0.2° and/or 23.3°±0.2°;
e) an anhydrous crystalline citrate salt of Rimeporide, designated as form Citrate-NF1, characterized by a powder X-ray diffraction pattern having one, two, three, four or five peaks at a diffraction angle 2 theta of 11.9°±0.2, 15.0°±0.2, 18.1°±0.2, 19.5°+0.2 and/or 20.3°±0.2°;
f) an anhydrous crystalline sulfate salt of Rimeporide, designated as form Sulfate-NF3, characterized by a powder X-ray diffraction pattern having one, two, three, four or five peaks at a diffraction angle 2 theta of 12.9°±0.2°, 15.3°±0.2°, 21.2°±0.2°, 21.5°±0.2° and/or 22.8°±0.2°;
g) an anhydrous crystalline besylate salt of Rimeporide, designated as form Besylate-NF1, characterized by a powder X-ray diffraction pattern having one, two, three, four or five peaks at a diffraction angle 2 theta of 5.5°±0.2°, 11.5°±0.2°, 12.1°±0.2°, 19.0°±0.2° and/or 20.3°±0.2°;
h) an anhydrous crystalline p-tosylate salt of Rimeporide, designated as form Tosylate-NF1, characterized by a powder X-ray diffraction pattern having one, two, three, four or five peaks at a diffraction angle 2 theta of 5.3°±0.2°, 5.7°±0.2°, 11.1°±0.2°, 18.9°±0.2° and/or 20.6°±0.2°;
i) an anhydrous crystalline malonate salt of Rimeporide, designated as form Malonate-NF1, characterized by a powder X-ray diffraction pattern having one, two, three, four or five peaks at a diffraction angle 2 theta of 17.3°±0.2°, 18.2°±0.2°, 19.4°±0.2°, 20.1°±0.2° and/or 23.2°±0.2°; or
j) an anhydrous crystalline succinate salt of Rimeporide, designated as form Succinate-NF1, characterized by a powder X-ray diffraction pattern having one, two, three, four or five peaks at a diffraction angle 2 theta of 12.8°±0.2°, 13.9°±0.2°, 18.1°±0.2°, 18.4°±0.2° and/or 23.6°±0.2°.

8. A crystalline salt of Rimeporide selected from:
a) a crystalline fumarate salt of Rimeporide, designated as form Fumarate-NF1, characterized by a powder X-ray diffraction pattern having one, two, three, four or five peaks at a diffraction angle 2 theta of 4.9°±0.2°, 9.9°±0.2°, 17.1°±0.2°, 21.9°±0.2° and/or 25.3°±0.2°;
b) a crystalline tartrate salt of Rimeporide, designated as form Tartrate-NF1, characterized by a powder X-ray diffraction pattern having one, two, three, four or five peaks at a diffraction angle 2 theta of 15.1°±0.2°, 18.7°±0.2°, 19.9°±0.2°, 20.8°±0.2° and/or 22.8°±0.2°;
c) a crystalline malate salt of Rimeporide, designated as form Malate-NF1, characterized by, a powder X-ray diffraction pattern having one, two, three, four or five peaks at a diffraction angle 2 theta of 5.3±0.2°, 12.6°±0.2°, 17.2°±0.2°, 18.0°±0.2° and/or 18.4°±0.2°; or
d) a crystalline HBr salt of Rimeporide, designated as form HBr-NF1, characterized by a powder X-ray diffraction pattern having one, two, three, four or five peaks at a diffraction angle 2 theta of 10.7°±0.2°, 11.1°±0.2°, 20.6°±0.2°, 22.2°±0.2° and/or 23.7°±0.2°.

9. A pharmaceutical composition comprising a therapeutically effective amount of at least one crystalline compound according to claim 1.

10. A pharmaceutical composition comprising a therapeutically effective amount of at least one crystalline compound according to claim 7.

11. A pharmaceutical composition comprising a therapeutically effective amount of at least one crystalline compound according to claim 8.

12. A method for treating muscular dystrophy, comprising administering to a human in need of such a treatment a therapeutically effective amount of crystalline compound according to claim 1.

13. A method for treating muscular dystrophy, comprising administering to a human in need of such a treatment a therapeutically effective amount of crystalline compound according to claim 7.

14. A method for treating muscular dystrophy, comprising administering to a human in need of such a treatment a therapeutically effective amount of crystalline compound according to claim 8.

* * * * *

UNITED STATES PATENT AND TRADEMARK OFFICE
CERTIFICATE OF CORRECTION

| | |
|---|---|
| PATENT NO. | : 10,981,864 B2 |
| APPLICATION NO. | : 16/076017 |
| DATED | : April 20, 2021 |
| INVENTOR(S) | : Axel Becker et al. |

It is certified that error appears in the above-identified patent and that said Letters Patent is hereby corrected as shown below:

In the Specification

Column 2,
Line 3, "tardiomyopathy" should read --cardiomyopathy--.

Column 5,
Line 54, "Cu-Kai" should read --Cu-K$\alpha_1$--.

Column 6,
Line 38, "Cu-Kai" should read --Cu-K$\alpha_1$--.

Column 9,
Line 23, "levels 0.1" should read --levels ≤ 0.1--.

Column 15,
Line 31, "Citrate-NE1;" should read --Citrate-NF1;--.
Line 66, "b) and e), g)" should read --b) and e), f), g)--.

Column 17,
Line 38, "levels 1.0" should read --levels ≤ 1.0--.
Line 54, "diffraction pttern" should read --diffraction pattern--.

Column 18,
Line 36, "levels 1.0" should read --levels ≤ 1.0--.
Line 47, "chars acterized" should read --characterized--.

Column 20,
Line 56, "9.1$^{10}$±0.2°," should read --9.1°±0.2°,--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

Column 21,
Line 39, "levels 0.3.5" should read --levels $\leq$ 3.5--.

Column 23,
Line 48, "levels 7.5" should read --levels $\leq$ 7.5--.
Line 56, "(after 1.5 min)" should read --(after 15 min)--.

Column 24,
Line 12, "e) and/or; and" should read --e) and/or f); and--.

Column 25,
Line 12, "form. Phosphate" should read --form Phosphate--.

Column 30,
Line 65, "term "therapeutically to effective amount" means" should read --term "therapeutically effective amount" means--.

Column 35,
Lines 64-65, "range of 30-60" should read --range of ~30-60--.

Column 37,
Line 28, "NCl salt" should read --HCl salt--.

Column 38,
Line 17, "Sorption. Isotherm" should read --Sorption Isotherm--.
Lines 32-33, "form. Tosylate-NF1" should read --form Tosylate-NF1--.

Column 39,
Lines 5-6, "form. Malate-NF1" should read --form Malate-NF1--.

Column 40,
Line 20, "A=1.5406" should read --$\lambda$=1.5406--.

Column 41,
Line 32, "HCl'-A1:" should read --HCl-A1:--.